(12) United States Patent
Esfandyarpour et al.

(10) Patent No.: US 10,900,075 B2
(45) Date of Patent: Jan. 26, 2021

(54) SYSTEMS AND METHODS FOR NUCLEIC ACID SEQUENCING

(71) Applicant: GenapSys, Inc., Redwood City, CA (US)

(72) Inventors: Hesaam Esfandyarpour, Redwood City, CA (US); Maryam Jouzi, Redwood City, CA (US); Seth Stern, Menlo Park, CA (US); Paul Kenney, Sunnyvale, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

(21) Appl. No.: 16/141,215

(22) Filed: Sep. 25, 2018

(65) Prior Publication Data

US 2019/0256903 A1   Aug. 22, 2019

Related U.S. Application Data

(63) Continuation of application No. PCT/US2018/052072, filed on Sep. 20, 2018.
(Continued)

(51) Int. Cl.
*C12Q 1/6869* (2018.01)
*C12Q 1/6825* (2018.01)
*C12Q 1/6837* (2018.01)

(52) U.S. Cl.
CPC ......... *C12Q 1/6869* (2013.01); *C12Q 1/6825* (2013.01); *C12Q 1/6837* (2013.01); *C12Q 2563/107* (2013.01); *C12Q 2565/30* (2013.01)

(58) Field of Classification Search
CPC .............................. C12Q 1/6869; C12Q 1/6837
See application file for complete search history.

(56) References Cited

U.S. PATENT DOCUMENTS

| 2,014,761 A | 9/1935 | Faust |
| 4,072,576 A | 2/1978 | Arwin et al. |

(Continued)

FOREIGN PATENT DOCUMENTS

| CN | 1337580 A | 2/2002 |
| CN | 101120098 A | 2/2008 |

(Continued)

OTHER PUBLICATIONS

Stout, Electrochemical Dynamics and Electrokinetic Particle Motion in Concentrated Electrolytes, Thesis, 2017, pp. 1-154 (Year: 2017).*

(Continued)

*Primary Examiner* — Narayan K Bhat
(74) *Attorney, Agent, or Firm* — Wilson Sonsini Goodrich & Rosati

(57) ABSTRACT

The present disclosure provides methods and systems for sequencing nucleic acid molecules. Methods may include sequencing double-stranded nucleic acids or single-stranded nucleic acids. Sequencing may include the use of nucleotides coupled to electrostatic moieties. The electrostatic moieties may be detected by a sensor array. The electrostatic moieties may be reversible electrostatic moieties that are cleaved from the nucleic acid molecule after incorporation of the nucleotide. The electrostatic moieties may be irreversible electrostatic moieties. Nucleotides comprising irreversible electrostatic moieties may be incorporated into the nucleic acid molecule, detected by the sensor array, and exchanged for non-detectable nucleotides.

19 Claims, 24 Drawing Sheets

Specification includes a Sequence Listing.

Related U.S. Application Data

(60) Provisional application No. 62/561,358, filed on Sep. 21, 2017, provisional application No. 62/655,083, filed on Apr. 9, 2018.

(56) References Cited

U.S. PATENT DOCUMENTS

| | | | |
|---|---|---|---|
| 5,344,545 A | 9/1994 | Tsukada et al. |
| 5,407,799 A | 4/1995 | Studier et al. |
| 5,466,348 A | 11/1995 | Holm-Kennedy |
| 5,552,270 A | 9/1996 | Khrapko et al. |
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,870,235 B2 | 3/2005 | Abstreiter et al. |
| 6,953,958 B2 | 10/2005 | Baxter et al. |
| 7,081,192 B1 | 7/2006 | Wang et al. |
| 7,095,010 B2 | 8/2006 | Scherer et al. |
| 7,223,540 B2 | 5/2007 | Pourmand et al. |
| 7,238,536 B1 | 7/2007 | Schlenoff |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |
| 7,645,596 B2 | 1/2010 | Williams et al. |
| 7,649,358 B2 | 1/2010 | Toumazou et al. |
| 7,666,598 B2 | 2/2010 | Piepenburg et al. |
| 7,682,837 B2 | 3/2010 | Jain et al. |
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,835,871 B2 | 11/2010 | Kain et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,023,113 B2 | 9/2011 | El et al. |
| 8,030,000 B2 | 10/2011 | Piepenburg et al. |
| 8,039,817 B2 | 10/2011 | Feng et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,080 B2 | 5/2012 | Lebl et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,274,040 B2 | 9/2012 | Zhong et al. |
| 8,301,394 B2 | 10/2012 | Chen et al. |
| 8,315,817 B2 | 11/2012 | Kain et al. |
| 8,392,126 B2 | 3/2013 | Mann |
| 8,426,134 B2 | 4/2013 | Piepenburg et al. |
| 8,460,875 B2 | 6/2013 | Armes et al. |
| 8,486,625 B2 | 7/2013 | Gunderson et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,649,011 B2 | 2/2014 | Mccaffrey et al. |
| 8,673,560 B2 | 3/2014 | Leamon et al. |
| 8,778,848 B2 | 7/2014 | Lin et al. |
| 8,778,849 B2 | 7/2014 | Bowen et al. |
| 8,865,077 B2 | 10/2014 | Chiou et al. |
| 8,865,078 B2 | 10/2014 | Chiou et al. |
| 8,914,241 B2 | 12/2014 | Kain et al. |
| 8,969,002 B2 | 3/2015 | Esfandyarpour et al. |
| 9,045,796 B2 | 6/2015 | Gunderson et al. |
| 9,063,117 B2 | 6/2015 | Gourley |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,188,594 B2 | 11/2015 | Fahmy et al. |
| 9,274,077 B2 | 3/2016 | Esfandyarpour et al. |
| 9,399,217 B2 | 7/2016 | Oldham et al. |
| 9,434,983 B2 | 9/2016 | Esfandyarpour |
| 9,533,305 B2 | 1/2017 | Esfandyarpour et al. |
| 9,689,835 B2 | 6/2017 | Liu et al. |
| 9,708,656 B2 * | 7/2017 | Turner ............... G01N 27/227 |
| 9,809,852 B2 | 11/2017 | Esfandyarpour et al. |
| 9,822,401 B2 | 11/2017 | Oberstrass et al. |
| 9,926,596 B2 | 3/2018 | Esfandyarpour et al. |
| 9,945,807 B2 | 4/2018 | Baghbani-Parizi et al. |
| 9,990,381 B2 | 6/2018 | Eltoukhy et al. |
| 1,005,998 A1 | 8/2018 | Esfandyarpour et al. |
| 1,009,397 A1 | 10/2018 | Esfandyarpour et al. |
| 1,010,035 A1 | 10/2018 | Esfandyarpour et al. |
| 1,012,539 A1 | 11/2018 | Esfandyarpour et al. |
| 1,026,009 A1 | 4/2019 | Esfandyarpour et al. |
| 1,026,689 A1 | 4/2019 | Esfandyarpour et al. |
| 1,047,267 A1 | 11/2019 | Esfandyarpour et al. |
| 1,049,467 A1 | 12/2019 | Esfandyarpour et al. |
| 1,053,321 A1 | 1/2020 | Oberstrass; Florian |
| 1,053,952 A1 | 1/2020 | Baghbani-Parizi et al. |
| 1,054,445 A1 | 1/2020 | Esfandyarpour et al. |
| 1,057,044 A1 | 2/2020 | Esfandyarpour et al. |
| 1,061,209 A1 | 4/2020 | Esfandyarpour et al. |
| 10,787,705 B2 | 9/2020 | Esfandyarpour et al. |
| 2002/0132245 A1 | 9/2002 | Boles et al. |
| 2002/0148739 A2 | 10/2002 | Liamos et al. |
| 2003/0078314 A1 | 4/2003 | Johnson et al. |
| 2003/0209432 A1 | 11/2003 | Choong et al. |
| 2004/0014201 A1 | 1/2004 | Kim et al. |
| 2004/0023253 A1 | 2/2004 | Kunwar et al. |
| 2004/0033492 A1 | 2/2004 | Chen |
| 2004/0136866 A1 | 7/2004 | Pontis et al. |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2005/0084980 A1 | 4/2005 | Koo et al. |
| 2005/0098434 A1 | 5/2005 | Gundel et al. |
| 2005/0123937 A1 | 6/2005 | Thorp et al. |
| 2005/0129526 A1 | 6/2005 | Dukhin et al. |
| 2005/0200648 A1 | 9/2005 | Doak et al. |
| 2005/0218464 A1 | 10/2005 | Holm-Kennedy |
| 2006/0008824 A1 | 1/2006 | Ronaghi et al. |
| 2006/0105373 A1 | 5/2006 | Pourmand et al. |
| 2006/0147955 A1 | 7/2006 | Allawi et al. |
| 2006/0170931 A1 | 8/2006 | Guo et al. |
| 2006/0199193 A1 | 9/2006 | Koo et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van et al. |
| 2008/0009420 A1 | 1/2008 | Schroth et al. |
| 2008/0032294 A1 | 2/2008 | Kawarada et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |

(56) References Cited

U.S. PATENT DOCUMENTS

| | | |
|---|---|---|
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0000957 A1 | 1/2009 | Dubin et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | Mckernan et al. |
| 2009/0191594 A1 | 7/2009 | Ohashi |
| 2010/0000881 A1 | 1/2010 | Franzen et al. |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0105035 A1 | 4/2010 | Hashsham et al. |
| 2010/0112588 A1 | 5/2010 | Farinas et al. |
| 2010/0137143 A1 | 6/2010 | Rothberg et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander et al. |
| 2011/0008775 A1 | 1/2011 | Gao et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0014837 A1 | 1/2012 | Fehr et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0052489 A1 | 3/2012 | Gordon et al. |
| 2012/0055811 A1 | 3/2012 | Rothberg et al. |
| 2012/0055813 A1 | 3/2012 | Rothberg et al. |
| 2012/0061239 A1 | 3/2012 | Elibol et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0247977 A1 | 10/2012 | Rothberg et al. |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322054 A1 | 12/2012 | Rothberg et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0045701 A1 | 2/2014 | Esfandyarpour et al. |
| 2014/0057339 A1 | 2/2014 | Esfandyarpour et al. |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour et al. |
| 2014/0235463 A1 | 8/2014 | Rothberg et al. |
| 2014/0272952 A1 | 9/2014 | May et al. |
| 2014/0329699 A1 | 11/2014 | Esfandyarpour |
| 2015/0148264 A1 | 5/2015 | Esfandyarpour et al. |
| 2015/0316502 A1 | 11/2015 | Mohanty et al. |
| 2015/0344943 A1 | 12/2015 | Oberstrass |
| 2015/0368707 A1 | 12/2015 | Esfandyarpour et al. |
| 2015/0376681 A1 | 12/2015 | Gupta et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |
| 2017/0065977 A1 | 3/2017 | Esfandyarpour et al. |
| 2017/0073750 A1 | 3/2017 | Esfandyarpour et al. |
| 2017/0088575 A1 | 3/2017 | Ju et al. |
| 2017/0211141 A1 | 7/2017 | Gordon et al. |
| 2018/0094307 A1 | 4/2018 | Oberstrass |
| 2018/0100190 A1 | 4/2018 | Esfandyarpour et al. |
| 2018/0155780 A1 | 6/2018 | Esfandyarpour et al. |
| 2018/0245150 A1 | 8/2018 | Esfandyarpour et al. |
| 2018/0282805 A1 | 10/2018 | Esfandyarpour et al. |
| 2018/0282806 A1 | 10/2018 | Esfandyarpour et al. |
| 2018/0327837 A1 | 11/2018 | Esfandyarpour |
| 2018/0335401 A1 | 11/2018 | Baghbani-Parizi et al. |
| 2019/0017103 A1 | 1/2019 | Esfandyarpour |
| 2019/0177790 A1 | 6/2019 | Esfandyarpour et al. |
| 2019/0177791 A1 | 6/2019 | Esfandyarpour et al. |
| 2020/0181692 A1 | 6/2020 | Oberstrass et al. |

(56) References Cited

U.S. PATENT DOCUMENTS

| | | | |
|---|---|---|---|
| 2020/0232024 A1 | 7/2020 | Esfandyarpour et al. | |
| 2020/0232028 A1 | 7/2020 | Esfandyarpour et al. | |

FOREIGN PATENT DOCUMENTS

| | | |
|---|---|---|
| CN | 101405083 A | 4/2009 |
| CN | 101848757 A | 9/2010 |
| CN | 101918590 A | 12/2010 |
| CN | 102980922 A | 3/2013 |
| EP | 0676623 A2 | 10/1995 |
| EP | 1333089 A1 | 8/2003 |
| EP | 1499738 B1 | 7/2008 |
| EP | 1992706 A2 | 11/2008 |
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010513869 A | 4/2010 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2004027024 A2 | 4/2004 |
| WO | WO-2004076683 A2 | 9/2004 |
| WO | WO-2005008450 A2 | 1/2005 |
| WO | WO-2005108612 A2 | 11/2005 |
| WO | WO-2005121363 A2 | 12/2005 |
| WO | WO-2006050346 A2 | 5/2006 |
| WO | WO-2007030505 A1 | 3/2007 |
| WO | WO-2007041619 A2 | 4/2007 |
| WO | WO-2007098049 A2 | 8/2007 |
| WO | WO-2008076406 A2 | 6/2008 |
| WO | WO-2008132643 A1 | 11/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 | 4/2010 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |
| WO | WO-2011106556 A2 | 9/2011 |
| WO | WO-2012047889 A2 | 4/2012 |
| WO | WO-2012166742 A2 | 12/2012 |
| WO | WO-2013082619 A1 | 6/2013 |
| WO | WO-2013119765 A1 | 8/2013 |
| WO | WO-2013188582 A1 | 12/2013 |
| WO | WO-2014012107 A2 | 1/2014 |
| WO | WO-2014043143 A1 | 3/2014 |
| WO | WO-2014152625 A1 | 9/2014 |
| WO | WO-2015089238 A1 | 6/2015 |
| WO | WO-2015138696 A1 | 9/2015 |
| WO | WO-2015161054 A2 | 10/2015 |
| WO | WO 2016/127077 * | 8/2016 |
| WO | WO-2018017884 | 1/2018 |
| WO | WO-2019060628 A1 | 3/2019 |

OTHER PUBLICATIONS

Andreotti, et al. Immunoassay of infectious agents. Biotechniques. Oct. 2003;35(4):850-9.

Bell, et al. Detection of *Bacillus anthracis* DNA by LightCycler PCR. J Clin Microbiol. Aug. 2002;40(8):2897-902.

Betz et al. KlenTaq polymerase replicates unnatural base pairs by inducing a Watson-Crick geometry. Nat Chem Biol 8:612-614 (2012).

Bobrow et al. Fundamentals of Electrical Engineering, 1995, Holt, Rinehart and Winston, Inc.

Boo, et al. Electrochemical nanoneedle biosensor based on multiwall carbon nanotube. Anal Chem. Jan. 15, 2006;78(2):617-20.

Brouns et al. Small CRISPR RNAs guide antiviral defense in prokaryotes. Science 321:960-964 (2008).

Brown et al. AC electroosmotic flow in a DNA concentrator. Microfluid Nanofluid 2:513-523 (2006).

Cagnin, et al. Overview of electrochemical DNA biosensors: new approaches to detect the expression of life. Sensors (Basel). 2009;9(4):3122-48. doi: 10.3390/s90403122. Epub Apr. 24, 2009.

Carte, et al., Cas6 is an endoribonuclease that generates guide RNAs for invader defense in prokaryotes. Genes Dev. Dec. 15, 2008;22(24):3489-96.

Cheng et al. Single-stranded DNA concentration by electrokinetic forces. J. Micro/Nanolith. MEMS MOEMS 8(2):021107 (Jun. 9, 2009). Abstract only.

Cho, et al. Bis-aptazyme sensors for hepatitis C virus replicase and helicase without blank signal. Nucleic Acids Res. Nov. 27, 2005;33(20):e177.

Co-pending U.S. Appl. No. 13/397,581, filed Feb. 15, 2012.

Co-pending U.S. Appl. No. 16/105,480, filed Aug. 20, 2018.

Co-pending U.S. Appl. No. 16/115,344, filed Aug. 28, 2018.

Co-pending U.S. Appl. No. 16/137,408, filed Sep. 20, 2018.

Cui et al., "Nanowire Nanosensors for Highly Sensitive and Selective Detection of Biological and Chemical Species", Science, vol. 293, pp. 1289-1292 (2001).

Daniels, et al. Label-Free Impedance Biosensors: Opportunities and Challenges. Electroanalysis. Jun. 2007;19(12):1239-1257.

Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.

Didion, et al., Invaders: Recognition of Double-Stranded DNA by Using Duplexes Modified with Interstrand Zippers of 2'-O-(Pyren-1-yl)methyl-ribonucleotides. Chembiochem. Sep. 2, 2013;14(13):1534-1538. doi: 10.1002/cbic.201300414. Epub 2013 Aug. 23, 2013.

Dimov, et al. Stand-alone self-powered integrated microfluidic blood analysis system (SIMBAS). Lab Chip. Mar. 7, 2011;11(5):845-50.

Edman, et al. Electric field directed nucleic acid hybridization on microchips. Nucleic Acids Res. Dec. 15, 1997; 25(24): 4907-14.

Ellington, et al. In vitro selection of RNA molecules that bind specific ligands. Nature. Aug. 30, 1990;346(6287):818-22.

EP14767683.7 Extended European Search Report dated Oct. 25, 2016.

Esfandyarpour, et al. 3D modeling of impedance spectroscopy for protein detection in nanoneedle biosensors. Proceedings of the COMSOL Conference 2007, Boston.

Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).

Esfandyarpour, et al. A Novel Nanoneedle Biosensor for DNA Sequencing (abstract). Dec. 31, 2008. Available at http://www.nsti.org/Nanotech2008/showabstract.html?absno=1522.

Esfandyarpour, et al. Geometrical Optimization of Pyrophosphate Concentration in Thermosequencing Platform for DNA Sequencing. Proceedings of the COMSOL Conf. 2007, Boston.

Esfandyarpour. Nano-Biotechnology toward Diagnostic Industry: Obstacles and Opportunities. NSTI-Nanotech, vol. 4, p. 421 (2007). Abstract Only.

European search report and search opinion dated Jan. 5, 2015 for EP Application No. 12792216.9.

European search report and search opinion dated Mar. 12, 2014 for EP Application No. 11831452.5.

(56) References Cited

OTHER PUBLICATIONS

European search report and search opinion dated Jul. 13, 2015 for EP Application No. 12852490.7.
European Search Report dated Oct. 11, 2017 for European Patent Application No. EP14869402.9.
European Search Report dated Nov. 14, 2017 for European Patent Application No. EP15779780.4.
Examination Report dated Jun. 7, 2016 for Singapore Patent Application No. SG11201402760V.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Fritz et al. Electronic detection of DNA by its intrinsic molecular charge. PNAS 99(22):14142-14146 (2002).
Gao, et al. Silicon nanowire arrays for label-free detection of DNA. Anal Chem. May 1, 2007;79(9):3291-7. Epub Apr. 4, 2007.
Gardeniers, et al. Silicon micromachined hollow microneedles for transdermal liquid transport. Journal of Microelectromechanical Systems. 2003;12(6):855-862.
Guiducci, et al. A Biosensor for Direct Detection of DNA Sequences Based on Capacitance Measurements. ESSDERC 2002, pp. 479-482.
Haurwitz, et al. Sequence- and structure-specific RNA processing by a CRISPR endonuclease. Science. Sep. 10, 2010;329(5997):1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
Hsu et al. Wafer-scale silicon nanopillars and nanocones by Langmuir-Blodgett assembly and etching. Applied Physic Lett. 93:133109-1-133109-3 (2008).
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
International search report and written opinion dated Oct. 26, 2015 for PCT/US2015/026135.
International Search Report and Written Opinion dated Nov. 16, 2017 for International PCT Patent Application No. PCT/US2017/43159.
Javanmard, et al. A microfluidic platform for electrical detection of DNA hybridization. Sens Actuators B Chem. May 20, 2011;154(1):22-27. Epub Mar. 30, 2010.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Kaushik, et al. Lack of pain associated with microfabricated microneedles. Anesth Analg. Feb. 2001;92(2):502-4.
Kim, et al. Replication of DNA microarrays prepared by in situ oligonucleotide polymerization and mechanical transfer. Anal Chem. Oct. 1, 2007;79(19):7267-74.
Kitano, et al. Molecular structure of RNA polymerase and its complex with DNA. J Biochem. Jan. 1969;65(1):1-16.
Kuhr. Capillary Electrophoresis. Anal. Chem. 62:403R-414R (1990).
Kunin, et al. Evolutionary conservation of sequence and secondary structures in CRISPR repeats. Genome Biol. 2007;8(4):R61.
Kurosaki, et al. Rapid and simple detection of Ebola virus by reverse transcription-loop-mediated isothermal amplification. J Virol Methods. Apr. 2007;141(1):78-83.
Lee, et al. Ion-sensitive field-effect transistor for biological sensing. Sensors (Basel). 2009;9(9):7111-31. doi: 10.3390/s90907111. Epub Sep. 7, 2009.
Lei et al. Electrokinetic DNA concentration in Microsystems. Sensors and Actuators. A 156(2) (2009). Abstract only.
Lin, et al. Replication of DNA microarrays from zip code masters. J Am Chem Soc. Mar. 15, 2006;128(10):3268-72.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.
Makarova, et al. A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.
Manickam, et al. A CMOS Electrochemical Impedance Spectroscopy (EIS) Biosensor Array. IEEE Trans Biomed Circuits Syst. Dec. 2010;4(6):379-90.
Margulies, et al. Genome sequencing in microfabricated high-density picolitre reactors. Nature. Sep. 15, 2005;437(7057):376-80. Epub Jul. 31, 2005.
Moser et al. Biosensor arrays for simultaneous measurement of glucose, lactate, glutamate, and glutamine. Biosens. & Bioelect. 17:297-302 (2002).
Notice of allowance dated Mar. 28, 2016 for U.S. Appl. No. 13/481,858.
Notice of Allowance dated May 12, 2017 for U.S. Appl. No. 14/653,230.
Notice of allowance dated May 19, 2016 for U.S. Appl. No. 13/481,858.
Notice of allowance dated Jun. 3, 2015 for U.S. Appl. No. 14/596,111.
Notice of allowance dated Jul. 1, 2015 for U.S. Appl. No. 13/824,129.
Notice of Allowance dated Jul. 6, 2017 for U.S. Appl. No. 14/653,230.
Notice of Allowance dated Jul. 10, 2017 for U.S. Appl. No. 14/688,764.
Notice of allowance dated Jul. 13, 2015 for U.S. Appl. No. 14/596,111.
Notice of Allowance dated Jul. 20, 2017 for U.S. Appl. No. 14/688,764.
Notice of Allowance dated Jul. 31, 2017 for U.S. Appl. No. 14/119,859.
Notice of allowance dated Aug. 25, 2015 for U.S. Appl. No. 14/596,111.
Notice of allowance dated Sep. 1, 2015 for U.S. Appl. No. 14/596,111.
Notice of Allowance dated Sep. 8, 2017 for U.S. Appl. No. 14/653,230.
Notice of allowance dated Nov. 21, 2014 for U.S. Appl. No. 13/632,513.
Notice of allowance dated Dec. 3, 2015 for U.S. Appl. No. 13/838,816.
Notice of Allowance dated Dec. 8, 2017 for U.S. Appl. No. 14/119,859.
Notice of allowance dated Dec. 15, 2015 for U.S. Appl. No. 13/838,816.
Notomi, et al. Loop-mediated isothermal amplification of DNA. Nucl Acids Res. Jun. 15, 2000; 28(12):E63.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office Action dated Feb. 14, 2017 for U.S. Appl. No. 14/653,230.
Office Action dated Mar. 4, 2016 for U.S. Appl. No. 14/081,358.
Office Action dated Apr. 5, 2017 for U.S. Appl. No. 14/859,725.
Office action dated Apr. 6, 2016 for U.S. Appl. No. 14/835,070.
Office action dated Apr. 9, 2015 for U.S. Appl. No. 14/596,111.
Office Action dated Apr. 24, 2017 for U.S. Appl. No. 14/119,859.
Office action dated May 1, 2015 for U.S. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office Action dated Sep. 1, 2017 for U.S. Appl. No. 14/361,902.
Office action dated Sep. 2, 2014 for U.S. Appl. No. 13/632,513.
Office Action dated Oct. 5, 2015 for U.S. Appl. No. 14/081,358.
Office action dated Oct. 7, 2015 for U.S. Appl. No. 13/838,816.
Office Action dated Oct. 23, 2017 for U.S. Appl. No. 14/859,725.
Office action dated Nov. 5, 2013 for U.S. Appl. No. 13/632,513.
Office action dated Dec. 17, 2015 for U.S. Appl. No. 13/481,858.
Office action dated Dec. 17, 2015 for U.S. Appl. No. 14/835,070.
Office Action dated Dec. 18, 2017 for U.S. Appl. No. 15/028,899.
Office action dated Dec. 19, 2014 for U.S. Appl. No. 13/838,816.

(56) References Cited

OTHER PUBLICATIONS

Parizi et al. A Semiconductor Nanobridge Biosensor for Electrical Detection of DNA Hybridization. IEEE Int'l SOI Conference, 2 pgs. (Oct. 6-9, 2008).
Parizi et al. An Internally Amplified Signal SOI Nano-bridge Biosensors for Electrical Detection of DNA Hybridization. IEEE Int'l SOI Conference, 2 pgs. (Oct. 5-8, 2009).
Parizi et al. BioFET for Detection of Biological Species. Stanford University, CIS (Computer-Information-System) Catalog, 1 sheet (2008).
Parizi et al. BioFET Sensor. CIS 2007—Stanford University, 33 pgs. (2007).
Parizi et al. Poster—An Internally Amplified Signal SOI Nanobridge Biosensor for Electrical Detection of DNA Hybridization or Sequence. Poster—1 sheet (Summer 2009).
Parizi et al. Poster BioFET Sensor. CIS 2007—Stanford University, 18 pgs. (2007).
Parizi et al. BioFET Sensor. CIS ADCOM Fall 2009 Stanford University, 28 pgs (Nov. 2009).
Pascault. A Finite Element Study of the DNA Hybridization Kinetics on the Surface of Microfluidic Devices. Thesis, M.S. Chem. Engineer., Worcester Polytechnic Institute, p. 1-148 (Apr. 2007).
Patolsky, et al. Electrical detection of single viruses. Proc Natl Acad Sci U S A. Sep. 18, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
PCT/US2014/069624 International Search Report dated May 22, 2015.
PCT/US2018/052072 International Search Report and Written Opinion dated Jan. 18, 2019.
Peng et al. Interdigitated Array Electrodes with Magnetic Function as a Particle-Based Biosensor. Sensors, 2007 IEEE. pp. 1097-1100.
Piepenburg, et al. DNA detection using recombination proteins. PLoS Biol. Jul. 2006;4(7):e204.
Poghossian et al. Possibilities and limitations of label-free detection of DNA hybridization with field-effect-based devices. Sensors and Actuators B 111-112:470-480 (2005).
Ramos et al. AC electric-field-induced fluid flow in microelectrodes. J Colloid Interface Sci 217:420-422 (1999).
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Rothberg, et al. An integrated semiconductor device enabling non-optical genome sequencing. Nature. Jul. 20, 2011; 475(7356); pp. 348-352. With Supplementary Information, 25 pages.
Sabounchi, et al. Sample concentration and impedance detection on a microfluidic polymer chip. Biomed Microdevices. Oct. 2008;10(5):661-70. doi: 10.1007/s10544-008-9177-4.
Safir, et al. Fabrication of an insulated probe on a self-assembled metallic nanowire for electrochemical probing in cells. IEEE 2006, pp. 898-900.
Saias et al. Design, modeling and characterization of microfluidic architectures for high flow rate, small footprint microfluidic systems. Lab Chip. Mar. 7, 2011;11(5):822-32.
Senapati, et al. A nonamembrane-based nucleic acid sensing platform for portable diagnostics. Topics in Current Chemistry. Apr. 27, 2011; 304:153-169.
Sivamani, et al. Microneedles and transdermal applications. Expert Opin Drug Deliv. Jan. 2007;4(1):19-25.
Smolina et al. End invasion of peptide nucleic acids (PNAs) with mixed-base composition into linear DNA duplexes. Nucleic Acids Research. vol. 33. No. 11. Pages e146-e146. Sep. 25, 2005.
Sosnowski, et al. Rapid determination of single base mismatch mutations in DNA hybrids by direct electric field control. Proc Natl Acad Sci U S A. Feb. 18, 1997; 94(4): 1119-1123.
U.S. Appl. No. 16/007,969 Notice of Allowance dated Nov. 26, 2018.
U.S. Appl. No. 14/361,902 Office Action dated Oct. 7, 2016.
U.S. Appl. No. 14/859,725 Notice of Allowance dated Sep. 11, 2018.
U.S. Appl. No. 14/859,725 Notice of Allowance dated Jul. 27, 2018.
U.S. Appl. No. 15/028,899 Notice of Allowance dated Jul. 25, 2018.
U.S. Appl. No. 15/360,369 Office Action dated Nov. 29, 2018.
U.S. Appl. No. 15/655,616 Office Action dated Feb. 26, 2019.
U.S. Appl. No. 16/007,829 Notice of Allowance dated Nov. 26, 2018.
U.S. Appl. No. 16/007,829 Office Action dated Sep. 17, 2018.
U.S. Appl. No. 16/007,969 Office Action dated Aug. 15, 2018.
U.S. Appl. No. 14/081,358 Notice of Allowance dated May 16, 2016.
U.S. Appl. No. 14/859,725 Notice of Allowance dated Jun. 19, 2018.
U.S. Appl. No. 14/936,245 Notice of Allowance dated Sep. 22, 2017.
U.S. Appl. No. 14/936,245 Notice of Allowance dated Dec. 6, 2017.
U.S. Appl. No. 15/950,005 Office Action dated Jan. 28, 2019.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
Tamayol et al. Laminar Flow in Microchannels With Noncircular Cross Section. J. Fluids Eng 132(11), 111201 (Nov. 3, 2010) (9 pages).
Terns et al. CRISPR-based adaptive immune systems. Curr. Opin. Microbiol. 14:321-327 (2011).
U.S. Appl. No. 15/028,899 Notice of Allowance dated Jun. 27, 2018.
U.S. Appl. No. 14/361,902 Notice of Allowance dated May 21, 2018.
U.S. Appl. No. 14/859,725 Notice of Allowance dated May 30, 2018.
U.S. Appl. No. 15/183,406 Office Action dated Jun. 21, 2018.
U.S. Appl. No. 15/230,048 Notice of Allowance dated Apr. 5, 2018.
Van Der Oost, et al. CRISPR-based adaptive and heritable immunity in prokaryotes. Trends Biochem Sci. Aug. 2009;34(8):401-7.
Voelkerding, et al. Next generation sequencing: from basic research to diagnostics. Clin. Chem. 2009; 55(4):641-658.
Wang, et al. Interaction of the Cas6 riboendonuclease with CRISPR RNAs: recognition and cleavage. Structure. Feb. 9, 2011;19(2):257-64.
Wilke et al. A micromachined capillary electrophoresis chip with fully integrated electrodes for separation and electrochemical detection. Biosens. and Bioelect. 19:149-153 (2003).
Williams, et al. Etch rates for micromachining processing. Journal of Microelectromechanical Systems 5(4):761-778 (1996).
Yazdanpanah, et al. Selective self-assembly at room temperature of individual freestanding Ag2Ga alloy nanoneedles. J. Appl. Phys. 98, pp. 073510-073517 (2005).
Zanoli et al. Isothermal Amplification Methods for the Detection of Nucleic Acids in Microfluidic Devices. Biosensors. vol. 3. No. 1. pp. 18-43. Dec. 27, 2012.
Zhang, et al. Dielectrophoresis for manipulation of micro/nano particles in microfluidic systems. Anal Bioanal Chem. Jan. 2010;396(1): 401-20.
Zheng, et al. Multiplexed electrical detection of cancer markers with nanowire sensor arrays. Nat Biotechnol. Oct. 2005;23(10):1294-301. Epub Sep. 18, 2005.
Bandiera et al. A fully electronic sensor for the measurement of cDNA hybridization kinetics. Biosensors and Bioelectronics 22:2108-2114 (2007). Available online Nov. 7, 2006.
Co-pending U.S. Appl. No. 15/930,719, filed May 13, 2020.
Co-pending U.S. Appl. No. 15/931,845, filed May 14, 2020.
Co-pending U.S. Appl. No. 16/592,545, filed Oct. 3, 2019.
Co-pending U.S. Appl. No. 16/598,591, filed Oct. 10, 2019.
Co-pending U.S. Appl. No. 16/696,690, filed Nov. 26, 2019.
Co-pending U.S. Appl. No. 16/932,437, filed Jul. 17, 2020.
EP17831906.7 Extended European Search Report dated Jan. 29, 2020.
EP19162225.7 Extended European Search Report dated Sep. 18, 2019.

(56) References Cited

OTHER PUBLICATIONS

Park et al. Control of channel doping concentration for enhancing the sensitivity of "top-down" fabricated Si nanochannel FET biosensors. Nanotechnology 20(47):475501 (Oct. 26, 2009).
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158(1-2):24-29.
Sakata et al. DNA Sequencing Based on Intrinsic Molecular Charges. Angew Chem Int Ed 45:2225-2228 (2006).
U.S. Appl. No. 15/183,406 Office Action dated Mar. 8, 2019.
U.S. Appl. No. 15/360,369 Notice of Allowance dated Oct. 10, 2019.
U.S. Appl. No. 15/360,369 Notice of Allowance dated Sep. 4, 2019.
U.S. Appl. No. 15/655,616 Notice of Allowance dated Sep. 13, 2019.
U.S. Appl. No. 15/726,193 Notice of Allowance dated Aug. 29, 2019.
U.S. Appl. No. 15/726,193 Office Action dated Apr. 16, 2019.
U.S. Appl. No. 15/726,217 Notice of Allowance dated Oct. 8, 2019.
U.S. Appl. No. 15/726,217 Notice of Allowance dated Dec. 4, 2019.
U.S. Appl. No. 15/726,217 Office Action dated Mar. 19, 2019.
U.S. Appl. No. 15/950,005 Notice of Allowance dated Sep. 13, 2019.
U.S. Appl. No. 16/137,408 Office Action dated Aug. 9, 2019.
U.S. Appl. No. 16/137,408 Office Action dated Nov. 19, 2019.
U.S. Appl. No. 16/283,531 Notice of Allowance dated Nov. 22, 2019.
U.S. Appl. No. 16/283,531 Office Action dated Jul. 18, 2019.
U.S. Appl. No. 16/283,544 Notice of Allowance dated Jul. 11, 2019.
U.S. Appl. No. 15/183,406 Office Action dated Jun. 24, 2020.
U.S. Appl. No. 15/655,616 Notice of Allowance dated Jan. 2, 2020.
U.S. Appl. No. 15/655,616 Notice of Allowance dated Oct. 10, 2019.
U.S. Appl. No. 15/726,217 Notice of Allowance dated Jan. 23, 2020.
U.S. Appl. No. 15/896,572 Office Action dated Dec. 19, 2019.
U.S. Appl. No. 15/896,572 Notice of Allowance dated Apr. 22, 2020.
U.S. Appl. No. 16/598,591 Office Action dated Jul. 21, 2020.
U.S. Appl. No. 15/360,369 Notice of Allowance dated Jul. 5, 2019.
U.S. Appl. No. 16/712,601 Action dated Aug. 19, 2020.
U.S. Appl. No. 16/039,016 Office Action dated Dec. 1, 2020.

* cited by examiner

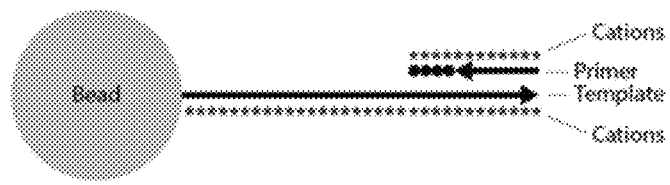
- Template is Linear (Unstructured)
- # Cations is Linearly Related To # Bases
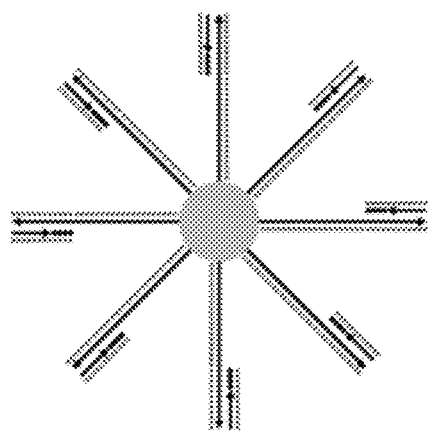
- Multiple Templates Do Not Interact
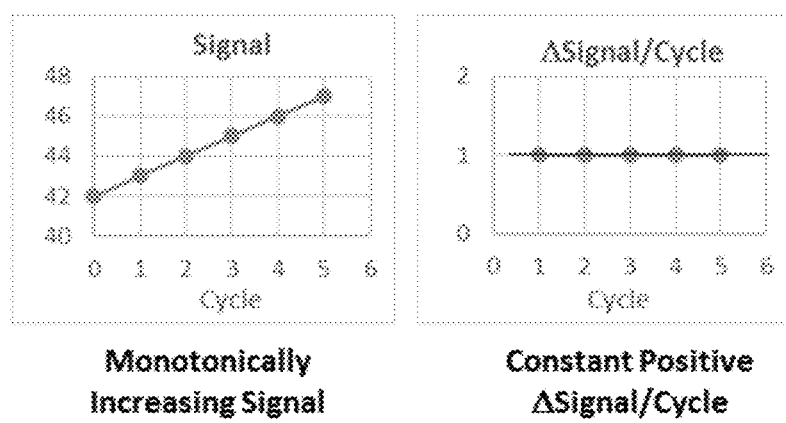
Monotonically Increasing Signal    Constant Positive ΔSignal/Cycle
*FIG. 1*

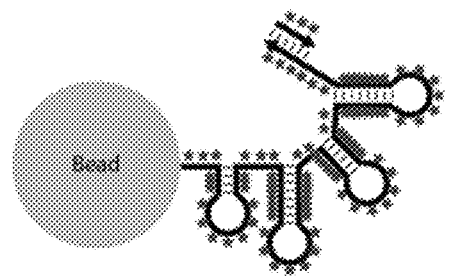
* Template is Nonlinear (Structured)
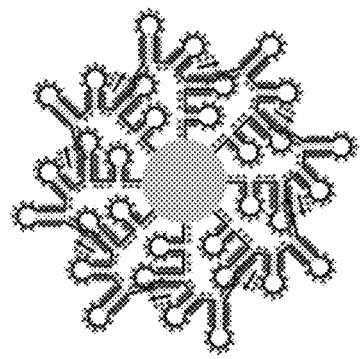
* Multiple Templates Interact
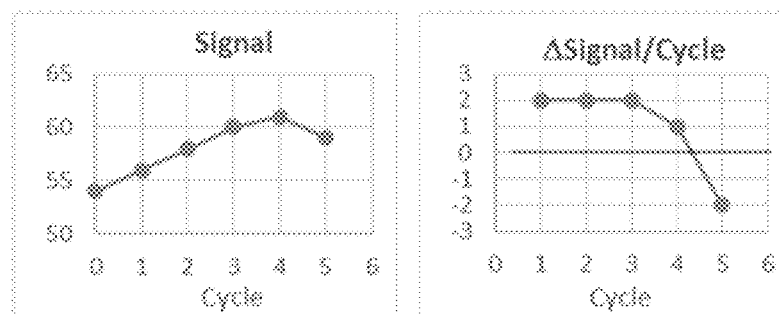
Non-Monotonic Signal     ΔSignal/Cycle Is Positive, Zero, or Negative
*FIG. 2*

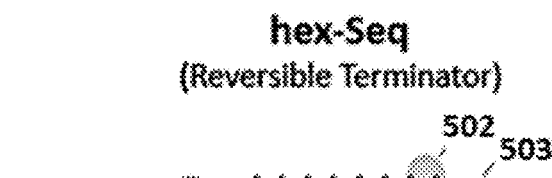
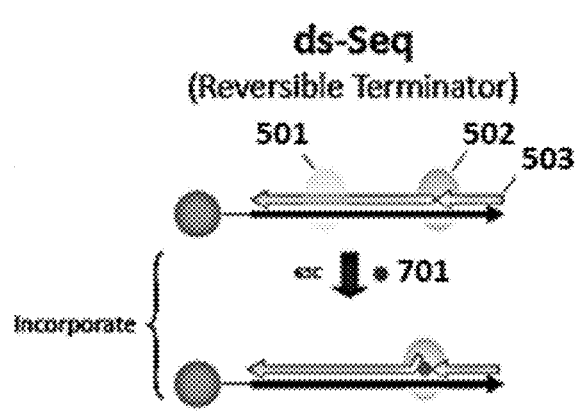
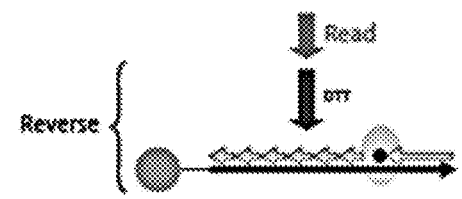
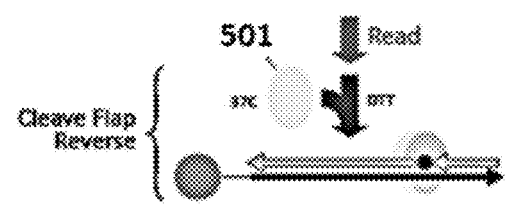
*FIG. 7A*  *FIG. 7B*

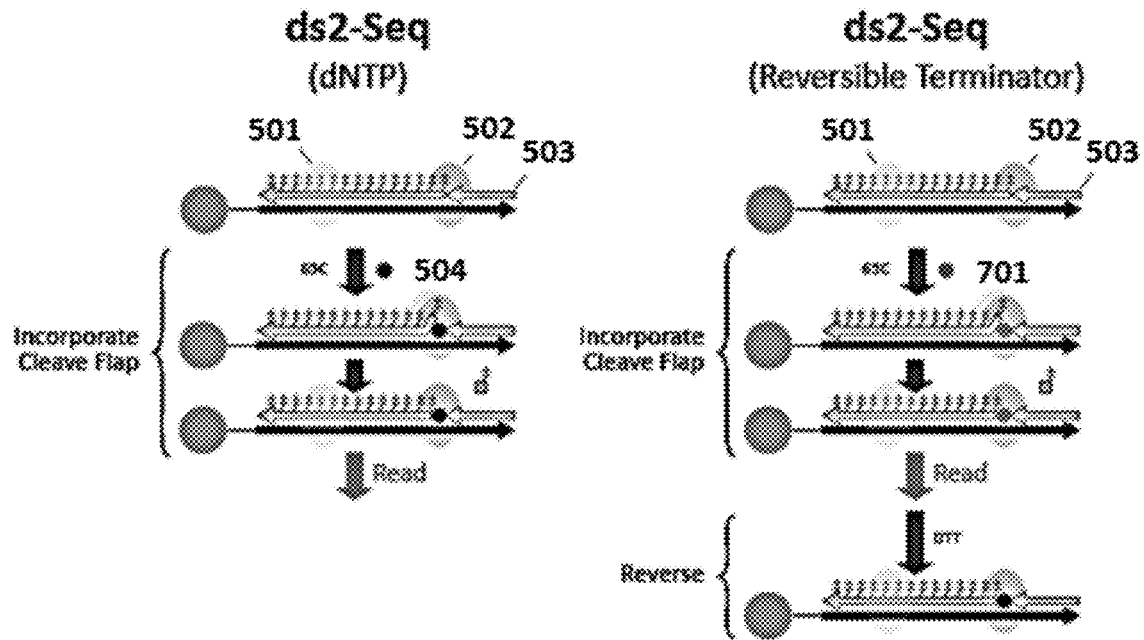
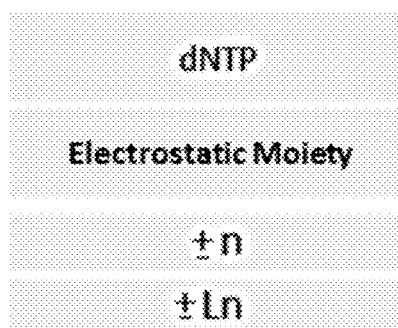
FIG. 11A
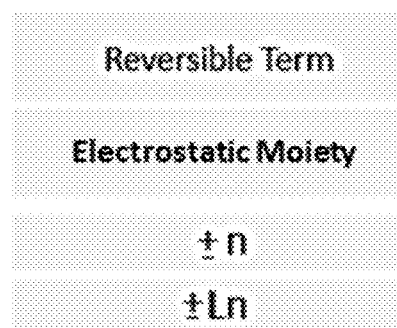
FIG. 11B

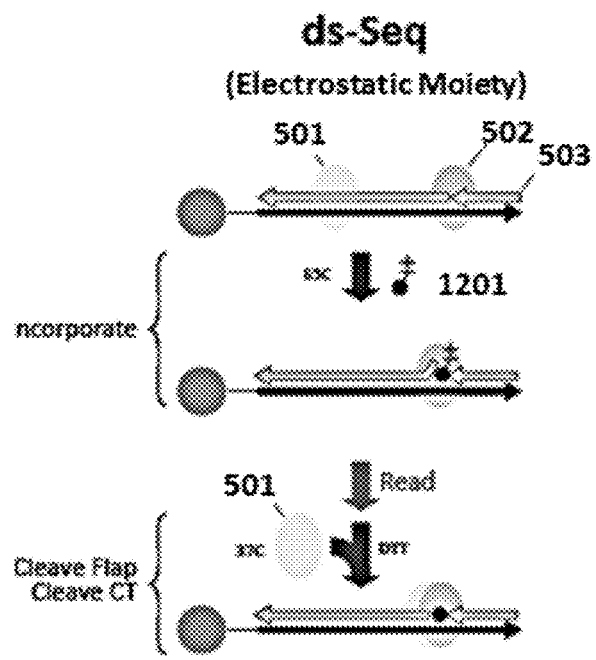
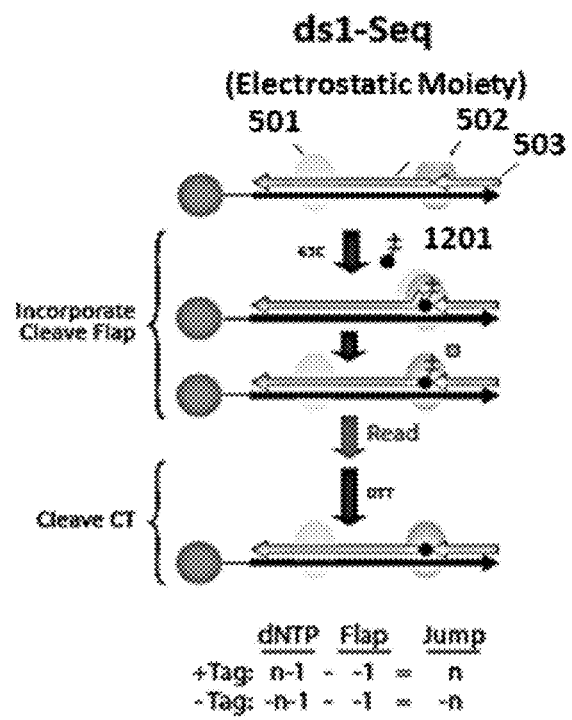
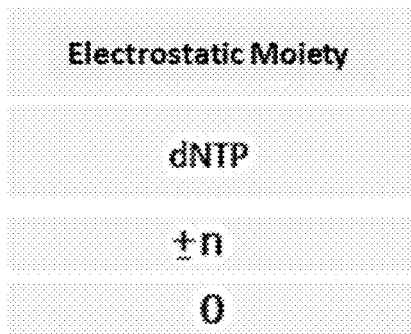
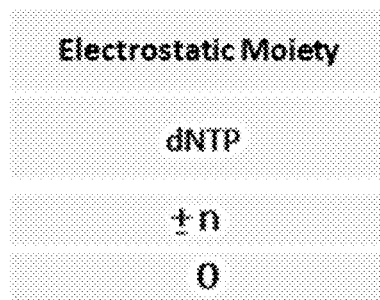
*FIG. 12A*  *FIG. 12B*

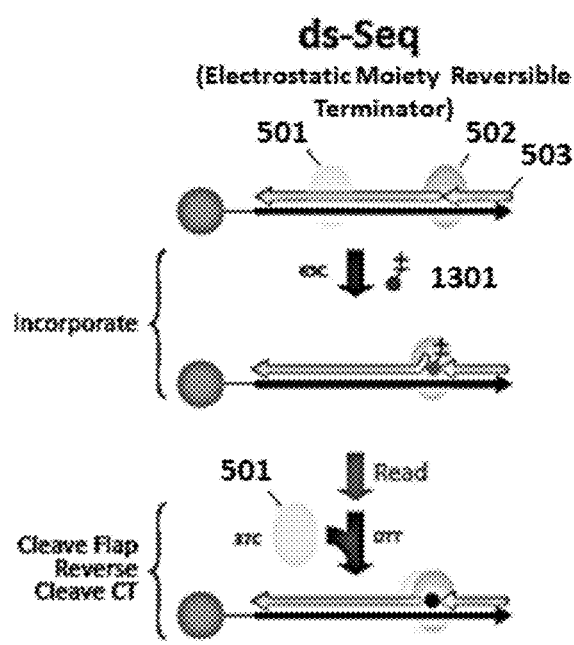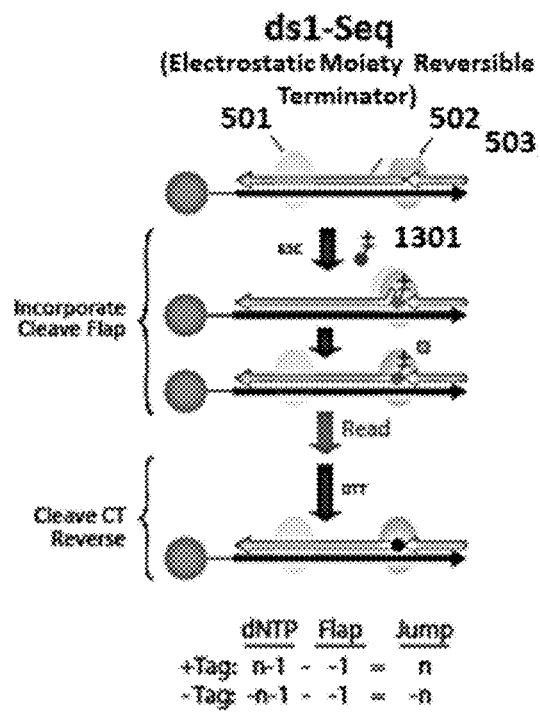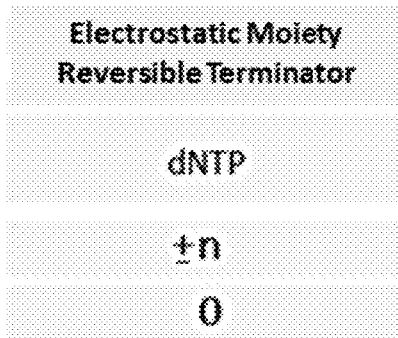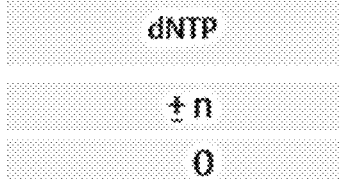
FIG. 13A   FIG. 13B

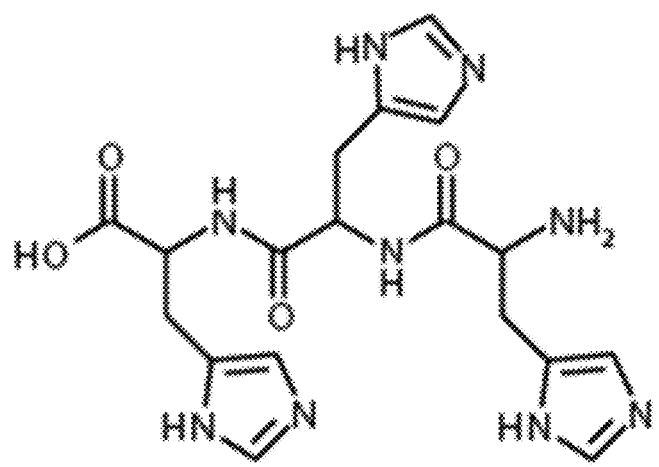
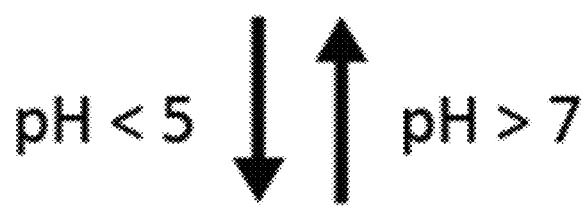
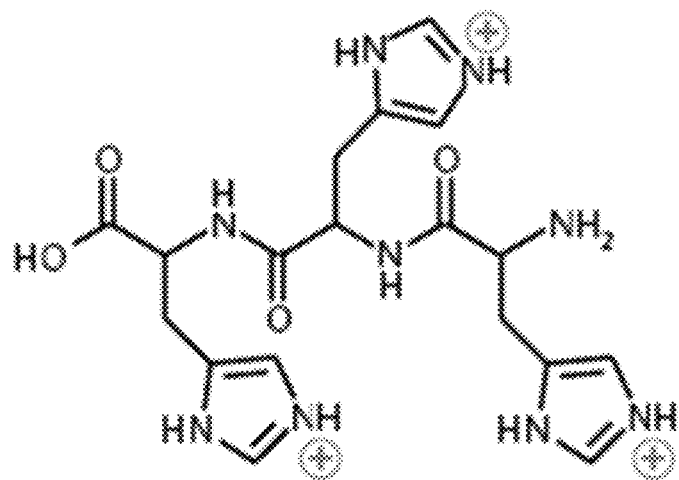
*FIG. 18C*

SYSTEMS AND METHODS FOR NUCLEIC ACID SEQUENCING

CROSS-REFERENCE

This application is a continuation of International Patent Application No. PCT/US2018/52072, filed on Sep. 20, 2018, which claims the benefit of U.S. Provisional Patent Application No. 62/561,358, filed Sep. 21, 2017, and U.S. Provisional Patent Application No. 62/655,083, filed Apr. 9, 2018, each of which is entirely incorporated herein by reference.

SEQUENCE LISTING

The instant application contains a Sequence Listing which has been filed electronically in ASCII format and is hereby incorporated by reference in its entirety. Said ASCII copy, created on Apr. 20, 2020, is named 42808-746_301_SL.txt and is 2,240 bytes in size.

BACKGROUND

The goal to elucidate the entire human genome has created interest in technologies for rapid nucleic acid (e.g., DNA) sequencing, both for small and large scale applications. Important parameters are sequencing speed, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing demand for accurate, high-throughput DNA sequencing that is affordable for clinical applications. Practical methods for determining the base pair sequences of single molecules of nucleic acids, including those with high speed and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment for contagious diseases. Unfortunately, though, existing sequencing technology of the status quo is expensive and may not provide sequence information within a time period and/or at an accuracy that may be sufficient to diagnose and/or treat a subject with a condition.

SUMMARY

The present disclosure provides methods and systems for sample analysis or identification, such as nucleic acid sequencing. The present disclosure provides methods and systems that may enable sample preparation and identification (e.g., sequencing) without the use of particles, such as beads. This may enable a sample to be prepared and identified at substantially reduced cost and complexity as compared to other systems and methods.

In an aspect, the present disclosure provides methods for detecting a nucleic acid molecule, comprising: providing a plurality of double-stranded nucleic acid molecules adjacent to a sensor array, wherein a given double-stranded nucleic acid molecule of the plurality of nucleic acid molecules is disposed adjacent to a given sensor of the sensor array, wherein the given double stranded nucleic acid molecule comprises a first single-stranded nucleic acid molecule and a second single-stranded nucleic acid molecule having sequence complementarity with the first single-stranded nucleic acid molecule, and wherein the given sensor is electrically coupled to a charge double layer comprising the given double-stranded nucleic acid molecule; subjecting at least a portion of the second single-stranded nucleic acid molecule to release from the first single-stranded nucleic acid molecule, to provide a segment of the first single-stranded nucleic acid molecule that is not hybridized to the second single-stranded nucleic acid molecule; bringing the segment in contact with individual nucleotides to subject the segment to a nucleic acid incorporation reaction that generates a third single-stranded nucleic acid molecule from the individual nucleotides, wherein the third single-stranded nucleic acid molecule has sequence complementarity with the first single-stranded nucleic acid molecule; and while conducting the nucleic acid incorporation reaction, using the given sensor to detect signals indicative of incorporation of the individual nucleotides into the third single-stranded nucleic acid molecule, thereby determining a sequence and/or a length of the segment.

In some embodiments, releasing the at least a portion of the second single-stranded nucleic acid molecule forms a flap. In some embodiments, the flap is cleaved from the second single-stranded nucleic acid molecule. In some embodiments, the flap is cleaved after detecting the signals indicative of incorporation of the individual nucleotides. In some embodiments, the flap is cleaved by a flap endonuclease. In some embodiments, the flap endonuclease is mesophilic.

In some embodiments, the second single-stranded nucleic acid molecule is selected from a library of nucleic acid subunits. In some embodiments, the library of nucleic acid subunits comprises random sequences. In some embodiments, a given nucleic acid subunit of the library of nucleic acid subunits comprises at least five nucleotides. In some embodiments, the given nucleic acid subunit of the library of nucleic acid subunits has at least six nucleotides. In some embodiments, the library of nucleic acid subunits comprises peptide nucleic acids or locked nucleic acids.

In some embodiments, the second single-stranded nucleic acid molecule comprises one or more detectable labels. In some embodiments, release of the second single-stranded nucleic acid molecule or a portion thereof from the first single-stranded nucleic molecule generates a detectable signal.

In some embodiments, the plurality of double-stranded nucleic acid molecules is coupled to a plurality of beads. In some embodiments, the given double-stranded nucleic acid molecule is coupled to a given bead of the plurality of beads and the charge double layer is adjacent to a surface of the given bead. In some embodiments, the plurality of double-stranded nucleic acid molecules is coupled to one or more surfaces of the sensor array. In some embodiments, the given double-stranded nucleic acid molecule is coupled to a surface of the given sensor and the charge double layer is adjacent to the surface.

In some embodiments, the method further comprises providing a priming site adjacent to the segment and generating the third single-stranded nucleic acid molecule upon primer extension from the priming site. In some embodiments, the priming site is a primer sequence having sequence complementarity with the first single-stranded nucleic acid molecule. In some embodiments, the method further comprises using a polymerizing enzyme to incorporate the individual nucleotides. In some embodiments, the given sensor comprises at least two electrodes.

In some embodiments, at least a subset of the individual nucleotides comprises a reversible terminator that prevents an additional nucleotide from stably hybridizing to the first single-stranded nucleic acid molecule. In some embodiments, the reversible terminator is removed after incorporation of the individual nucleotide into the third single-stranded nucleic acid molecule and prior to incorporation of another individual nucleotide into the third single-stranded nucleic acid molecule.

In some embodiments, at least a subset of the individual nucleotides includes detectable labels. In some embodiments, the detectable labels are electrostatic moieties. In some embodiments, the detectable labels are coupled to nucleobases of the at least a subset of the individual nucleotides. In some embodiments, the individual nucleotides include different types of nucleotides, each of which different types of nucleotides is reversibly coupled to a single type of detectable label. In some embodiments, the individual nucleotides include different types of nucleotides, each of which different types of nucleotides is reversibly coupled to a different type of detectable label. In some embodiments, the detectable labels are reversibly coupled to the different types of nucleotides by one or more coupling mechanisms. In some embodiments, the detectable labels are reversibly coupled to the different types of nucleotides by a single coupling mechanism. In some embodiments, the detectable labels are removed after detection of the signals indicative of incorporation of the individual nucleotides. In some embodiments, the individual nucleotides include different types of nucleotides and the segment is sequentially brought in contact with the different types of nucleotides.

In some embodiments, at a given time point during the nucleic acid incorporation reaction, the segment is brought in contact with individual nucleotides of a first type, and at a subsequent time point during the nucleic acid incorporation reaction, the segment is brought in contact with individual nucleotides of a second type, wherein the first type is different than the second type. In some embodiments, the individual nucleotides include different types of nucleotides and the segment is simultaneously brought in contact with the different types of nucleotides.

In some embodiments, the signals indicative of incorporation of the individual nucleotides are steady state signals. In some embodiments, the signals indicative of incorporation of the individual nucleotides are detected once after incorporation of an individual nucleotide. In some embodiments, the signals indicative of incorporation of the individual nucleotides are detected at least twice after incorporation of an individual nucleotide. In some embodiments, the signals indicative of incorporation of the individual nucleotides are transient signals. In some embodiments, the signals indicative of incorporation of the individual nucleotides are electrical signals generated by an impedance or impedance change in the charge double layer.

In some embodiments, the plurality of double-stranded nucleic acid molecules is a clonal population of the double-stranded nucleic acid molecules. In some embodiments, the method is repeated until the sequence of the first single-stranded nucleic acid molecule is determined.

In another aspect, the present disclosure provides methods for detecting a nucleic acid molecule, comprising: providing a plurality of single-stranded nucleic acid molecules adjacent to a sensor array, wherein a first single-stranded nucleic acid molecule of the plurality of single-stranded nucleic acid molecules is disposed adjacent to a given sensor of the sensor array, wherein the given sensor is electrically coupled to a charge double layer comprising the first single-stranded nucleic acid molecule; bringing the first single-stranded nucleic acid molecule in contact with individual nucleotides to subject the first single-stranded nucleic acid molecule to a nucleic acid incorporation reaction which generates a second single-stranded nucleic acid molecule from the individual nucleotides, wherein the second single-stranded nucleic acid molecule has sequence complementarity with the first single-stranded nucleic acid molecule, wherein at least a subset of the individual nucleotides comprises detectable labels; and while or subsequent to conducting the nucleic acid incorporation reaction, using the given sensor to detect signals from the detectable labels indicative of incorporation of the individual nucleotides into the second single-stranded nucleic acid molecule, thereby determining a sequence and/or a length of the first single-stranded nucleic acid molecule.

In some embodiments, the plurality of single-stranded nucleic acid molecules is coupled to a plurality of beads. In some embodiments, the first single-stranded nucleic acid molecule is coupled to a given bead of the plurality of beads and the charge double layer is adjacent to a surface of the given bead. In some embodiments, the plurality of single-stranded nucleic acid molecules is coupled to one or more surfaces of the sensor array. In some embodiments, the first single-stranded nucleic acid molecule is coupled to a surface of the given sensor and the charge double layer is adjacent to the surface.

In some embodiments, the method further comprises providing a priming site adjacent to the first single-stranded nucleic acid and generating the second single-stranded nucleic acid molecule upon primer extension from the priming site. In some embodiments, the priming site is a primer sequence having sequence complementarity with the first single-stranded nucleic acid molecule. In some embodiments, the priming site is a self-priming loop. In some embodiments, the method further comprises using a polymerizing enzyme to incorporate the individual nucleotides. In some embodiments, the given sensor comprises at least two electrodes.

In some embodiments, at least another subset of the individual nucleotides comprises a reversible terminator that prevents an additional nucleotide from stably hybridizing to the first single-stranded nucleic acid molecule. In some embodiments, the reversible terminator is removed after incorporation of the individual nucleotide into the second single-stranded nucleic acid molecule and prior to incorporation of another individual nucleotide into the second single-stranded nucleic acid molecule.

In some embodiments, the detectable labels are electrostatic moieties. In some embodiments, the detectable labels are coupled to nucleobases of the at least a subset of the individual nucleotides. In some embodiments, the individual nucleotides include different types of nucleotides, each of which different types of nucleotides is reversibly coupled to a single type of detectable label. In some embodiments, the individual nucleotides include different types of nucleotides, each of which different types of nucleotides is reversibly coupled to a different type of detectable label. In some embodiments, the detectable labels are reversibly coupled to the different types of nucleotides by one or more coupling mechanisms. In some embodiments, the detectable labels are reversibly coupled to the different types of nucleotides by a single coupling mechanism. In some embodiments, the detectable labels are removed after detection of the signals indicative of incorporation of the individual nucleotides.

In some embodiments, the individual nucleotides include different types of nucleotides and the first single-stranded nucleic acid molecule is brought in contact with the different types of nucleotides sequentially. In some embodiments, at a given time point during the nucleic acid incorporation reaction, the first single-stranded nucleic acid molecule is brought in contact with individual nucleotides of a first type, and at a subsequent time point during the nucleic acid incorporation reaction, the first single-stranded nucleic acid molecule is brought in contact with individual nucleotides of a second type, wherein the first type is different than the second type. In some embodiments, the individual nucleotides include different types of nucleotides and the first single-stranded nucleic acid molecule is brought in contact with the different types of nucleotides simultaneously.

In some embodiments, the signals indicative of incorporation of the individual nucleotides are steady state signals. In some embodiments, the signals indicative of incorporation of the individual nucleotides are detected once after incorporation of an individual nucleotide. In some embodiments, the signals indicative of incorporation of the individual nucleotides are detected at least twice after incorporation of an individual nucleotide. In some embodiments, the signals indicative of incorporation of the individual nucleotides are transient signals. In some embodiments, the signals indicative of incorporation of the individual nucleotides are electrical signals generated by an impedance or impedance change in the charge double layer.

In some embodiments, the plurality of single-stranded nucleic acid molecules is a clonal population of the first single-stranded nucleic acid molecules. In some embodiments, the first single-stranded nucleic acid molecule comprises a self-priming loop. In some embodiments, the method is repeated until the sequence of the first single-stranded nucleic acid molecule is determined.

In another aspect, the present disclosure provides methods for detecting a nucleic acid molecule, comprising: providing a plurality of single-stranded nucleic acid molecules adjacent to a sensor array, wherein a first single-stranded nucleic acid molecule of the plurality of single-stranded nucleic acid molecules is disposed adjacent to a given sensor of the sensor array; subjecting the first single-stranded nucleic acid molecule to a nucleic acid incorporation reaction to generate a second single-stranded nucleic acid molecule as a growing strand complementary to the first single-stranded nucleic acid molecule, wherein the nucleic acid incorporation reaction comprises alternately and sequentially (i) incorporating individual nucleotides of a first plurality of nucleotides comprising detectable labels, and (ii) incorporating individual nucleotides of a second plurality of nucleotides that do not comprise detectable labels; and while or subsequent to conducting the nucleic acid incorporation reaction, using the given sensor to detect signals indicative of a change in charge or conductivity from a double layer comprising the detectable labels, thereby determining a sequence and/or a length of the first single-stranded nucleic acid molecule.

In some embodiments, the first plurality of nucleotides comprises a terminator that prevents an additional nucleotide from stably hybridizing to the first single-stranded nucleic acid molecule. In some embodiments, the first plurality of nucleotides comprises dideoxynucleotides. In some embodiments, the second plurality of nucleotides comprises a reversible terminator that prevents an additional nucleotide from stably hybridizing to the first single-stranded nucleic acid. In some embodiments, the reversible terminator is removed after exchanging the individual nucleotides of the first plurality of nucleotides with the individual nucleotides of the second plurality of nucleotides.

In some embodiments, the first plurality of nucleotides is exchanged with the second plurality of nucleotides. In some embodiments, the incorporation of the second plurality of nucleotides corrects phase error by incorporating an individual nucleotide from the second plurality of nucleotides at a location along the first single-stranded nucleic acid molecule in which an individual nucleotide from the first plurality of nucleotides has not been incorporated. In some embodiments, the method further comprises continuing the nucleic acid incorporation reaction using the individual nucleotides from the first plurality of nucleotides.

In some embodiments, the detectable labels are not removable. In some embodiments, the detectable labels are electrostatic moieties. In some embodiments, the detectable labels are coupled to nucleobases of the individual nucleotides of the first plurality of nucleotides. In some embodiments, the individual nucleotides of the first plurality of nucleotides include different types of nucleotides, each of which different types of nucleotides is coupled to a single type of detectable label. In some embodiments, the individual nucleotides of the first plurality of nucleotides include different types of nucleotides, each of which different types of nucleotides is coupled to a different type of detectable label.

In some embodiments, the given sensor is electrically coupled to a charge double layer comprising the first single-stranded nucleic acid molecule. In some embodiments, the plurality of single-stranded nucleic acid molecules is coupled to a plurality of beads. In some embodiments, the first single-stranded nucleic acid molecule is coupled to a given bead of the plurality of beads and the charge double layer is adjacent to a surface of the given bead. In some embodiments, the plurality of single-stranded nucleic acid molecules is coupled to one or more surfaces of the sensor array. In some embodiments, the first single-stranded nucleic acid molecule is coupled to a surface of the given sensor and the charge double layer is adjacent to the surface.

In some embodiments, the method further comprises providing a priming site adjacent to the first single-stranded nucleic acid and generating the second single-stranded nucleic acid molecule upon primer extension from the priming site. In some embodiments, the priming site is a primer sequence having sequence complementarity with the first single-stranded nucleic acid molecule. In some embodiments, the priming site is a self-priming loop. In some embodiments, the method further comprises using a polymerizing enzyme to incorporate the individual nucleotides.

In some embodiments, the given sensor comprises at least two electrodes. In some embodiments, the individual nucleotides include different types of nucleotides and the first single-stranded nucleic acid molecule is brought in contact with the different types of nucleotides sequentially. In some embodiments, at a given time point during the nucleic acid incorporation reaction, the first single-stranded nucleic acid molecule is brought in contact with individual nucleotides of a first type, and at a subsequent time point during the nucleic acid incorporation reaction, the segment is brought in contact with individual nucleotides of a second type, wherein the first type is different than the second type. In some embodiments, the individual nucleotides include different types of nucleotides and the first single-stranded nucleic acid molecule is brought in contact with the different types of nucleotides simultaneously.

In some embodiments, the signals indicative of incorporation of the individual nucleotides are steady state signals. In some embodiments, the signals indicative of incorporation of the individual nucleotides are detected once after incorporation of an individual nucleotide. In some embodiments, the signals indicative of incorporation of the individual nucleotides are detected at least twice after incorporation of an individual nucleotide. In some embodiments, the signals indicative of incorporation of the individual nucleotides are transient signals. In some embodiments, the signals indicative of incorporation of the individual nucleotides are electrical signals generated by an impedance or impedance change in the charge double layer.

In some embodiments, the plurality of single-stranded nucleic acid molecules is a clonal population of the first single-stranded nucleic acid molecules. In some embodiments, the method is repeated until the sequence of the first single-stranded nucleic acid molecule is determined. In some embodiments, the first single-stranded nucleic acid molecule is part of the plurality of single-stranded nucleic acid molecules adjacent to the given sensor, wherein individual single-stranded nucleic acid molecules of the plurality of single-stranded nucleic acid molecules, including the first single-stranded nucleic acid molecule, have sequence homology to a template single-stranded nucleic acid molecule.

In another aspect, the present disclosure provides systems for detecting a nucleic acid molecule, comprising: a sensor array comprising a plurality of sensors, wherein during use, a given double-stranded nucleic acid molecule of a plurality of double-stranded nucleic acid molecules is disposed adjacent to a given sensor of the sensor array, wherein the given double-stranded nucleic acid molecule comprises a first single-stranded nucleic acid molecule and a second single-stranded nucleic acid molecule having sequence complementarity with the first single-stranded nucleic acid molecule, wherein the given sensor is electrically coupled to a charge double layer comprising the given double-stranded nucleic acid molecule; and one or more computer processors operatively coupled to the sensor array, wherein the one or more computer processors are individually or collectively programmed to (i) bring a segment of the first-single stranded nucleic acid molecule that is not hybridized to the second single-stranded nucleic acid molecule in contact with individual nucleotides to subject the segment to a nucleic acid incorporation reaction that generates the third single-stranded nucleic acid molecule from the individual nucleotides, wherein the third single-stranded nucleic acid molecule has sequence complementarity with the first single-stranded nucleic acid molecule, and (ii) while or subsequent to conducting the nucleic acid incorporation reaction, use the given sensor to detect signals indicative of incorporation of the individual nucleotides into the third single-stranded nucleic acid molecule, thereby determining a sequence and/or a length of the segment.

In some embodiments, during use, the plurality of double-stranded nucleic acid molecules is coupled to a plurality of beads. In some embodiments, during use, the given double-stranded nucleic acid molecule is coupled to a given bead of the plurality of beads and the charge double layer is adjacent to a surface of the given bead. In some embodiments, during use, the plurality of double-stranded nucleic acid molecules is coupled to one or more surfaces of the sensor array. In some embodiments, during use, the given double-stranded nucleic acid molecule is coupled to a surface of the given sensor and the charge double layer is adjacent to the surface. In some embodiments, the given sensor comprises at least two electrodes.

In some embodiments, during use, the signals indicative of incorporation of the individual nucleotides are steady state signals. In some embodiments, the signals indicative of incorporation of the individual nucleotides are detected once after incorporation of an individual nucleotide. In some embodiments, the individual nucleotide incorporates detectable labels. In some embodiments, the detectable labels are electrostatic moieties. In some embodiments, the signals indicative of incorporation of the individual nucleotides are detected at least twice after incorporation of an individual nucleotide. In some embodiments, during use, the signals indicative of incorporation of the individual nucleotides are transient signals. In some embodiments, during use, the signals indicative of incorporation of the individual nucleotides are electrical signals generated by an impedance or impedance change in the charge double layer.

In another aspect, the present disclosure provides systems for detecting a nucleic acid molecule, comprising: a sensor array comprising a plurality of sensors, wherein during use a first single-stranded nucleic acid molecule of a plurality of single-stranded nucleic acid molecules is disposed adjacent to a given sensor of the sensor array, wherein the given sensor is electrically coupled to a charge double layer comprising the first single-stranded nucleic acid molecule; and one or more computer processors operatively coupled to the sensor array, wherein the one or more computer processors are individually or collectively programmed to (i) bring the first single-stranded nucleic acid molecule in contact with individual nucleotides to subject the first single-stranded nucleic acid molecule to a nucleic acid incorporation reaction which generates a second single-stranded nucleic acid molecule from the individual nucleotides, wherein the second single-stranded nucleic acid molecule has sequence complementarity with the first single-stranded nucleic acid molecule, wherein at least a subset of the individual nucleotides comprises detectable labels, and (ii) while or subsequent to conducting the nucleic acid incorporation reaction, using the given sensor to detect signals from the detectable labels indicative of incorporation of the individual nucleotides into the second single-stranded nucleic acid molecule, thereby determining a sequence and/or a length of the first single-stranded nucleic acid molecule.

In some embodiments, during use, the plurality of single-stranded nucleic acid molecules is coupled to a plurality of beads. In some embodiments, during use, the first single-stranded nucleic acid molecule is coupled to a given bead of the plurality of beads and the charge double layer is adjacent to a surface of the given bead. In some embodiments, during use, the plurality of single-stranded nucleic acid molecules is coupled to one or more surfaces of the sensor array. In some embodiments, during use, the first single-stranded nucleic acid molecule is coupled to a surface of the given sensor and the charge double layer is adjacent to the surface. In some embodiments, the given sensor comprises at least two electrodes. In some embodiments, the detectable labels are electrostatic moieties.

In some embodiments, during use, the signals indicative of incorporation of the individual nucleotides are steady state signals. In some embodiments, the signals indicative of incorporation of the individual nucleotides are detected once after incorporation of the individual nucleotide. In some embodiments, the signals indicative of incorporation of the individual nucleotides are detected at least twice after incorporation of the individual nucleotide. In some embodiments, during use, the signals indicative of incorporation of the individual nucleotides are transient signals. In some embodiments, during use, the signals indicative of incorporation of the individual nucleotides are electrical signals generated by an impedance or impedance change in the charge double layer.

In another aspect, the present disclosure provides systems for detecting a nucleic acid molecule, comprising: a sensor array comprising a plurality of sensors, wherein during use a first single-stranded nucleic acid molecule of a plurality of single-stranded nucleic acid molecules is disposed adjacent to a given sensor of the sensor array; and one or more computer processors operatively coupled to the sensor array, wherein the one or more computer processors are individually or collectively programmed to (i) bring the first single-stranded nucleic acid molecule in contact with individual nucleotides to subject the first single-stranded nucleic acid molecule to a nucleic acid incorporation reaction to generate a second single-stranded nucleic acid molecule, wherein the nucleic acid incorporation reaction comprises alternately and sequentially incorporating individual nucleotides of a first plurality of nucleotides comprising detectable labels and exchanging the individual nucleotides of the first plurality of nucleotides with individual nucleotides of a second plurality of nucleotides that do not comprise detectable labels and (ii) while or subsequent to conducting the nucleic acid incorporation reaction, using the given sensor to detect signals indicative of a change in charge or conductivity from a double layer comprising the detectable labels, thereby determining a sequence and/or a length of the first single-stranded nucleic acid molecule.

In some embodiments, during use, the given sensor is electrically coupled to a charge double layer comprising the first single-stranded nucleic acid molecule. In some embodiments, during use, the plurality of single-stranded nucleic acid molecules is coupled to a plurality of beads. In some embodiments, during use, the first single-stranded nucleic acid molecule is coupled to a given bead of the plurality of beads and the charge double layer is adjacent to a surface of the given bead. In some embodiments, during use, the plurality of single-stranded nucleic acid molecules is coupled to one or more surfaces of the sensor array. In some embodiments, during use, the first single-stranded nucleic acid molecule is coupled to a surface of the given sensor and the charge double layer is adjacent to the surface. In some embodiments, the given sensor comprises at least two electrodes. In some embodiments, the detectable labels are electrostatic moieties.

In some embodiments, during use, the signals indicative of incorporation of the individual nucleotides are steady state signals. In some embodiments, the signals indicative of incorporation of the individual nucleotides are detected once after incorporation of an individual nucleotide. In some embodiments, the signals indicative of incorporation of the individual nucleotides are detected at least twice after incorporation of an individual nucleotide. In some embodiments, during use the signals indicative of incorporation of the individual nucleotides are transient signals. In some embodiments, during use the signals indicative of incorporation of the individual nucleotides are electrical signals generated by an impedance or impedance change in the charge double layer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1 shows a model illustration of unstructured template nucleic acid molecules coupled to a bead;

FIG. 2 shows a model illustration of structured template nucleic acid molecules coupled to a bead;

FIG. 4A shows an example comparison between single-stranded and double-stranded sequencing results; FIG. 4B shows example sequencing results of double-stranded sequencing using polyanion electrostatic moieties; FIG. 4C shows example sequencing results of double-stranded sequencing using polycation electrostatic moieties; FIG. 4D shows example sequencing results of double-stranded sequencing using both polyanion and polycation electrostatic moieties;

FIGS. 7A and 7B show example methods for double-stranded sequencing with reversible terminators; FIG. 7A shows an example method for double-stranded sequencing using reversible terminators and flap endonucleases; FIG. 7B shows an example method for double-stranded sequencing using reversible terminators and nucleic acid subunits;

FIGS. 11A and 11B show example methods for double-stranded sequencing using detectable labels on the second single-stranded nucleic acid molecule; FIG. 11A shows an example sequencing method using detectable labels that are cleaved by a flap endonuclease; FIG. 11B shows an example sequencing method using detectable labels and reversible terminators;

FIGS. 12A and 12B shows example methods for double-stranded sequencing using detectable labels and flap endonucleases; FIG. 12A shows an example method for double-stranded sequencing using detectable labels and a mesophilic flap endonuclease; FIG. 12B shows an example method for double-stranded sequencing using detectable labels and a thermostable flap endonuclease;

FIGS. 13A and 13B shows example methods for double-stranded sequencing method using detectable labels, a flap endonuclease, and reversible terminators; FIG. 13A shows an example method for double-stranded sequencing using detectable labels, a mesophilic flap endonuclease, and reversible terminators; FIG. 13B shows an example method for double-stranded sequencing using detectable labels, a thermostable flap endonuclease, and reversible terminators;

FIGS. 18A-C show examples of detectable labels; FIG. 18A shows an example of a polycation electrostatic moiety with a lysine residue; FIG. 18B shows an example of a polyanion electrostatic moiety with a carboxylic acid group; FIG. 18C shows an example of a switch label comprising histidine imidazole residues that can switch between a neutral state and a positive state in response to pH of the buffer;

DETAILED DESCRIPTION

Figure 3:
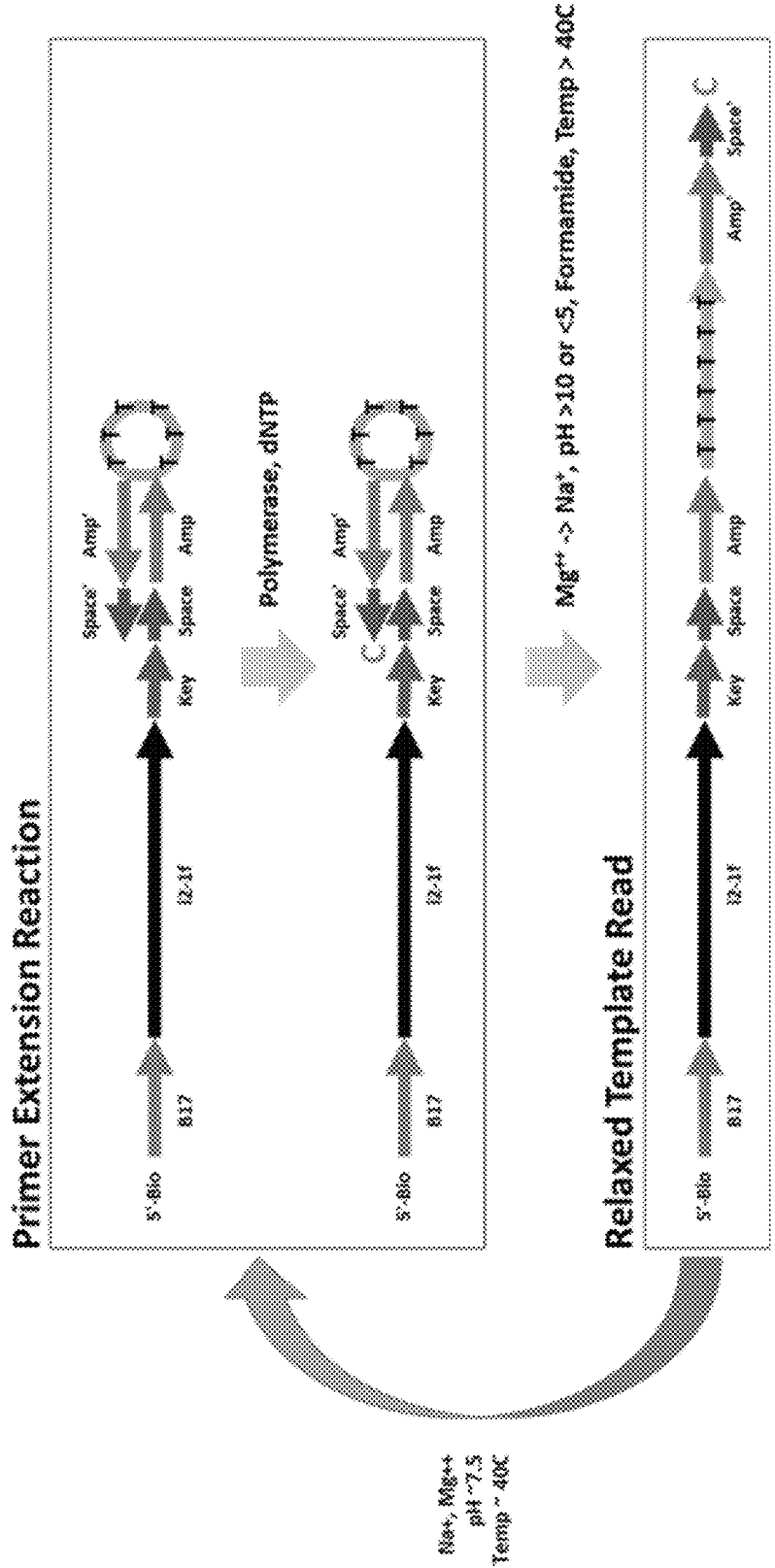
FIG. 3 shows an example process flow for relaxed template sequencing.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "adjacent to," as used herein, generally refers to next to, in proximity to, or in sensing or electronic vicinity (or proximity) of. For example, a first object adjacent to a second can be in contact with the second object, or may not be in contact with the second object but may be in proximity to the second object. In some examples, a first object to a second object is within about 0 micrometers ("microns"), 0.001 microns, 0.01 microns, 0.1 microns, 0.2 microns, 0.3 microns, 0.4 microns, 0.5 microns, 1 microns, 2 microns, 3 microns, 4 microns, 5 microns, 10 microns, or 100 microns of the second object.

The term "nucleic acid," as used herein, generally refers to a molecule comprising one or more nucleic acid subunits. A nucleic acid may include one or more subunits selected from adenosine (A), cytosine (C), guanine (G), thymine (TO, and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid molecule is circular.

The terms "nucleic acid molecule," "nucleic acid sequence," "nucleic acid fragment," "oligonucleotide," "oligo," and "polynucleotide," as used herein, generally refer to a polymeric form of nucleotides that may have various lengths, either deoxyribonucleotides (DNA) or ribonucleotides (RNA), or analogs thereof. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may include one or more non-standard nucleotide(s), nucleotide analog(s) and/or modified nucleotides. In some cases, an oligo may refer to a short single-stranded nucleic acid sequence with at most 300 base pairs (bp), at most 200 bp, at most 100 bp, at most 90 bp, at most 80 bp, at most 70 bp, at most 60 bp, at most 50 bp, at most 40 bp, at most 30 bp, at most 20 bp, at most 10 bp or less. In some cases, an oligo may have a —C6-NH$_2$ functional group at its 3' or 5' end suitable for conjugation.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, 2,6-diaminopurine or the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012).

The term "nucleotide," as used herein, generally refers to an organic molecule that serves as the monomer, or subunit, of a nucleic acid molecule, such as a deoxyribonucleic (DNA) molecule or ribonucleic acid (RNA) molecule. In some embodiments, a nucleotide may also be a peptide nucleic acid (PNA) nucleotide, a locked nucleic acid (LNA) nucleotide, or a dideoxynucleotide.

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "polymerizing enzyme," as used herein, generally refers to any enzyme capable of catalyzing a polymerization reaction. Examples of polymerases include, without limitation, a nucleic acid polymerase. The polymerase can be naturally occurring or synthesized. An example polymerase is a Φ29 polymerase or derivative thereof. A polymerase can be a polymerization enzyme. In some cases, a transcriptase or a ligase is used (i.e., enzymes which catalyze the formation of a bond). Examples of polymerases include a DNA polymerase, and RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, or variants, modified products and derivatives thereof. In some embodiments, the polymerase is a single subunit polymerase. The polymerase can have high processivity, namely the capability of the polymerase to consecutively incorporate nucleotides in a nucleic acid template without releasing the nucleic acid template.

The term "detectable label," as used herein, generally refers to any detectable moiety that is coupled to a molecule to be detected. Non-limiting examples of detectable labels may include electrostatic moieties, fluorescence moieties, chemiluminescence moieties, radio moieties, colorimetric moieties, or any combination thereof. Detectable labels may be reversibly or irreversibly coupled to a molecule to be detected. Such moieties may be labels. Examples of electrostatic moieties include charge labels. Detectable labels may be coupled to a nucleobase at a C5 or C7 position. For example, a reversible electrostatic moiety may be coupled to a nucleotide that is incorporated into a nucleic acid molecule.

Figure 17:
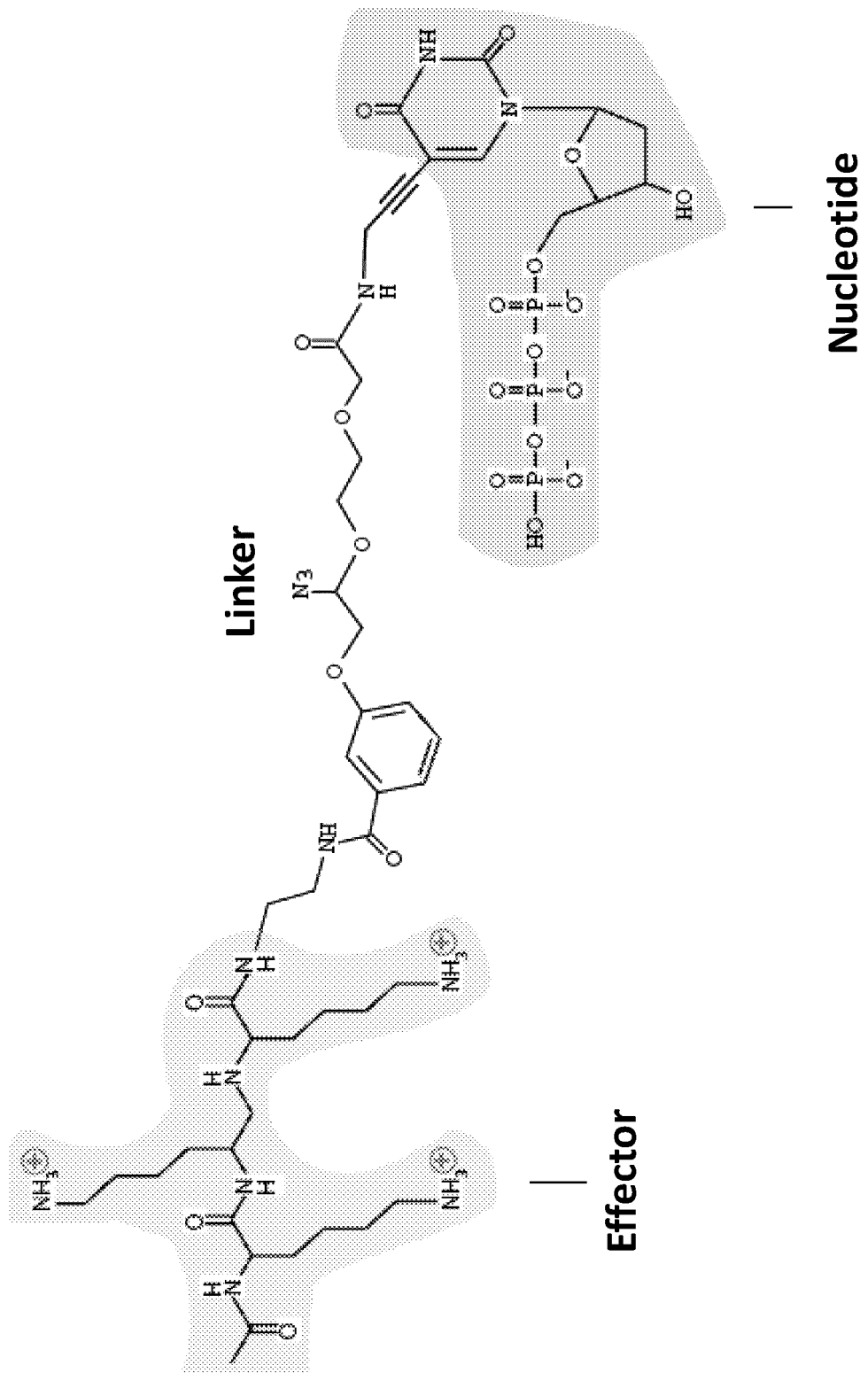
FIG. 17 shows an example of a modified nucleotide comprising a detectable label or effector coupled to a nucleobase via a linker.

A detectable label may be coupled to a nucleobase via a linker. A linker may be coupled to a nucleobase at a C5 or C7 position. The linker may be a non-nucleotide molecule. The linker may be acid labile, photolabile or contain a disulfide linkage. The linker may hold the detectable label at a sufficient distance from the nucleotide so as not to interfere with any interaction between the nucleotide and an enzyme. In some examples, the detectable linker is at a distance of at least about 1 nanometer (nm), 2 nm, 3 nm, 4 nm, 5 nm, 10 nm, 20 nm, 30 nm, 40 nm, 50 nm, 100 nm, 200 nm, 300 nm, 400 nm, 500 nm, or greater from the nucleotide. FIG. 17 shows an example of a modified nucleotide with a detectable label coupled to a nucleotide via a linker. In this example, the detectable label may also be referred to as an effector molecule since the detectable label may affect the charge distribution around the nucleotide.

The term "electrostatic moiety," as used herein, generally refers to a detectable label comprising a net positive or negative charge, or a moiety attached to a chemical or biological unit that renders the chemical or biological unit detectable. For example, an electrostatic moiety may include a charged functional group, a part of a functional group having a charge, a charge label, or a charged molecule as a detectable label. The electrostatic moiety may be monovalent (e.g., have a +1 or −1 charge) or polyvalent (e.g., have a +2, +3, +4, +5, +6, etc. or −1, −2, −3, −4, −5, −6, etc. charge). The electrostatic moiety may have a net positive charge or a negative charge. The electrostatic moiety may have one or more anionic or cationic charge groups. In an example, the electrostatic moiety has both anionic and cationic charge groups and a net positive or negative charge. In another example, the electrostatic moiety is not a zwitterion. The electrostatic moiety may have a constant net charge or may change charge. In an example, the electrostatic moiety switches or changes charge as a function of solution conditions (e.g., pH, temperature, etc.).

The term "clonal," as used herein, generally refers to at least some, substantially all, or all, of the populations of a sensor area being of the same nucleic acid sequence. There may be two population associated with a single sample nucleic acid fragment, as may be used for "mate pairs," "paired ends", or other similar methodologies; the populations may be present in roughly similar numbers in the sensor area, and may be randomly distributed over the sensor area.

The term "phase error," as used herein, generally refers to an error or difference between a given polynucleotide sequence (e.g., second or third single-stranded nucleic acid molecule) and a template nucleic acid molecule from which the given polynucleotide sequence is derived. The given polynucleotide sequence may be a part of a clonal population and the given nucleotide sequence may have a longer or shorter sequence than the consensus state (e.g., reference sequence) of the clonal population. A phase error may be a leading or a lagging phase error. A leading phase error may include additional nucleotide bases that are not present in the consensus (e.g., reference) sequence. A lagging phase error may include fewer nucleotide bases relative to the consensus (e.g., reference) sequence. Phase error may be a product of misincorporation or lack of incorporation of nucleotide bases by a polymerizing enzyme. Phase error may limit the read length of a sequencing system.

The term "flap," as used herein, generally refers to a portion of a single-stranded nucleic acid molecule that is not hybridized or associated with another single-stranded nucleic acid molecule while a portion of the single-stranded nucleic acid molecule is hybridized or associated with the other single-stranded nucleic acid molecule. A flap may be at least about 1, 2, 3, 4, 5, 6, 8, 10, 12, 15, 20, 30, 40, 50 or more nucleotide bases in length.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Methods for Nucleic Acid Sequencing

In an aspect, the present disclosure provides a method for nucleic acid sequencing. The method may comprise providing a plurality of double-stranded nucleic acid molecules adjacent to a sensor array. A given, or individual, double-stranded nucleic acid molecule may be disposed adjacent to a given, or individual, sensor of the sensor array. The double-stranded nucleic acid molecule may comprise a first single-stranded nucleic acid molecule and a second-single stranded nucleic acid molecule. The first and second single-stranded nucleic acid molecules may have sequence complementarity with one another. The sensor may be electrically coupled to a charge double layer (e.g., within a Debye length) of the double-stranded nucleic acid molecule. A portion of the second single-stranded nucleic acid molecule may be released from the first single-stranded nucleic acid molecule to provide a segment of the first single-stranded nucleic acid molecule that is not hybridized to the second single-stranded nucleic acid molecule. The segment may be brought in contact with an individual nucleotide. The individual nucleotide may be subject to a nucleic acid incorporation reaction that generates a third single-stranded nucleic acid molecule. The third single-stranded nucleic acid molecule may have sequence complementarity with the first single-stranded nucleic acid molecule. During the nucleic acid incorporation reaction, the sensor may be used to detect signals indicative of incorporation of the individual nucleotides into the third single-stranded nucleic acid molecule, thereby determining a sequence or a length of the non-hybridized segment.

In another aspect, the present disclosure may provide methods for detecting a nucleic acid molecule. The method may comprise providing a plurality of single-stranded nucleic acid molecules adjacent to a sensor array, bringing the first single-stranded nucleic acid molecule in contact with individual nucleotides to subject the first single-stranded nucleic acid molecule to a nucleic acid incorporation reaction which generates a second single-stranded nucleic acid molecule from the individual nucleotides, and while or subsequent to conducting the nucleic acid incorporation reaction, using the given sensor to detect signals from the detectable labels indicative of incorporation of the individual nucleotides into the second single-stranded nucleic acid molecule, thereby determining a sequence and/or a length of the first single-stranded nucleic acid molecule. A first single-stranded nucleic acid molecule of the plurality of single-stranded nucleic acid molecules may be disposed adjacent to a given sensor of the sensor array. The given sensor may be electrically coupled to a charge double layer (e.g., within a Debye length) of the first single-stranded nucleic acid molecule. The second single-stranded nucleic acid molecule may have sequence complementarity with the first single-stranded nucleic acid molecule. At least a subset of the individual nucleotides may comprise detectable labels.

In another aspect, the present disclosure may provide methods for nucleic acid sequencing. The methods may comprise providing a plurality of single-stranded nucleic acid molecules adjacent to a sensor array, subjecting the first single-stranded nucleic acid molecule to a nucleic acid incorporation reaction to generate a second single-stranded nucleic acid molecule as a growing strand complementary to the first single-stranded nucleic acid molecule, and while or subsequent to conducting the nucleic acid incorporation reaction, using the given sensor to detect signals from the detectable labels indicative of incorporation of the individual nucleotides of the first plurality of nucleotides into the second single-stranded nucleic acid molecule, thereby determining a sequence or a length of the first single-stranded nucleic acid molecule. A first single-stranded nucleic acid molecule of the plurality of single-stranded nucleic acid molecules may be disposed adjacent to a given sensor of the sensor array. The nucleic acid incorporation reaction may comprise alternately and sequentially (i) incorporating individual nucleotides of a first plurality of nucleotides comprising detectable labels, and (ii) incorporating individual nucleotides of a second plurality of nucleotides that do not comprise detectable labels.

The systems and methods described herein may be used to detect biological molecules and reactions. For example, the systems and methods described may be used to detect binding events, reactions and reaction products, and/or the presence or absence of biological molecule. In an example the systems and methods may be used to determine a sequence of a nucleic acid molecule. In another example, the systems and methods may be used to determine a length (e.g., the number of nucleotides) of a nucleic acid molecule. In an example, the systems and method may be used to determine both a sequence and a length of a target nucleic acid molecule. The systems and methods may be used to detect nucleic acid polymorphisms such as, but not limited to, misincorporated nucleotides, changes in fragment size, repeated nucleotide sequences, and/or deleted nucleotide sequences. Determining a length of a nucleic acid molecule may have applications for healthcare, such as diagnostics (e.g., cancer detection). For example, the systems and methods may be used to detect microsatellite instability by detecting increases in fragment length.

Sequencing or determining a length of nucleic acid molecules may utilize nucleic acid templates free in solution or coupled to a support. The support may include a bead, planar surface, well, or any other structure capable of coupling to a nucleic acid molecule. The support may be positioned near a sensor of a sensor array. Alternatively, or in addition to, the support may be a part of a sensor of a sensor array (e.g., an electrode, passivation layer, dielectric layer, etc.). The nucleic acid template coupled to the support may be unstructured (e.g., extend linearly from the support surface) or may be structured (e.g., form loops, hairpins, and/or other secondary structure). FIG. 1 shows an example of an unstructured nucleic acid template coupled to a bead. The bead may be coupled to a single nucleic acid template or coupled to multiple nucleic acid templates. The unstructured templates may not interact with one another around the surface of the bead. Alternatively, or in addition to, the unstructured nucleic acid templates may interact with each other around the surface of the bead. Nucleic acid templates that do not interact may generate monotonic signals (e.g., each nucleotide incorporated generates a constant signal) during sequencing. FIG. 2 shows an example of a structured nucleic acid template coupled to a bead. The nucleic acid template may interact with itself to form loops, hairpins, and/or other secondary structures. The bead may have a single nucleic acid template or multiple nucleic acid templates coupled to it. In an example, the bead is coupled to multiple nucleic acid templates and the nucleic acid templates may interact with each other. Nucleic acid templates that interact with each other may generate non-monotonic signals (e.g., each nucleotide incorporated generates a different, non-linear signal) during sequencing.

Structured nucleic acid templates may be unstructured or relaxed prior to sequencing to generate monotonic signals. The template structure may be relaxed prior to nucleotide incorporation (e.g., a primer extension reaction) or prior to reading or detecting an incorporation event. FIG. 3 shows an example method for relaxed template sequencing. The structured template may include random coils, secondary structure, and/or hairpins. In an example, the template includes a self-priming loop. The self-priming loop may be a hairpin structure that permits the single-stranded nucleic acid structure to be extended without a separate primer sequence. In the structured state, the self-priming loop may be arranged to facilitate a primer extension reaction through Loop-mediated amplification (LAMP). The self-priming loop may facilitate the incorporation of a nucleotide into the 3-prime end of the nucleic acid template. Alternatively, or in addition to, the self-priming loop may incorporate a nucleotide into the 5-prime end of the nucleic acid template. After incorporation of a nucleotide, the structure of the nucleic acid template may be relaxed. The template structure may be relaxed by altering the solution conditions, including, but not limited to, applying heat, altering the pH, altering the ionic strength, and/or introducing one or more organic solvents (e.g., formamide or urea) to the solution. The relaxed nucleic acid template may then be read to detect the nucleotide incorporation. The detected signal may be a linear, or monotonic, signal.

Figure 4A:
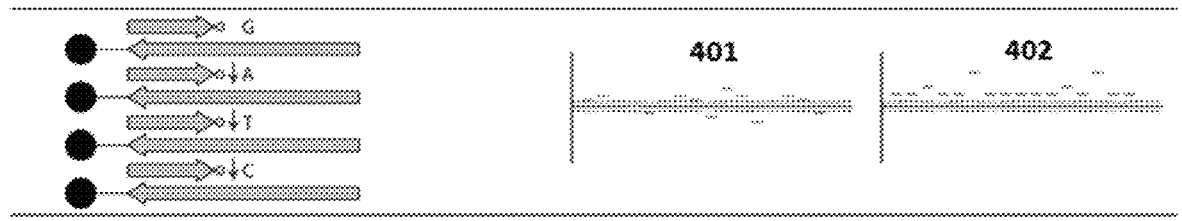
FIGS. 4A-4D show examples of double-stranded sequencing methods and sequencing results using labeled and non-labeled nucleotides.
Figure 4B:
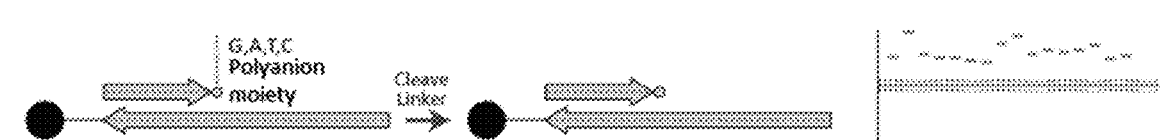
Figure 4C:
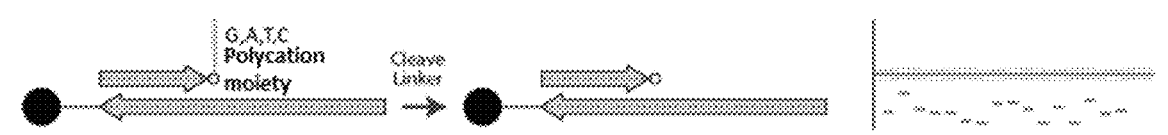
Figure 4D:
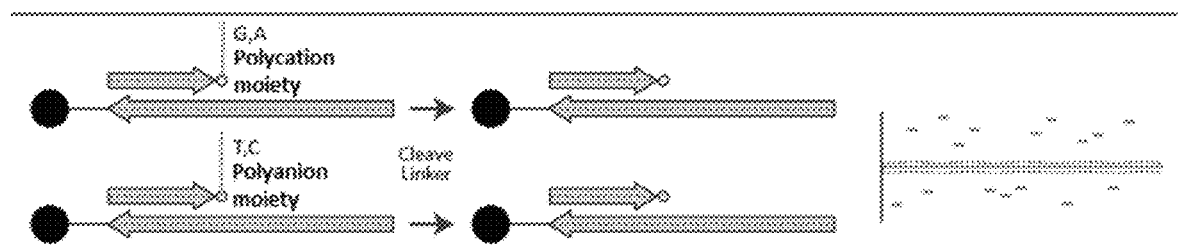

Signal linearity may be increased using double-stranded sequencing. Double-stranded sequencing may include a double-stranded nucleic acid template free in solution or coupled to a support. The double-stranded nucleic acid template may have a secondary structure, such as a double helix structure. The double helix structure may reduce or prevent interactions between double-stranded nucleic acid templates coupled to the same support. Reducing or preventing interactions between the double-stranded nucleic acid templates may increase the linearity of the signal detected during sequencing. Additionally, combining double-stranded sequencing with nucleotides comprising detectable labels may both increase linearity and increase the signal-to-noise ratio. FIGS. 4A-4D show examples of double-stranded sequencing methods and examples of sequencing results using labeled and non-labeled nucleotides. FIG. 4A shows an example comparison between single-stranded 401 and double-stranded 402 sequencing results. The single-stranded sequencing 401 example shows signal that is both positive and negative with respect to the y-axis of the plot and varies non-monotonically. The double-stranded sequencing 402 example shows signal that is positive with respect to the y-axis of the plot and varies monotonically with the number of nucleotides incorporated. FIG. 4B shows example sequencing results for double-stranded sequencing using polyanion electrostatic moieties. Polyanion electrostatic moieties may comprise one or more of a phosphate, phosphonate, sulfate, sulfonate, boronate, or carboxylate group. The detected signal in this example is both positive with respect to the y-axis and monotonic. Additionally, the detected signal may be outside the detectable signal noise (e.g., has a high signal-to-noise ratio). FIG. 4C shows example sequencing results of double-stranded sequencing using polycation electrostatic moieties. Polycation electrostatic moieties may comprise one or more of a pyridinium, imidazolium, guanidinium, iminium, primary amine, secondary amine, tertiary amine, or quaternary ammonium. As with polyanion electrostatic moieties, polycation electrostatic moieties may generate signals that are outside the detectable signal noise. However, polycation electrostatic moieties may generate signals that are negative or opposite to the signals generated with a polyanion electrostatic moiety. FIG. 4D shows example sequencing results of double-stranded sequencing using both polyanion and polycation electrostatic moieties. The polyanion and polycation electrostatic moieties may generate detectable signals that are outside the detectable signal noise and that are both positive and negative (e.g., opposite signal direction with respect to one another).

Polycation electrostatic moieties may be useful for improving single-to-noise ratio, such as during sequencing. Detectable labels, such as polycation or polyanion electrostatic moieties, may be useful in generating a monotonic signal, i.e. a linear signal when compared with signals from unmodified nucleotides. The linearizing signal may be due to structural transitions of a nucleic acid molecule caused by a detectable label. The structural transitions may lead to the changes in ion distribution around the nucleic acid molecule, resulting in a signal that is of the same magnitude as the signal generated by single nucleotide incorporation.

Figure 18A:
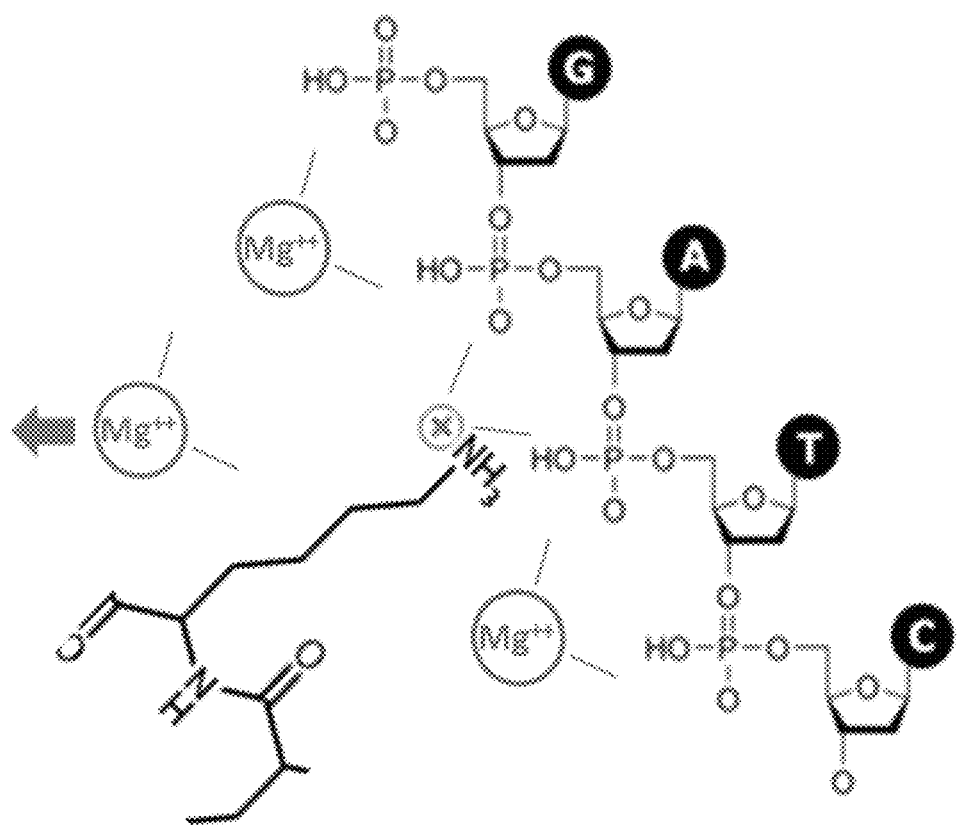
Figure 18B:
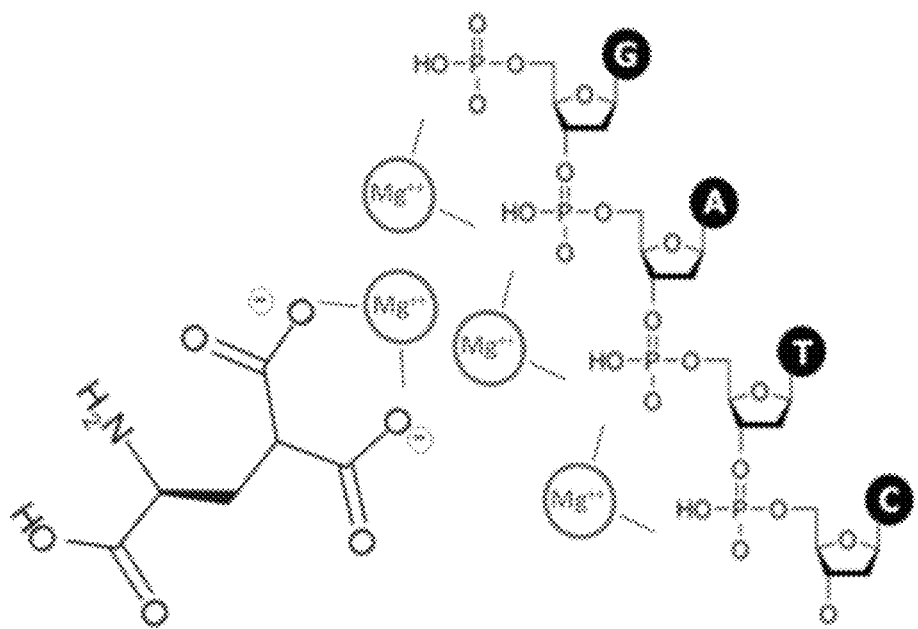

Polycation electrostatic moieties may comprise amines or amino acid residues, such as lysine, histidine, arginine, or any combination thereof. Polycation electrostatic moieties may displace or repel other polycations, such as magnesium ions ($Mg^{2+}$), from the vicinity of a nucleic acid molecule. The displacement of other polycations may result in a lower conduction current, which may be detected as a negative signal by a sensor. Polyanion electrostatic moieties, such as carboxylic acid groups, may attract or concentrate polycations, such as $Mg^{2+}$, around a nucleic acid molecule. The detectable label may comprise a charge group. The detectable label may be monovalent (e.g., have a single positive or negative charge, such as, e.g., +1 or −1) or polyvalent (e.g., have multiple positive or negative charges, such as, e.g., +2 or −2). The detectable label, such as a polycation or polyanion detectable label, may have from about one to about fifty or more positive or negative charges. In some cases, the detectable label may have greater than or equal to about 1, 2, 3, 4, 5, 6, 7, 8, 9, 10, 12, 15, 20, 25, 30, 40, 50, or more charge groups. The detectable label may include from about 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50 charge groups. In an example, a detectable label may be a polycation electrostatic moiety comprising three lysine residues, six lysine residues, or more than six lysine residues. In another example, a detectable label may be a polyanion electrostatic moiety comprising three carboxylic acid groups, six carboxylic acid groups or more than six carboxylic acid groups. The higher concentration of polycation electrostatic moieties may result in a higher conduction current, which may be detected as a positive signal by a sensor. The number of polycations or polyanions in a detectable label may correlate with the strength of a signal as detected by a sensor. For example, a detectable label with six lysine residues (e.g., K6 label (SEQ ID NO: 6)) may produce a stronger negative signal compared to a detectable label with three lysine groups (i.e., K3 label). Similarly, six carboxylic acid groups may produce a stronger positive signal as compared to three carboxylic acid groups in a detectable label. A larger charge state of a detectable label may lead to greater non-specific binding to surfaces, such as glassware. For example, a K6 label (SEQ ID NO: 6) may have a higher charge state than a K3 label and, therefore, the K6 label (SEQ ID NO: 6) may have greater non-specific binding compared to the K3 label. An example of polycation electrostatic moiety with a lysine residue is shown in FIG. 18A. An example of polyanion electrostatic moiety with a carboxylic acid group is shown in FIG. 18B.

Detectable labels may be switchable between a charged state and a neutral state or between one charge state and another charge state (e.g., positive to negative charge or negative to positive charge). The detectable label may switch a charge state in response to solution conditions, such as buffer conditions, e.g., such as pH or ionic strength of the buffer. Switchable detectable labels may be in a charged state during nucleic acid incorporation reaction (e.g., during signal detection) and may be in a neutral state rest of the time. In an example, nucleotide incorporation is detected during an incorporation event and the detectable labels may be charged during incorporation. In another example, nucleotide incorporation may be detected subsequent to nucleotide incorporation and the detectable label may not be charged during incorporation, but may be switched such that the detectable labels are charged during detection. In another example, the detectable labels have one charge during incorporation (e.g., positive, negative, or neutral) and are switched to have another charge during detection (e.g., negative or positive). Switch labels may be useful in reducing non-specific binding compared to the detectable label that remain in a charged state throughout the process, a K6 label (SEQ ID NO: 6), for example. An example of a histidine switch label is shown in FIG. 18C. As shown in FIG. 18C, a switch label may comprise histidine imidazole residues that can switch between a neutral state and a positive state in response to pH of the buffer. Example switch labels may include detectable labels with greater than or equal to 1, 2, 3, 4, 5, 6, 8, 10, 12, or more histidine groups. In an example, a detectable label has three histidine groups (e.g., H3), six histidine groups (e.g., H6 (SEQ ID NO: 1)), or more than six histidine groups. The switch label may be in a neutral state when the pH is equal to or greater than 7. The switch label may be in a positive state when the pH is equal to or less than 5. When the switch label is in a neutral state, the label may not non-specifically bind to surfaces and may have greater mobility when compared to the label in a positive state. Switch labels may be kept in a positive state during signal detection by a sensor in order immobilize the label. Switch labels may be maintained in a neutral state when the nucleotide is directed towards and/or away (e.g., when the nucleotide is mobile within the system) from a target nucleic acid molecule.

Non-specific binding of detectable labels may be reduced by altering reaction conditions. For example, a K6 label (SEQ ID NO: 6) may be used along with a high concentration of low affinity peptides, such as a K3 label. In such situation, the K6 label (SEQ ID NO: 6 may exhibit reduced non-specific binding due to competition for binding surfaces from the low affinity peptides. In some cases, non-specific binding may be reduced by using high ionic strength buffers. For example, buffer with 200 mM potassium chloride (KCl) may reduce non-specific binding by a K6 label (SEQ ID NO: 6), in turn, mobilizing the K6 label (SEQ ID NO: 6) to maintain the K6 label (SEQ ID NO: 6) in solution.

Figure 19:
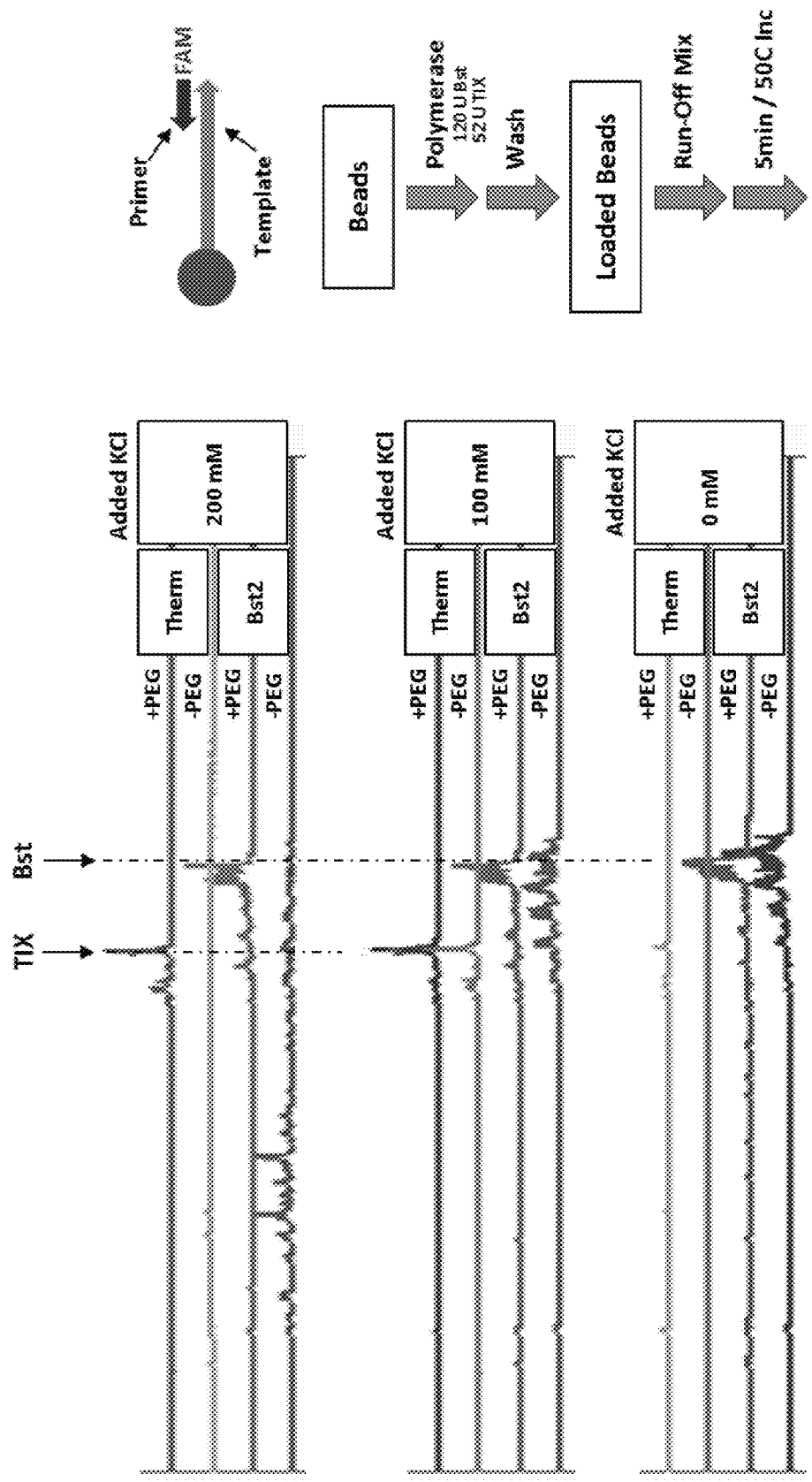
FIG. 19 shows activity of polymerizing enzymes in different salt concentrations and in the presence or absence of polyethylene glycol (PEG)

Polymerizing enzymes may be kinetically active in altered reaction conditions used with the switch labels and/or with the nucleotides comprising the detectable label. In some cases, polymerizing enzymes may be selected based on the kinetic activity and/or compatibility with the detectable label. For example, Type B polymerases, such as 9° N, RB69, KOD polymerases with larger binding pockets may be used with large detectable labels. In some cases, polymerizing enzymes that can tolerate high ionic strength buffers, such as Type B polymerases, Terminator IX, Bst 3.0, Φ29, Taq polymerase, may be used with high salt buffers and with polycation electrostatic moieties, such as a K6 label (SEQ ID NO: 6). Tolerance of polymerizing enzymes may be improved by adding volume excluders, such as, for example, polyethylene glycol (PEG), dextran, or similar compounds. As shown in FIG. 19, polymerizing enzymes may exhibit improved salt tolerance during nucleic acid incorporation reaction in the presence of PEG. A template may be coupled to a bead. A primer may be complementary to the 3' end of the template strand. A primer may be fluorescently labeled with 6-FAM fluorophore and extended by incorporation of individual nucleotides. The primer extension reaction may be detected by a sensor.

The primer extension reaction may be facilitated by a polymerizing enzyme, such as, for example, thermostable polymerizing enzymes. Examples of polymerase enzymes that may be used for extension reactions include, but not limited to, *Thermus thermophilus* HB8, mutant *Thermus oshimai, Thermus scotoductus; Thermus thermophilus* 1B21, *Thermus thermophilus* GK24, *Thermus aquaticus* polymerase (AmpliTaq® FS or Taq (G46D, F667Y), Taq (G46D, F667Y, E681I), and Taq (G46D, F667Y, T664N, R660G), *Pyrococcus furiosus* polymerase, *Thermococcus gorgonarius* polymerase, *Pyrococcus* species GB-D polymerase, *Thermococcus* sp. (strain 9° N-7) polymerase, *Bacillus stearothermophilus* polymerase (Bst), *Bacillus* caldotenax DNA polymerase (Bca) Tsp polymerase, ThermalAce™ polymerase (Invitrogen), *Thermus flavus* polymerase, *Thermus litoralis* polymerase, *Thermus* Z05 polymerase, delta Z05 polymerase (e.g. delta Z05 Gold DNA polymerase), *Sulfolobus* DNA Polymerase IV, or mutants, variants, or derivatives thereof. Additional examples of polymerase enzymes that may be used for primer extension reactions are non-thermostable polymerases, including, but not limited to, DNA polymerase I, mutant DNA polymerase I, including, but not limited to, Klenow fragment and Klenow fragment (3' to 5' exonuclease minus), T4 DNA polymerase, mutant T4 DNA polymerase, T7 DNA polymerase, mutant T7 DNA polymerase, phi29 DNA polymerase, and mutant phi29 DNA polymerase.

In some examples, the primer extension reaction may be performed in various salt concentrations, such as three salt concentrations (about 0 mM, 100 mM, and 200 mM), and in the presence or absence of PEG. For example, one set of experiments may be conducted with PEG and another set may be conducted without PEG. FIG. 19 shows example results of a primer extension reaction conducted in various salt and PEG concentrations with different types of polymerizing enzymes. When the buffer lacks KCl (e.g., has 0 mM KCl), Bst 2.0 polymerase may incorporate nucleotides regardless of the presence (e.g., +PEG) or absence (e.g., −PEG) of PEG, as indicated by the presence of peaks in both +PEG and −PEG. When the buffer lacks KCl (e.g., has 0 mM KCl), TIX polymerase may not incorporate nucleotides regardless of the presence or absence of PEG, as indicated by the absence of peaks in both +PEG and −PEG. When the buffer comprises 100 mM KCl, both the polymerizing enzymes may incorporate nucleotides regardless of the presence or absence of PEG, as indicated by the presence of peaks in both +PEG and −PEG. When the buffer comprises 200 mM KCl, both the polymerizing enzymes may incorporate nucleotides in the presence of PEG, as indicated by peaks in +PEG, but may not incorporate nucleotides in the absence of PEG.

In some cases, signal-to-noise ration may be improved by including molecules that can improve conduction current produced by polycations, such as $Mg^{2+}$, $Ca^{2+}$, $Zn^{2+}$. Such molecules may associate with polycations that may lead to increased conduction current. Non-limiting examples of molecules the may improve conduction current include, but are not limited to, phosphodiester backbone of a nucleic acid molecules (e.g., dT3, dT6, dT12 (SEQ ID NO: 2), etc.), carboxyglutamic acid (Gla (e.g., the γ-carboxyglutamic acids Gla3, Gla6 (SEQ ID NO: 7), Gla12 (SEQ ID NO: 8), etc.), specific peptides (e.g., peptides with the sequences DIETDIET (SEQ ID NO: 3), FDGDFDGD (SEQ ID NO: 4), and/or STLPLPP (SEQ ID NO: 5)), or small molecules (e.g., pyridines, NTA, IDA, or phosphanes).

A target nucleic acid molecule may be sequenced and/or a length of the target nucleic acid molecule may be determined. The target nucleic acid molecule may be a fragmented nucleic acid molecule or may be a non-fragmented nucleic acid molecule. The target nucleic acid molecule may be amplified prior to detection. The target nucleic acid molecule may be amplified in solution and/or on a support. The target nucleic acid molecule amplified on a support may be immobilized to the support prior to amplification. The target nucleic acid molecule may be amplified by bridge amplification, wild fire amplification, recombinase polymerase amplification, isothermal amplification, or using any other amplification technique. Sequencing or determining a length of the target nucleic acid molecule may comprise providing a plurality of double-stranded nucleic acid molecules adjacent to a sensor array. A given, or individual, double-stranded nucleic acid molecule may be disposed adjacent to a given, or individual, sensor of the sensor array. The double-stranded nucleic acid molecule may comprise a first single-stranded nucleic acid molecule and a second-single stranded nucleic acid molecule. The first and second single-stranded nucleic acid molecules may have sequence complementarity with one another. The sensor may be electrically coupled to a charge double layer (e.g., within a Debye length) of the double-stranded nucleic acid molecule. A portion of the second single-stranded nucleic acid molecule may be released from the first single-stranded nucleic acid molecule to provide a segment of the first single-stranded nucleic acid molecule that is not hybridized to the second single-stranded nucleic acid molecule. The segment may be brought in contact with an individual nucleotide. The individual nucleotide may be subject to a nucleic acid incorporation reaction that generates a third single-stranded nucleic acid molecule. The third single-stranded nucleic acid molecule may have sequence complementarity with the first single-stranded nucleic acid molecule. During the nucleic acid incorporation reaction, the sensor may be used to detect signals indicative of incorporation of the individual nucleotides into the third single-stranded nucleic acid molecule, thereby determining a sequence of the non-hybridized segment.

The double-stranded nucleic acid molecule may be coupled to a support. The support may be a bead or one or more surfaces of the sensor array. A plurality of double-stranded nucleic acid molecules may be coupled to a plurality of beads or a plurality of locations on the surface of the sensor array. Each bead of the plurality of beads may be disposed adjacent to a given sensor. The charge double layer (e.g., Debye length) may be adjacent to the surface of the bead. Alternatively, or in addition to, the plurality of double-stranded nucleic acid molecules may be coupled to one or more surfaces of the sensor array. A given double-stranded nucleic acid molecule may be coupled to a surface of a given sensor. The charge double layer (e.g., Debye length) may be adjacent to the surface of the given sensor. The double-stranded nucleic acid molecule coupled to the support may be clonally amplified prior to sequencing so that support surface is coupled to a clonal population of double-stranded nucleic acid molecules.

A given sensor may comprise at least one, at least two, at least three, or at least four electrodes, or more electrodes. In an example, a given sensor comprises at least two electrodes. In another example, a given sensor comprises two electrodes. The electrodes may be exposed to the solution in which the primer extension reaction takes place. Alternatively, or in addition to, the electrodes may be buried within the sensor array and, therefore, may not be exposed to the solution in which the primer extension reaction takes place. The electrodes of a given sensor may detect signals indicative of incorporation of individual nucleotides into the double-stranded nucleic acid molecule. Signals indicative of incorporation events may include changes in impedance, conductance, or charge in the electronic double layer. In an example, signals indicative of incorporation of individual nucleotides are electrical signals generated by an impedance or impedance change in the charge double layer. The signals indicative of incorporation of individual nucleotides may be steady state signals, transient signals, or a combination of steady state and transient signals. Signals may be detected transiently or during steady state conditions. In a transient signal detection modality, the detection occurs during or closely after nucleotide incorporation. In steady state detection, reading of the sensor may occur after the completion of the incorporation event. A steady state change in signal may be constant until a change is introduced to the environment around the sensor.

Figure 5:
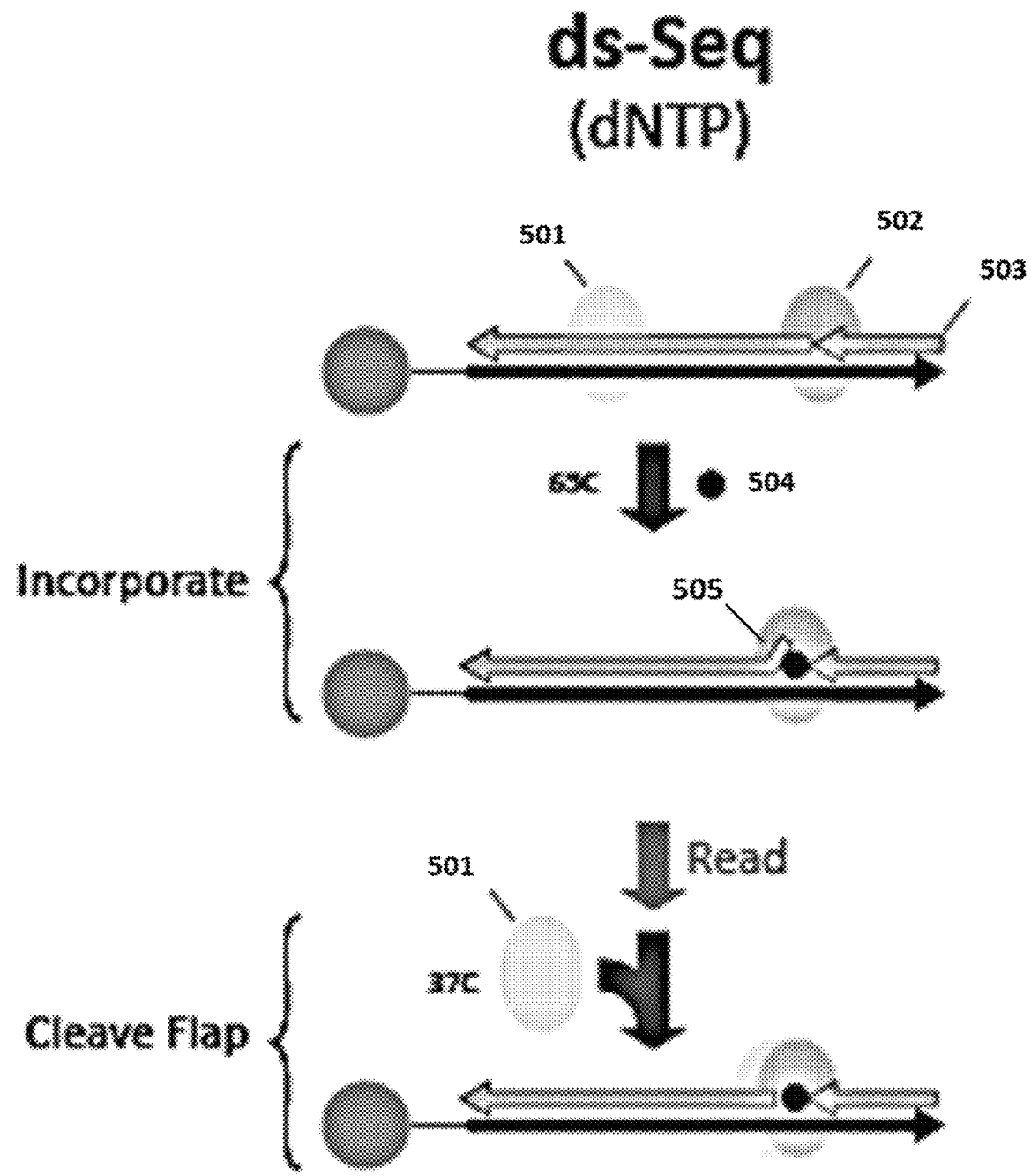
FIG. 5 shows an example method for double-stranded sequencing.

FIG. 5 shows an example method for double-stranded sequencing. The double-stranded nucleic acid template may have a uniform structure that produces a linear, substantially linear, or semi-linear response to a change in charge due to nucleotide incorporation. The double-stranded nucleic acid may comprise a priming site adjacent to the 3-prime end of the first single-stranded nucleic acid (e.g., the nucleic acid template to be sequenced). A primer 503 may have complementarity with the 3-prime end of the first single-stranded nucleic acid molecule and may hybridize with the 3-prime end of the first single-stranded nucleic acid molecule. Alternatively, or in addition to, the second double stranded nucleic acid may be nicked to provide a primer and a strand to be displaced (e.g., displacement strand). The second single-stranded nucleic acid may comprise a uracil nucleotide. The second single-stranded nucleic acid molecule may be nicked at the uracil nucleotide. The second single-stranded nucleic acid molecule may be nicked by any enzyme capable of cleaving a uracil (e.g. uracil DNA glycosylase). A polymerizing enzyme 502 may bind to the double-stranded nucleic acid and facilitate a primer extension reaction. In an example, the polymerizing enzyme 502 is a polymerase, such as Bst DNA polymerase. The primer extension reaction may displace an end of the second single-stranded nucleic acid and create a single-stranded flap 505 and a segment of the first single-stranded nucleic acid molecule that is not hybridized to the second single-stranded nucleic acid molecule. A segment may be a portion of the first single-stranded nucleic acid molecule that is not hybridized to the second or third single-stranded nucleic acid molecule. The segment may not comprise the entire first-single stranded nucleic acid molecule. The segment may be a single nucleotide in length or may be multiple nucleotides in length. A flap 505 may be a nucleotide coupled to the second single-stranded nucleic acid molecule, but not hybridized to the first single-stranded nucleic acid molecule. The flap 505 may induce the polymerizing enzyme 502 to stutter and lead to phasing during sequencing. The flap 505 may be recognized and cleaved by a flap endonuclease (FEN) 501. The FEN 501 may be thermostable or mesophilic. The thermostable FEN may remain associated with the nucleic acid after cleavage of the flap 505 and during subsequent nucleic acid incorporation reactions. The mesophilic FEN may be inactivated during the primer extension reaction and may be replenished to the system after each incorporation and detection cycle. The flap may be cleaved after detecting signals indicative of nucleotide 504 incorporation and prior to incorporation of subsequent nucleotides. Incorporation of the nucleotide 504 may generate a gain in negative charge of the double-stranded nucleic acid molecule. Cleaving the flap 505 may generate a loss in negative charge of the double-stranded nucleic acid. Therefore, incorporation of a nucleotide followed by cleavage of the flap may generate a net neutral change in charge, resulting in little or no detectable signal.

Figure 6:
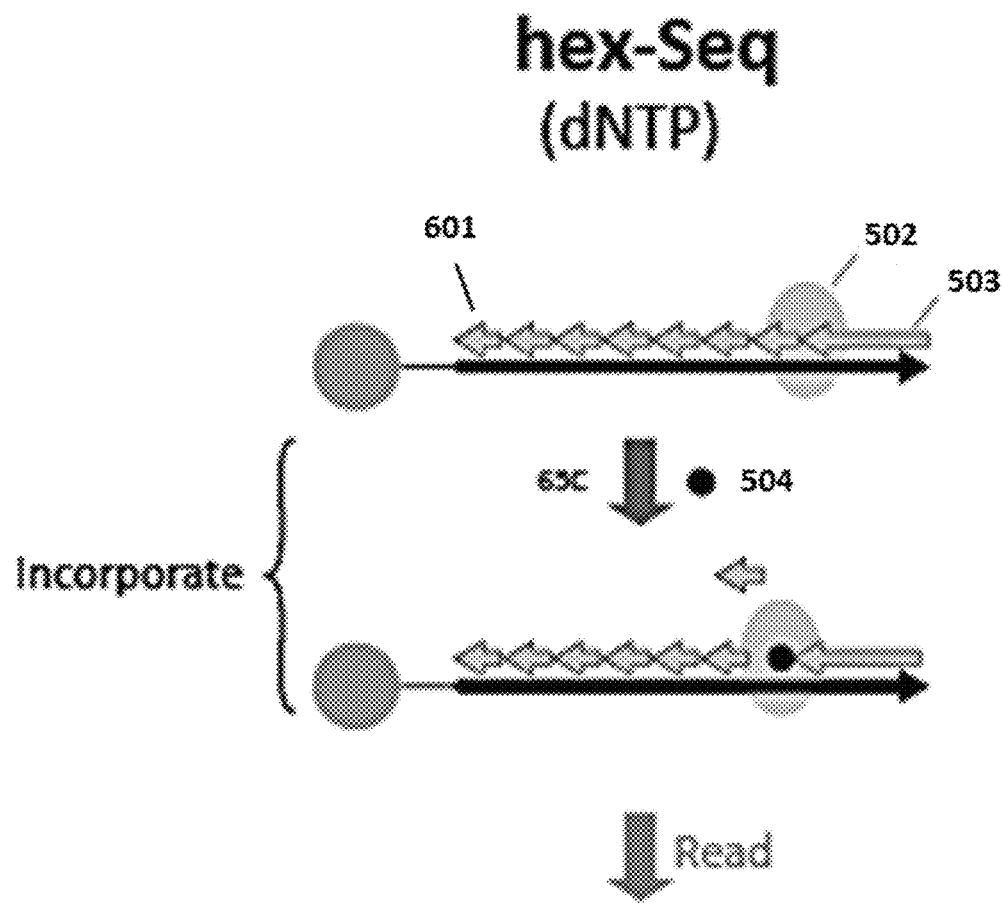
FIG. 6 shows an example method for double-stranded sequencing using random hexamers.

The second single-stranded nucleic acid of the double-stranded nucleic acid may comprise subunits. FIG. 6 shows an example method for double-stranded sequencing using nucleic acid subunits 601. The nucleic acid subunits 601 may be selected from a library of nucleic acid subunits 601. The library of nucleic acid subunits may comprise random sequences. The nucleic acid subunits 601 may comprise at least 2, at least 3, at least 4, at least 5, at least 6, at least 7, at least 8, at least 9, at least 10, or more nucleotides. In an example, the nucleic acid subunits 601 comprise at least 5 nucleotides. In an example, the nucleic acid subunits 601 comprise at least 6 nucleotides. The nucleic acid subunits 601 may all be the same length or may vary in length. The library of nucleic acid subunits may comprise DNA subunits, peptide nucleic acid (PNA) subunits, RNA subunits, or lock nucleic acid (LNA) subunits. Association between the nucleic acid subunits 601 and the first single-stranded nucleic acid (e.g., nucleic acid template molecule) may generate a double-stranded nucleic acid molecule and linearize the nucleic acid template. Nucleotide 504 incorporation (e.g., via a primer extension reaction) may displace the subunits and provide a segment of non-hybridized single-stranded nucleic acid template. In an example, the nucleic acid subunits are non-charged and, therefore, displacement of a nucleic acid subunit 601 does not alter the charge state of the double-stranded nucleic acid molecule. In an example, the nucleic acid subunits are charged and displacement of the subunit 601 alters the charge state of the double-stranded nucleic acid molecule. The use of nucleic acid subunits may facilitate double-stranded sequencing without the use of a FEN.

The individual nucleotides may comprise reversible terminators. The reversible terminators may prevent the addition of subsequent nucleotides into the third single-stranded nucleic acid molecule. Alternatively, or in addition to, the reversible terminator may prevent an additional nucleotide from stably hybridizing with the first single-stranded nucleic acid molecule. The reversible terminator may reduce the formation of homopolymers and/or incorporation of more than one nucleotide during an incorporation cycle. The reversible terminator may be coupled to the oxygen atom of the 3-prime hydroxyl group of the nucleotide pentose (e.g., 3'-O-blocked reversible terminator). Alternatively, or in addition to, the reversible terminator may be coupled to the nucleobase of the nucleotide (e.g., 3'-unblocked reversible terminator). The reversible terminator may include a detectable label. The reversible terminator may comprise an allyl, hydroxylamine, acetate, benzoate, phosphate, azidomethyl, or amide group. The reversible terminator may be removed by treatment with a reducing agent, acid or base, organic solvents, ionic surfactants, photons (photolysis), or any combination thereof. Removal of the reversible terminator of a 3'-O-blocked reversible terminator may return the hydroxyl group to pentose of the nucleotide and allow for the incorporation of subsequent nucleotides into the third single-stranded nucleic acid molecule.

FIGS. 7A and 7B show example methods for double-stranded sequencing using reversible terminators 701. FIG. 7A shows an example method for double-stranded sequencing using reversible terminators and a FEN 501. The second single-stranded nucleic acid of the double-stranded nucleic acid may comprise a uracil nucleotide that is nicked by a uracil-DNA glycosylase. Alternatively, or in addition to, the second single-stranded nucleic acid molecule may comprise a displacement strand and a primer. A polymerizing enzyme 502 may bind to the primer 503. The polymerizing enzyme may be an enzyme that enables incorporation with high efficiency and fidelity. The polymerizing enzyme may be, without limitation, a Bst polymerase, reverse transcriptase, type A polymerase, type B polymerase, or type C polymerase. The polymerizing enzyme may incorporate an individual nucleotide comprising a reversible terminator 701. Incorporation of the nucleotide 701 may generate a flap. The incorporated nucleotide 701 may be detected and, subsequent to detection, the flap may be cleaved by a FEN 501. The FEN 501 may be mesophilic. The mesophilic FEN 501 may be brought into contact with the flap after detection of the incorporated nucleotide and may be removed prior to the next incorporation cycle. The FEN 501 may be replenished with each nucleotide incorporation cycle. The reversible terminator may be reversed during or after cleavage of the flap. The reversible terminator may be reversed by introducing a reducing agent to the solution. In an example, the reducing agent is dithiothreitol (DTT). After the reversible terminator is reversed, the cycle of nucleotide incorporation, detection, cleavage of the flap, and reversing the terminator is repeated until a portion of or the entire first single-stranded nucleic acid is sequenced.

FIG. 7B show an example method for double-stranded sequencing using reversible terminators and nucleic acid subunits. The second single-stranded nucleic acid molecule may comprise random nucleic acid subunits. The second single-stranded nucleic acid molecule may additionally comprise a primer 503. A polymerizing enzyme 502 may bind to the primer and incorporate an individual nucleotide 701 into the third single-stranded nucleic acid molecule. The individual nucleotide may displace a portion of or an entire nucleic acid subunit. The incorporated nucleotide may be detected after incorporation into the third single-stranded nucleic acid molecule. The individual nucleotide may include a reversible terminator. The reversible terminator may be reversed after detection of the incorporated nucleotide. The reversible terminator may be reversed by introducing a reducing agent to the solution. In an example, the reducing agent is DTT. After the reversible terminator is reversed, the cycle of nucleotide incorporation, detection, and reversing the terminator may be repeated until a portion of or the entire first single-stranded nucleic acid is sequenced.

The double-stranded nucleic acid molecule may comprise detectable labels. The detectable labels may be electrostatic moieties, fluorescent labels, colorimetric labels, chemiluminescent labels, radio labels, or any combination thereof. The detectable labels may be coupled to the second single-stranded nucleic acid molecule, the nucleotides to be incorporated into the third single-stranded nucleic acid, or any combination thereof. The detectable label may be coupled to the phosphate of a nucleotide, the nucleobase of a nucleotide, or to a reversible terminator couple to a nucleotide. In an example, the detectable label is coupled to the nucleobase of the nucleotide. The detectable label may be reversibly coupled or irreversibly coupled to a nucleotide. The detectable label may generate signals indicative of nucleotide incorporation into the third single-stranded nucleic acid molecule or cleavage of a nucleotide from the second single-stranded nucleic acid molecule. The signals from the detectable label may be detected by the sensor array.

Figure 8:
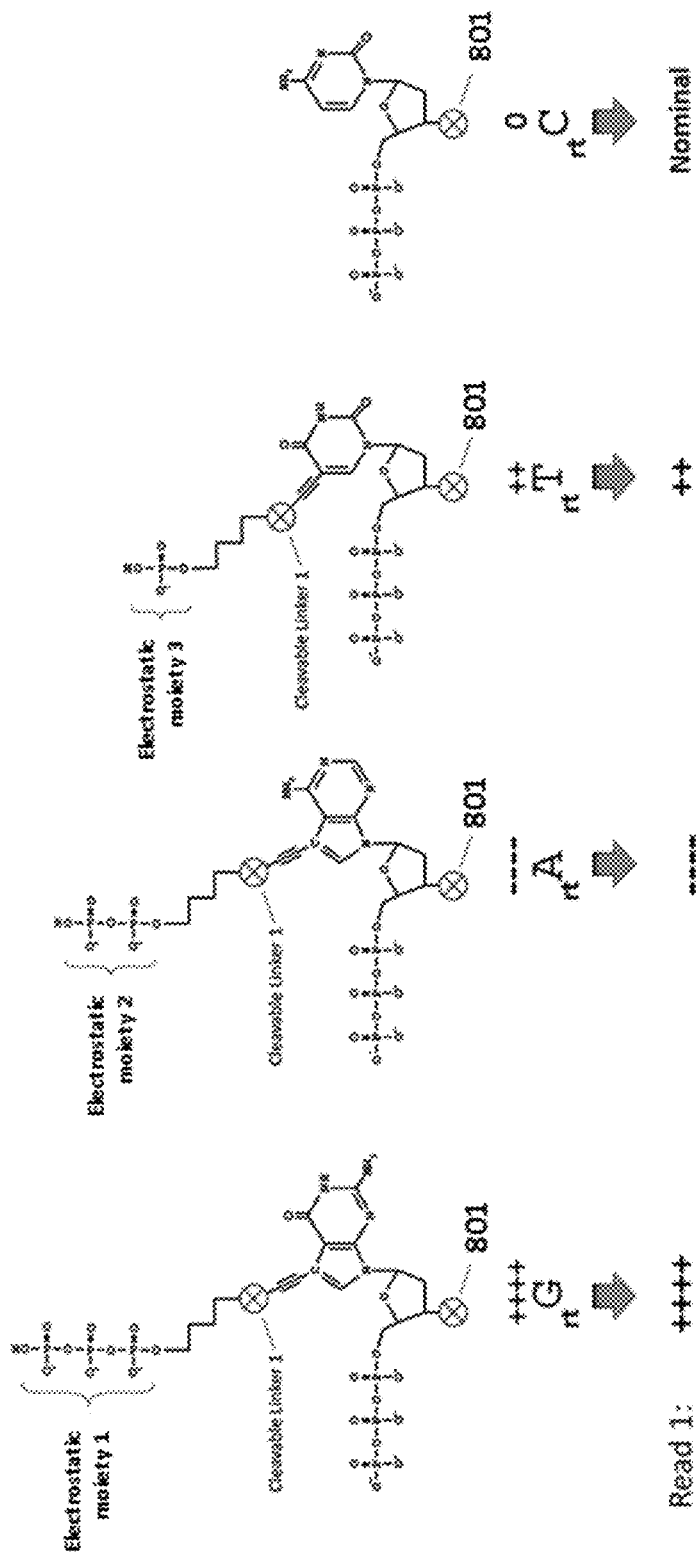
FIG. 8 shows an example sequencing method using a different type of electrostatic moiety for each type of nucleotide.

In an example, each different type of nucleotide may be coupled to a different detectable label. Each type of detectable label may indicate the nucleotide base to which it is bound. For example, each of guanine, cytosine, adenine, thymine, and uracil may have different detectable labels that are resolvable from each other. FIG. 8 shows example nucleotides each having different electrostatic moieties and a reversible terminator 801. The electrostatic moieties may be polyanion or polycation electrostatic moieties. One or more individual nucleotides may have no electrostatic moiety. One or more individual nucleotides may have a polycation electrostatic moiety. The polycation electrostatic moieties may have varying degrees of charge. One or more individual nucleotides may have a polyanion electrostatic moiety. The polyanion electrostatic moieties may have varying degrees of charge. The presence of excess charge on the double-stranded nucleic acid molecule may reduce the efficiency of the polymerizing enzyme. The polymerizing enzyme may be an enzyme that enables incorporation of nucleotides with detectable labels with high efficiency and fidelity. The polymerizing enzyme may be, without limitation, a Bst polymerase, reverse transcriptase, type A polymerase, type B polymerase, or type C polymerase. The electrostatic moiety may be reversibly or irreversibly coupled to the nucleotide. The nucleotides electrostatic moieties may be coupled to the second single-stranded nucleic acid molecule or to the individual nucleotides that are incorporated into the third single-stranded nucleic acid. In an example, the electrostatic moieties are coupled the individual nucleotides that are incorporated into the third single-stranded nucleic acid molecule. The individual nucleotides may be directed to contact the double-stranded nucleic acid individually and sequentially (e.g., contacted with A, followed by T, followed by C, followed by G, and so forth) and the sensor may detect nucleotide incorporation between each addition. Alternatively, or in addition to, the nucleotides may be directed to contact the double-stranded nucleic acid molecule simultaneously (e.g., contacted with a solution comprising all of G, A, T, and C at once) and the sensor may detect a change in charge after nucleotide incorporation. Different electrostatic moieties coupled to different types of individual nucleotides may allow for each type of individual nucleotides incorporated into the third single-stranded nucleic acid molecules to be detected and distinguished from each other. The individual nucleotides may be resolved using a single read per incorporation cycle. After detection of nucleotide incorporation, the detectable label may be cleaved from the nucleotide. The cleavage reaction may include a reduction reaction, acid or base cleavage, cleavage in organic solvents (e.g., formamide or urea), cleavage by ionic surfactant, or combination thereof.

Figure 9:
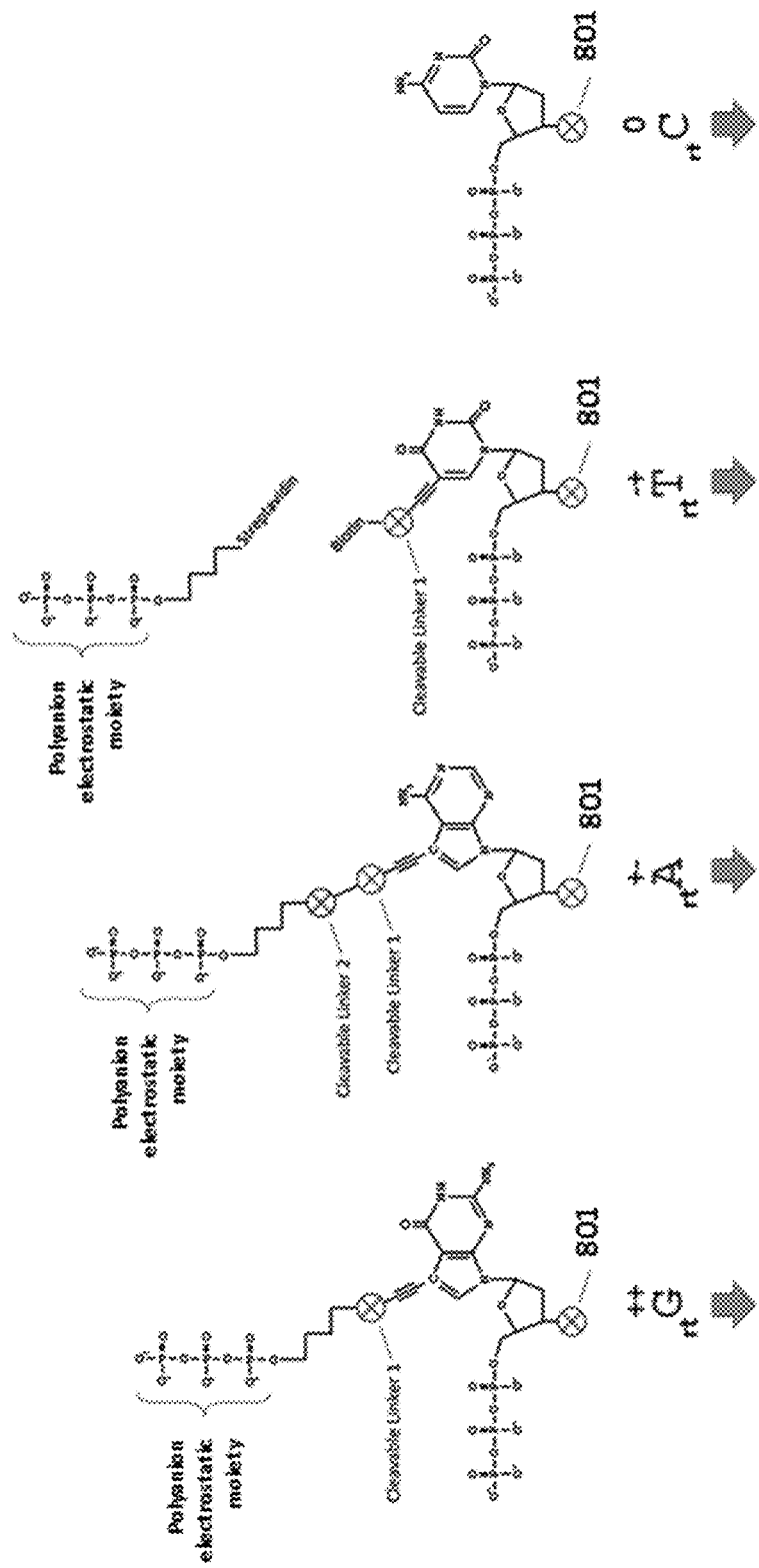
FIG. 9 shows an example sequencing method using a single type of electrostatic moiety for each type of nucleotide.

In an example, each different type of nucleotide may have the same detectable label. FIG. 9 shows example nucleotides each having the same electrostatic moieties and different, reversible coupling mechanisms. The coupling mechanisms may be decoupled, or cleaved, by a reduction reaction, acid or base cleavage, cleavage in organic solvents, cleavage by ionic surfactant, or combination thereof. Additionally, the electrostatic moieties may be coupled to the individual nucleotides by a variety of coupling mechanisms including, but not limited to, covalent bonds, association-disassociation interactions, ligand and binding pair interactions (e.g., Streptavidin-Biotin interaction), hybridization interaction, or any combination thereof. The individual nucleotides may be directed to contact the double-stranded nucleic acid individually and sequentially (e.g., contacted with A, followed by T, followed by C, followed by T, and so forth) and the sensor may detect nucleotide incorporation between each addition. Alternatively, or in addition to, the nucleotides may be directed to contact the double-stranded nucleic acid simultaneously (e.g., contacted with a solution of all A, T, C, and G at once) and the sensor may detect a change in charge after nucleotide incorporation. The change in charge may be used to determine a length of the nucleic acid target molecule. In an example (see FIG. 9), the nucleotides G, A, and T all have the same polyanion electrostatic moiety that is cleaved by condition one. Nucleotide C may not have a electrostatic moiety. The electrostatic moiety for A may further comprise a second coupling mechanism that is cleaved under condition two. The electrostatic moiety for T may initially not be present during nucleotide incorporation, but may be coupled to the nucleotide using a third coupling mechanism (e.g., Streptavidin-Biotin). The double-stranded nucleic acid molecule may be contacted with all four nucleotides at once. One or more nucleotides may be incorporated into a plurality of third single-stranded nucleic acid molecules adjacent to the sensor array. After the incorporation reaction, nucleotide incorporation may be read or detected. In this example, nucleotides G and A may have a polyanion electrostatic moiety during the initial read (e.g., detection cycle) and both G and A may generate a detectable signal. Nucleotides T and C may initially not comprise a electrostatic moiety nor generate a detectable signal. The electrostatic moiety for A may be removed by contacting the nucleotide with the second cleavage condition and T may obtain a electrostatic moiety by the introduction of a electrostatic moiety comprising the third coupling mechanism (e.g., a streptavidin group). A second read (e.g., detection cycle) may be performed and both G and T may generate a detectable signal and A and C may not generate a detectable signal. The incorporated nucleotides may then be resolved and distinguished from each other by combining signals from the first and second read and matching the signal to the corresponding nucleotides. After the first and second read, the electrostatic moieties may be cleaved using cleavage condition one.

Figure 10:
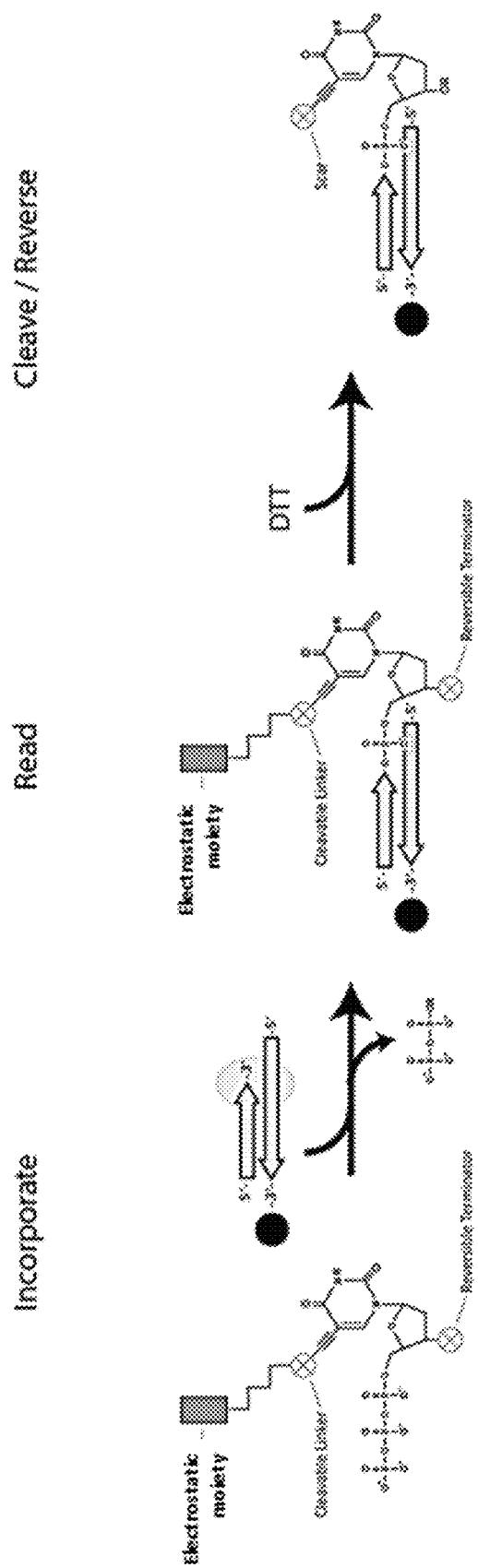
FIG. 10 shows an example method for sequencing using electrostatic moieties and reversible terminators.

FIG. 10 shows an example method for sequencing using electrostatic moieties and reversible terminators. The nucleic acid template to be sequences may be subjected to a nucleic acid incorporation reaction (e.g., primer extension reaction). The incorporated nucleotide may have a cleavable electrostatic moiety and a reversible terminator. The reversible terminator may prevent the addition of subsequent nucleotides from incorporating into the extended primer. After incorporation of the nucleotide the incorporated nucleotide may be read or detected. Following reading, the electrostatic moiety may be cleaved and the reversible terminator may be removed. The electrostatic moiety may be cleaved and the terminator may be removed using the same chemistry. Example chemistries include treatment with a reducing agent such as dithiothreitol (DTT) or tris92-carboxyethyl0phosphine (TCEP). Alternatively, or in addition to, the electrostatic moiety may be cleaved and the terminator may be removed using different cleavage and removal chemistries.

The detectable labels may be coupled to the nucleotides incorporated during the primer extension reaction or may be coupled to the nucleotides of the second single-stranded nucleic acid molecule. In an example, the second single stranded nucleic acid (e.g., the displacement strand) may comprise one or more detectable labels. FIGS. 11A and 11B show example methods for double-stranded sequencing using detectable labels coupled to the second single-stranded nucleic acid molecule. FIG. 11A shows an example sequencing method using detectable labels that are cleaved by a flap endonuclease 501. The second single-stranded nucleic acid molecule of the double-stranded nucleic acid molecule may comprise detectable labels. The detectable labels may be electrostatic moieties. Each nucleotide of the second single-stranded nucleic acid molecule may be coupled to a electrostatic moiety. Each different type of nucleotide in the second single-stranded nucleic acid molecule may be coupled to a different electrostatic moiety or coupled to the same electrostatic moiety. The polymerizing enzyme 502 may bind to the primer 503 adjacent to an end of the displacement strand. The polymerizing enzyme 503 may incorporate a nucleotide 504 into the third single-stranded nucleic acid molecule. The incorporated nucleotide may or may not have a electrostatic moiety. Incorporation of the nucleotide may create a flap. The flap may be cleaved by a FEN 501. The FEN 501 may be a thermostable or mesophilic FEN. Cleavage of the flap by a FEN 501 may remove a electrostatic moiety from the displacement strand, thereby altering the charge state of the double-stranded nucleic acid molecule. The change in charge state may be detected by the sensor array to generate a sequence of the first single-stranded nucleic acid molecule. Cycles of nucleotide incorporation, cleavage of the flap, and detection of the change in charge may be repeated until the sequence of the first single-stranded nucleic acid molecule is determined.

FIG. 11B shows an example double-stranded sequencing method using both detectable labels coupled to the second single-stranded nucleic acid molecule and reversible terminators. The detectable labels may be electrostatic moieties. Each nucleotide of the second single-stranded nucleic acid molecule may be coupled to a electrostatic moiety. Each different type of nucleotide in the second single-stranded nucleic acid molecule may be coupled to a different electrostatic moiety or coupled to the same electrostatic moiety. The polymerizing enzyme 502 may bind to the primer 503 adjacent to an end of the displacement strand. The polymerizing enzyme 502 may incorporate a nucleotide 701 into the third single-stranded nucleic acid molecule. The incorporated nucleotide may or may not have a electrostatic moiety and a reversible terminator. The flap may be cleaved by a FEN. The FEN may be thermostable or mesophilic. Cleavage of the flap by a FEN may remove a electrostatic moiety from the displacement strand, thereby altering the charge state of the double-stranded nucleic acid molecule. The change in charge state may be detected to generate a sequence of the first single-stranded nucleic acid molecule. After detecting nucleotide incorporation, the newly incorporated nucleotide may undergo a cleavage reaction to remove the reversible terminator. Removal of the reversible terminator may permit the incorporation of subsequent nucleotides into the third single-stranded nucleic acid molecule. Cycles of nucleotide incorporation, cleavage of the generated flap, detection of the change in charge, and removal of the reversible terminator may be repeated until the sequence of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection. Nucleotide incorporation and detection may be conduct for a set number of cycles or may be conducted until the primer extension reaction is complete.

The detectable label may be coupled to individual nucleotides that are incorporated into the third single-stranded nucleic acid molecule. FIG. 12A shows an example method for double-stranded sequencing using individual nucleotide coupled electrostatic moieties 1201 and a mesophilic FEN 501. A polymerizing enzyme may bind to the primer of the second single-stranded nucleic acid molecule to facilitate the incorporation of an individual nucleotide 1201. The individual nucleotide 1201 may comprise a electrostatic moiety bound to the nucleobase of the nucleotide. Incorporation of an individual nucleotide may generate a flap. The flap may be cleaved by a FEN. The FEN may be a mesophilic FEN and may be regenerated after each incorporation cycle. The flap may be cleaved after detection of the nucleotide incorporation event. The electrostatic moiety may be reversibly couple to the nucleotide. The electrostatic moiety may be cleaved at the same time or subsequent to cleavage of the flap. Cycles of nucleotide incorporation, detection of nucleotide incorporation, cleavage of the generated flap, and cleavage of the electrostatic moiety may be repeated until the sequence of at least a portion of the first single-stranded nucleic acid molecule is determined.

FIG. 12B shows an example method for double-stranded sequencing using electrostatic moieties and a thermostable FEN. A polymerizing enzyme 502 may bind to the primer 503 of the second single-stranded nucleic acid molecule to facilitate the incorporation of an individual nucleotide 1201. The individual nucleotide 1201 may comprise a electrostatic moiety bound to the nucleobase of the nucleotide. Incorporation of an individual nucleotide may generate a flap. The flap may be cleaved by a FEN 501. The FEN 501 may be a thermostable FEN and may remain associated with the double-stranded nucleic acid molecule after cleavage of the flap. The thermostable FEN may not be regenerated after each incorporation cycle. The flap may be cleaved prior to detection of the nucleotide incorporation event. The electrostatic moiety may be reversibly coupled to the nucleotide and may be cleaved after detection of the nucleotide incorporation event. Cycles of nucleotide incorporation, cleavage of the generated flap, detection of nucleotide incorporation, and removal of the electrostatic moiety may be repeated until the sequence of at least a portion of the first single-stranded nucleic acid molecule is determined.

The individual nucleotides may comprise both a detectable label and a reversible terminator. FIG. 13A shows an example method for double-stranded sequencing using electrostatic moieties, reversible terminators, and a mesophilic FEN. A polymerizing enzyme 502 may bind to the primer 503 of the second single-stranded nucleic acid molecule to facilitate the incorporation of an individual nucleotide 1301. The individual nucleotide 1301 may comprise a electrostatic moiety bound to the nucleobase of the nucleotide and a reversible terminator bound to the 3-prime side of the pentose. The reversible terminator may reduce homopolymer formation and/or the incorporation of multiple nucleotides per cycle. Incorporation of an individual nucleotide may generate a flap. The flap may be cleaved by a FEN 501. The FEN 501 may be a mesophilic FEN and may be regenerated after each incorporation cycle. The flap may be cleaved after detection of the nucleotide incorporation event. The electrostatic moiety may be reversibly couple to the nucleotide. The electrostatic moiety may be cleaved at the same time or subsequent to cleavage of the flap. The reversible terminator may be reversed prior to, simultaneously with, or subsequent to cleavage of electrostatic moiety. In an example, the electrostatic moiety is cleaved and the reversible terminator reversed by a reducing agent, such as DTT or TCEP. Cycles of nucleotide incorporation, detection of nucleotide incorporation, cleavage of the generated flap, cleavage of the electrostatic moiety, and reversing the reversible terminator may be repeated until the sequence of at least a portion of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection. Nucleotide incorporation and detection may be conduct for a set number of cycles or may be conducted until the primer extension reaction is complete.

FIG. 13B shows an example method for double-stranded sequencing using electrostatic moieties, a thermostable FEN, and reversible terminators. A polymerizing enzyme 502 may bind to the primer 503 of the second single-stranded nucleic acid molecule to facilitate the incorporation of an individual nucleotide 1301. The individual nucleotide 1301 may comprise a electrostatic moiety bound to the nucleobase of the nucleotide and a reversible terminator on the 3-prime side. The reversible terminator may reduce homopolymer formation and/or the incorporation of multiple nucleotides per cycle. Incorporation of an individual nucleotide may generate a flap. The flap may be cleaved by a FEN 501. The FEN 501 may be a thermostable FEN may remain associated with the double-stranded nucleic acid molecule after cleavage of the flap. The thermostable FEN may not be regenerated after each incorporation cycle. The flap may be cleaved prior to detection of the nucleotide incorporation event. The electrostatic moiety may be reversibly coupled and may be cleaved after detection of the nucleotide incorporation event. The reversible terminator may be reversed simultaneously with cleavage of electrostatic moiety or subsequent to cleavage of the electrostatic moiety. In an example, the electrostatic moiety is cleaved and the reversible terminator reversed by a reducing agent, such as DTT or TCEP. Cycles of nucleotide incorporation, cleavage of the generated flap, detection of nucleotide incorporation, cleavage of the electrostatic moiety, and removal of the reversible terminator may be repeated until the sequence of at least a portion of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection. Nucleotide incorporation and detection may be conduct for a set number of cycles or may be conducted until the primer extension reaction is complete.

Figures 14A, 14B:
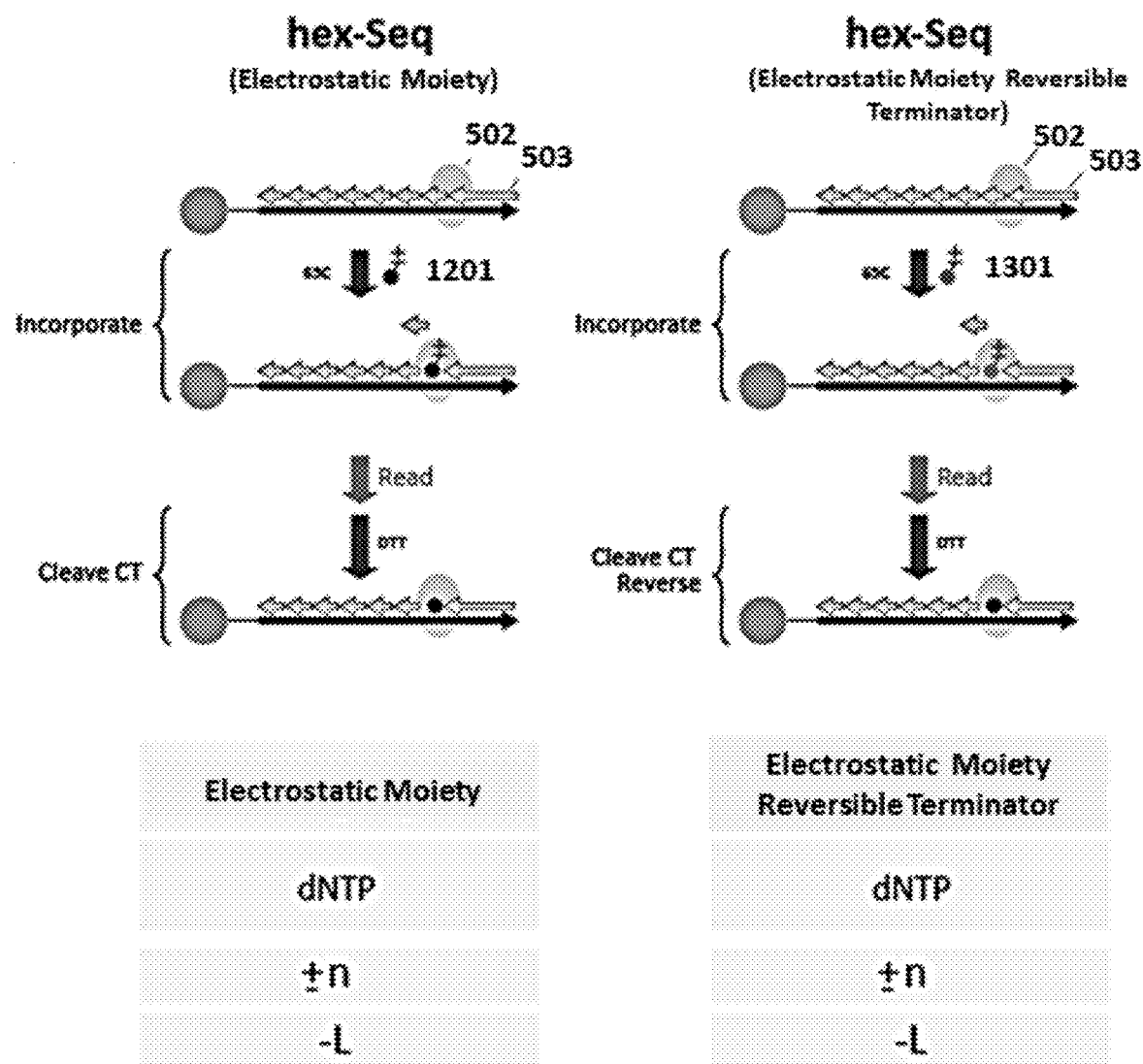
FIG. 14A shows an example method for double-stranded sequencing using detectable labels and nucleic acid subunits.
FIG. 14B shows an example method for double-stranded sequencing using detectable labels, nucleic acid subunits, and reversible terminators.

FIG. 14A shows an example method for double-stranded sequencing using detectable labels and nucleic acid subunits. The detectable labels may be electrostatic moieties. The detectable labels may be reversibly coupled to the individual nucleotides. The second single-stranded nucleic acid may comprise random nucleic acid subunits and a primer 503. A polymerizing enzyme 502 may bind to the primer 503. The polymerizing enzyme 502 may incorporate an individual nucleotide with a electrostatic moiety into the third single-stranded nucleic acid molecule. Incorporation of the individual nucleotide 1201 may displace a portion of or an entire random nucleic acid subunit. The sensor array may detect signals indicative of incorporation events after the incorporation of the individual nucleotide into the third single-stranded nucleic acid molecule. After detection of the incorporation event, the reversible electrostatic moiety may be cleaved. In an example, the reversible electrostatic moiety is cleaved with a reducing agent such as DTT or TCEP. Cycles of nucleotide incorporation, nucleic acid subunit displacement, individual nucleotide detection, and cleavage of the electrostatic moiety may be repeated until the sequence of at least a portion of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection. Nucleotide incorporation and detection may be conduct for a set number of cycles or may be conducted until the primer extension reaction is complete.

FIG. 14B shows an example method for double-stranded sequencing using detectable labels, nucleic acid subunits, and reversible terminators. The detectable labels may be electrostatic moieties. The detectable labels may be reversibly coupled to the individual nucleotides 1301. The individual nucleotides may comprise reversible terminators on the 3-prime side. The second single-stranded nucleic acid may comprise random nucleic acid subunits and a primer 503. A polymerizing enzyme 502 may bind to the primer 503. The polymerizing enzyme 502 may incorporate an individual nucleotide 1301 with a electrostatic moiety and reversible terminator into the third single-stranded nucleic acid molecule. Incorporation of the individual nucleotide may displace a portion of or an entire random nucleic acid subunit. The sensor array may detect signals indicative of incorporation events after the incorporation of the individual nucleotide into the third single-stranded nucleic acid molecule. After detection of the incorporation event, the reversible electrostatic moiety may be cleaved. The reversible terminator may be removed simultaneously with or sequentially to the cleavage of the electrostatic moiety. In an example, the reversible electrostatic moiety and reversible terminator are cleaved simultaneously with a reducing agent such as DTT or TCEP. Cycles of nucleotide incorporation, nucleic acid subunit displacement, individual nucleotide detection, cleavage of the electrostatic moiety, and removal of the reversible terminator may be repeated until the sequence of at least a portion of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection. Nucleotide incorporation and detection may be conduct for a set number of cycles or may be conducted until the primer extension reaction is complete.

A target nucleic acid molecule may be sequenced and/or a length of the target nucleic acid molecule may be determined. The target nucleic acid molecule may be a fragmented nucleic acid molecule or may be a non-fragmented nucleic acid molecule. The target nucleic acid molecule may be amplified prior to detection. The target nucleic acid molecule may be amplified in solution and/or on a support. The target nucleic acid molecule amplified on a support may be immobilized to the support prior to amplification. The target nucleic acid molecule may be amplified by bridge amplification, wild fire amplification, recombinase polymerase amplification, isothermal amplification, or using any other amplification technique. Sequencing or determining a length of the target nucleic acid molecule may comprise providing a plurality of single-stranded nucleic acid molecules adjacent to a sensor array. A first single-stranded nucleic acid molecule of the plurality of single-stranded nucleic acid molecules may be disposed adjacent to a given sensor of the sensor array. The given sensor may be electrically coupled to a charge double layer (e.g., within a Debye length) containing the first single-stranded nucleic acid molecule. The first single-stranded nucleic acid molecule may be brought into contact with individual nucleotides to subject the first single-stranded nucleic acid molecule to a nucleic acid incorporation reaction. The nucleic acid incorporation reaction (e.g., primer extension reaction) may generate a second single-stranded nucleic acid molecule from the individual nucleotides. The second single-stranded nucleic acid molecule may have sequence complementarity with the first single-stranded nucleic acid molecule. At least a subset of the individual nucleotides may comprise detectable labels. A given sensor of the sensor array may be used to detect signals from the detectable labels indicative of incorporation of the individual nucleotides during or subsequent to conducting the nucleic acid incorporation reaction. The detected signals may be used to determine the sequence of the first single-stranded nucleic acid molecule.

The plurality of single stranded-nucleic acid molecules may be coupled to a plurality of supports. The plurality of supports may be a plurality of beads or a plurality of surfaces on the sensor array. In an example, the plurality of single-stranded nucleic acid molecules may be coupled to a plurality of beads and a given single-stranded nucleic acid molecule may be coupled to a given bead. The charge double layer may be adjacent to a surface of the given bead. The single-stranded nucleic acid molecule may be amplified on the surface of the bead. The amplification products may be coupled to the surface of the bead. The amplification products may form a clonal colony of single-stranded nucleic acid molecules on the surface of the bead. The clonal colony of single-stranded nucleic acid molecules may be sequenced.

In an example, the plurality of single-stranded nucleic acid molecules may be coupled to a plurality of surfaces on the sensor array and a given single-stranded nucleic acid molecule is coupled to a surface of a given sensor. The charge double layer may be adjacent to the surface of the given sensor. The single-stranded nucleic acid molecule may be amplified on the surface of the sensor. The amplification products may be coupled to the surface of the sensor. The amplification products may form a clonal colony of single-stranded nucleic acid molecules of the surface of the sensor. The clonal colony of single-stranded nucleic acid molecules may be sequenced.

A given sensor of the sensor array may comprise at least one, at least two, at least three, at least four, or more electrodes. In an example, a given sensor comprises at least two electrodes. In another example, a given sensor comprises two electrodes. The electrodes may be exposed to the solution in which the primer extension reaction takes place. Alternatively, or in addition to, the electrodes may be buried within the sensor array and, therefore, may not be exposed to the solution in which the primer extension reaction takes place. The sensor may detect signals indicative of nucleotide incorporation events. The sensor may detect the detectable label coupled to the individual nucleotides. The sensor may detect the detectable label during transient or steady state conditions. Nucleotide incorporation may be detected once, twice, three times, four times, or more than four times per incorporation cycle during steady state conditions. In an example, nucleotide incorporation may be detected at least twice per incorporation cycle during steady state conditions. The sensor array may detect electrical signals during transient or steady state conditions. The electrical signals may include, but are not limited to, changes in charge state of a molecule, changes in the conductivity of a surrounding solution, impedance signals, or changes in impedance signals. The sensor may detect a change in charge and/or conductivity or a change in impedance. The sensor may detect the change in charge and/or conductivity or impedance within a charge double layer (e.g., Debye length) of the sensor, support, or nucleic acid molecule (e.g., the sample). The detectable labels coupled to the individual nucleotides may alter the electrical environment surrounding the single-stranded nucleic acid molecules and a given sensor may detect the electrical change.

The second single-stranded nucleic acid molecule may comprise a priming site adjacent to the first-single stranded nucleic acid molecule. The priming site may be a primer with sequence complementarity with the first single-stranded nucleic acid molecule. The second single-stranded nucleic acid molecule may be generated by a primer extension reaction originating from the primer. In an example, the primer is a self-priming loop. The self-priming loop may be in a structure or looped configuration during the primer extension reaction. Subsequent to the incorporation of an individual nucleotide, the structure of the self-priming loop may be relaxed to form a linear nucleic acid molecule. Incorporation of the individual nucleotide may be detected during the relaxed, unstructured state. The self-priming loop may be relaxed by increasing the reaction temperature, changing the solution pH, changing the solution ionic strength, introducing formamide to the solution, or by any other method that denatures the nucleic acid structure.

The different types of individual nucleotides may be brought into contact with the single-stranded nucleic acid molecule sequentially (e.g., a single nucleotide at a time). Signals indicative of nucleotide incorporation may be detected after each type of individual nucleotide is brought into contact with the single-stranded nucleic acid molecule. In an example, the single-stranded nucleic acid molecule may be contacted with A nucleotides followed by the detection of signals indicative of nucleotide incorporation. The single-stranded nucleotide may then be contacted with T nucleotides followed by signal detection. The single-stranded nucleotide may then be contacted with G nucleotides followed by signal detection. The single-stranded nucleotide may be contacted with C nucleotides followed by signal detection. This cycle may repeat until the entire or a portion of the sequence of the singe-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection.

The single-stranded nucleic acid molecule may be contacted with different types of nucleotides simultaneously. For example, the single-stranded nucleic acid molecule may be contacted with all A, T, C, and G in at one time. Alternatively, or in addition two, the single-stranded nucleic acid molecule may be contacted with any combination of A, T, C, and G at one time. For example, the single-stranded nucleic acid molecule may be contacted with A and T, C and G, A and C, A and G, T and C, or T and G at one time. In an example, the single-stranded nucleic acid molecule is contacted with all A, T, C, and G simultaneously followed by signal detection to determine the sequence length or the sequence of the nucleic acid molecule. This cycle may be repeated until all or a portion of the sequence of the single-stranded nucleic acid molecule is determined.

The individual nucleotides may comprise detectable labels. The detectable labels may be reversibly or irreversibly coupled to the individual nucleotides. The detectable labels may be coupled to the nucleobase of an individual nucleotide. The individual nucleotides may comprise different types of nucleotide. In an example, the detectable labels may be electrostatic moieties. Each different type of individual nucleotide may be coupled to the same, or a single, type of detectable label. Each different type of individual nucleotide may be coupled to the same type of detectable label by a different coupling mechanism. The detectable label may be selectively coupled to or cleaved from an individual nucleotide. For example, an individual nucleotide may comprise a detectable label when contacted with the single-stranded nucleic acid molecule. After incorporation the signal of the individual nucleotide may be detected and generate a positive signal (e.g., a signal is detected). The detectable label may be removed under a given cleavage condition. After removal of the detectable label the incorporated nucleotide may generate a null signal (e.g., no signal is detected). In an example using a double read sequencing approach (see FIG. 9), an individual nucleotide may have a positive/null signal, positive/positive signal, a null/null signal, or a null/positive signal. In an example, a single-stranded nucleic acid molecule may be contacted with four different types of nucleotides simultaneously and a polymerizing enzyme may facilitate nucleotide incorporation. Each of the nucleotides may have the same or a different detectable label. In an example, each type of nucleotide has a different detectable label and the sequence of the nucleic acid molecule is detected. In another example, each type of nucleotide has the same detectable label and the length of the nucleic acid molecule is detected. After nucleotide incorporation, signals indicative of nucleotide incorporation may be measure. The incorporated nucleotides may generate a variety of positive and null signals. The single-stranded nucleic acid molecules may be treated with a cleavage and/or coupling condition. After treatment with the cleavage and/or coupling condition, signals indicative of nucleotide incorporation may again be measured. The incorporated nucleotides may generate a variety of positive and null signals. The pattern of positive and null signals may be used to determine which type of nucleotide was incorporated into the second single-stranded nucleic acid molecule. After the second detection cycle, the electrostatic moieties may be removed using a second cleavage condition.

In an example, each different individual nucleotide may be coupled to a different detectable label. The detectable labels may be electrostatic moieties. The electrostatic moieties may include polyanion, polycation, or neutral electrostatic moieties. The single-stranded nucleic acid molecule may be contacted with the different nucleotides sequentially or simultaneously. In an example, the single-stranded nucleic acid molecules may be contacted with the different individual nucleotides simultaneously and each individual nucleotide of the different individual nucleotides may be coupled to a different electrostatic moiety. A polymerizing enzyme may facilitate incorporation of the individual nucleotides into the second single-stranded nucleic acid molecule. After incorporation of the individual nucleotides, the sensor array may detect the signals indicative of individual nucleotide incorporation. The different individual nucleotides may generate signals representing the different charge groups and signals representing different magnitudes of charge respective to the electrostatic moiety to which they are coupled. The detectable label may be removed after signal detection.

The individual nucleotides may comprise reversible terminators, detectable labels, and both reversible terminators and detectable labels. The reversible terminator may be coupled to the 3-prime side of an individual nucleotide. The reversible terminator may prevent additional nucleotides from stably hybridizing to the first single-stranded nucleic acid molecule. The reversible terminator may be removed after detection of signals indicative of nucleotide incorporation. Removal of the reversible terminator may permit incorporation of subsequent nucleotides. In an example, a single-stranded nucleic acid molecule may be contacted with different individual nucleotides comprising different detectable moieties and reversible terminators simultaneously. A polymerizing enzyme may facilitate incorporation of a single individual nucleotide into a second single-stranded nucleic acid molecule. The sensor may detect signals indicative of nucleotide incorporation. Following signal detection, the detectable label and reversible terminator may be removed either simultaneously or sequentially. This cycle may be repeated until the sequence of all or part of the first single-stranded nucleic acid molecule is determined.

The cleavage of the detectable label may leave a scar on the individual nucleotide after cleavage. The scar may comprise portions of the detectable label that are not fully removed during cleavage of the label. In an example, the scar may reduce the efficiency of the polymerizing enzyme. In an example, the scar may inhibit the polymerizing enzyme. Pyrophosphorolysis mediated terminator exchange (PMTE) sequencing may reduce the amount of scar build up during sequencing.

A target nucleic acid molecule may be sequenced and/or a length of the target nucleic acid molecule may be determined. The target nucleic acid molecule may be a fragmented nucleic acid molecule or may be a non-fragmented nucleic acid molecule. The target nucleic acid molecule may be amplified prior to detection. The target nucleic acid molecule may be amplified in solution and/or on a support. The target nucleic acid molecule amplified on a support may be immobilized to the support prior to amplification. The target nucleic acid molecule may be amplified by bridge amplification, wild fire amplification, recombinase polymerase amplification, isothermal amplification, or using any other amplification technique. Sequencing or determining a length of the target nucleic acid molecule may comprise providing a plurality of single-stranded nucleic acid molecules adjacent to a sensor array. A first single-stranded nucleic acid molecule of the plurality of single-stranded nucleic acid molecules may be disposed adjacent to a given sensor of the sensor array. The first single-stranded nucleic acid molecule may be subjected to a nucleic acid incorporation reaction to generate a second single-stranded nucleic acid molecule. The nucleic acid incorporation reaction may comprise alternately and sequentially incorporating individual nucleotide of a first plurality of nucleotide comprising delectable labels and followed by incorporation of a second plurality of individual nucleotides without detectable labels. The nucleic acid incorporation reaction may comprise alternately and sequentially incorporating individual nucleotide of a first plurality of nucleotide comprising delectable labels and exchanging (e.g., removal of the first nucleotide) the first plurality of individual nucleotides with individual nucleotides of a second plurality of individual nucleotides without detectable labels. The first plurality of nucleotides may be covalently incorporated into the growing nucleic acid strand or may be transiently bound (e.g., not covalently bound) to the growing nucleic acid strand. The second plurality of individual nucleotides may not comprise detectable labels. The given sensor may detect signals from the detectable labels while or subsequent to conducting the nucleic acid incorporation reaction. The detected signals may be generated from the detectable labels and may be indicative of incorporation of the first plurality of individual nucleotides into the second single-stranded nucleic acid molecule, thereby determining a sequence of the first single-stranded nucleic acid molecule.

The plurality of single stranded-nucleic acid molecules may be coupled to a plurality of supports. The plurality of supports may be a plurality of beads. In an example, the plurality of single-stranded nucleic acid molecules may be coupled to a plurality of beads and a given single-stranded nucleic acid molecule may be coupled to a given bead. A given sensor may be electrically coupled to a charge double layer comprising the first single-stranded nucleic acid molecule. The charge double layer may be adjacent to a surface of the given bead. The single-stranded nucleic acid molecule may be amplified on the surface of the bead. The amplification products may be coupled to the surface of the bead. The amplification products may form a clonal colony of single-stranded nucleic acid molecules on the surface of the bead. The clonal colony of single-stranded nucleic acid molecules may be sequenced.

In an example, the plurality of single-stranded nucleic acid molecules may be coupled to a plurality of surfaces on the sensor array and a given single-stranded nucleic acid molecule is coupled to a surface of a given sensor. A given sensor may be electrically coupled to a charge double layer comprising the first single-stranded nucleic acid molecule. The charge double layer may be adjacent to the surface of the given sensor. The single-stranded nucleic acid molecule may be amplified on the surface of the sensor. The amplification products may be coupled to the surface of the sensor. The amplification products may form a clonal colony of single-stranded nucleic acid molecules of the surface of the sensor. The clonal colony of single-stranded nucleic acid molecules may be sequenced and/or a length of the single-stranded nucleic acids may be determined.

A given sensor of the sensor array may comprise at least one, at least two, at least three, at least four, or more electrodes. In an example, a given sensor comprises at least two electrodes. In another example, a given sensor comprises two electrodes. The electrodes may be exposed to the solution in which the primer extension reaction takes place. Alternatively, or in addition to, the electrodes may be buried within the sensor array and, therefore, may not be exposed to the solution in which the primer extension reaction takes place. The sensor may detect signals indicative of nucleotide incorporation events. The sensor may detect the detectable label coupled to the individual nucleotides. The sensor may detect the detectable label during transient or steady state conditions. Nucleotide incorporation may be detected once, twice, three times, four times, or more than four times per incorporation cycle during steady state conditions. In an example, nucleotide incorporation may be detected at least twice per incorporation cycle during steady state conditions. The sensor array may detect electrical signals during transient or steady state conditions. The electrical signals may include, but are not limited to, changes in charge state of a molecule, changes in the conductivity of a surrounding solution, impedance signals, or changes in impedance signals. The sensor may detect a change in charge and/or conductivity or a change in impedance. The sensor may detect the change in charge and/or conductivity or impedance within a charge double layer (e.g., Debye length) of the sensor, support, or nucleic acid molecule (e.g., the sample). The detectable labels coupled to the individual nucleotides may alter the electrical environment surrounding the single-stranded nucleic acid molecules and a given sensor may detect the electrical change.

The second single-stranded nucleic acid molecule may comprise a priming site adjacent to the first-single stranded nucleic acid molecule. The priming site may be a primer with sequence complementarity with the first single-stranded nucleic acid molecule. The second single-stranded nucleic acid molecule may be generated by a primer extension reaction originating from the primer. In an example, the primer is a self-priming loop. The self-priming loop may be in a structure or looped configuration during the primer extension reaction. Subsequent to the incorporation of an individual nucleotide, the structure of the self-priming loop may be relaxed to form a linear nucleic acid molecule. Incorporation of the individual nucleotide may be detected during the relaxed, unstructured state. The self-priming loop may be relaxed by increasing the reaction temperature, changing the solution pH, changing the solution ionic strength, introducing formamide to the solution, or by any other method that denatures the nucleic acid structure.

The first plurality of nucleotides may comprise a terminator that prevents an additional nucleotide from stably hybridizing to the first single-stranded nucleic acid molecule. The terminator may be a reversible terminator or an irreversible terminator. In an example, the terminator is an irreversible terminator. The terminator may reduce the occurrence of homopolymers and/or the incorporation of multiple individual nucleotides per incorporation cycle. The first plurality of individual nucleotides may comprise dideoxynucleotides (ddNTP) or 3-fluorodeoxynucleotides. The ddNTP may be a chain-elongating inhibitor. The first plurality of nucleotides may comprise detectable labels. The detectable labels may not be removed after detection of nucleotide incorporation. The detectable labels may be electrostatic moieties, fluorescent labels, chemiluminescent labels, colorimetric labels, radio labels, or any other detectable label. In an example, the detectable labels are electrostatic moieties. The detectable labels may be coupled to the nucleobases of the first plurality of nucleotides.

The first plurality of nucleotides may comprise different types of nucleotides. In an example, the different types of nucleotides may be coupled to different types of detectable labels. Each individual type of nucleotide may be coupled to an individual type of detectable label. The first single-stranded nucleic acid molecule may be contacted with all the different types of nucleotides simultaneously. The sensor array may then detect the different detectable electrostatic moieties coupled to the different individual nucleotides. Alternatively, or in addition to, each type of nucleotide may have the same detectable label and the sensor may detect the addition of a nucleotide without resolving the different nucleotides (e.g., determine a sequence length). In this example, a single read may be used per incorporation cycle. In an example, each type of individual nucleotide may be coupled to the same detectable label. The first single-stranded nucleic acid molecule may be contacted with each type of nucleotide sequentially (e.g., contacted with one type of nucleotide, followed by contact with another type of nucleotide). After incorporation of a nucleotide of one type, the sensor array may detect signals indicative of nucleotide incorporation. The first single-stranded nucleic acid molecule may then be contacted with a different type of nucleotide. The detectable label may not be cleaved from the first plurality of nucleotides (e.g., the detectable label may be irreversible).

The first plurality of individual nucleotides may be exchanged for a second plurality of individual nucleotides. The exchange reaction may be accomplished by driving the polymerization reaction in reverse with an excess of pyrophosphate, triphosphate, or tetraphosphate. The second plurality of individual nucleotides may not comprise detectable labels. Exchanging the first plurality of individual nucleotides for the second plurality of individual nucleotide may reduce scar formation. The second plurality of individual nucleotides may comprise reversible terminators. The reversible terminators may be reversed by contact with a reducing agent, by changing solution pH, by changing solution ionic strength, by contact with ionic surfactants, or by any other terminator removal method.

Figure 15:
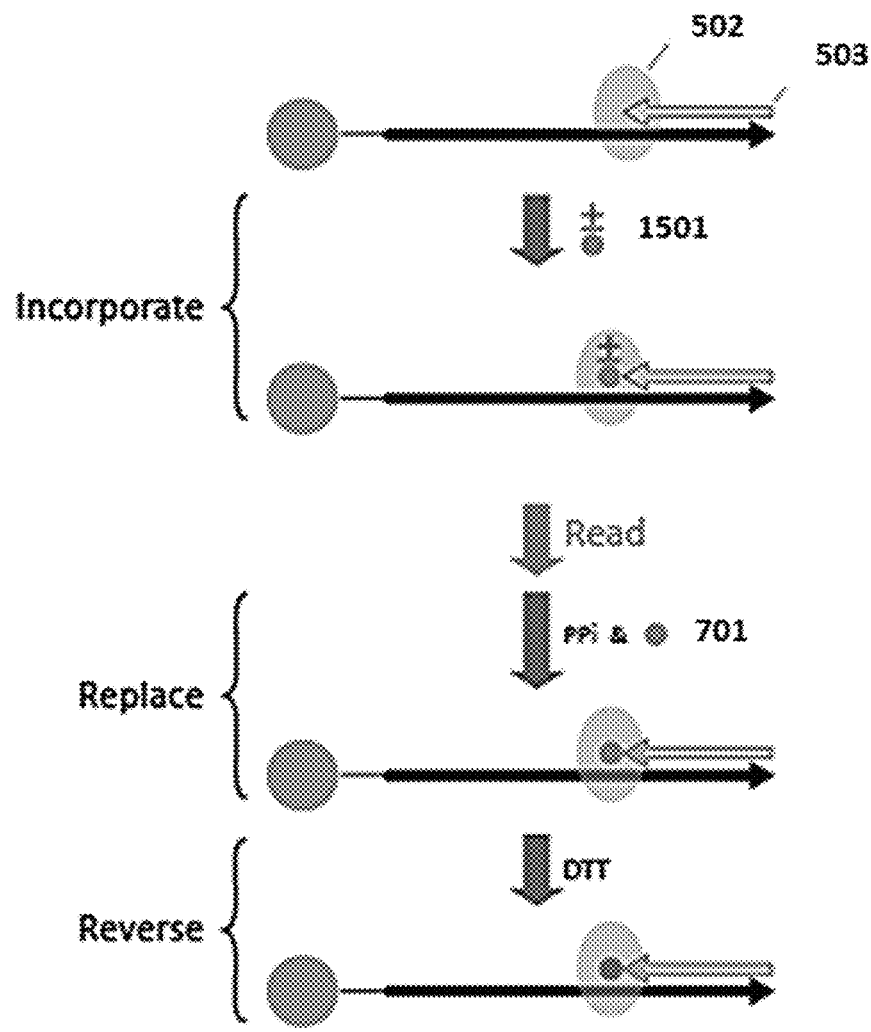
FIG. 15 shows an example method for pyrophosphorolysis mediated terminator exchange sequencing.

FIG. 15 shows an example PMTE sequencing method. A first single-stranded nucleic acid molecule may be coupled to a bead. The first single-stranded nucleic acid molecule may have a priming site. The priming site may be complementary to a portion of the first single-stranded nucleic acid molecule. The first single-stranded nucleic acid molecule may be contacted with a first plurality of individual nucleotides 1501. The first plurality of individual nucleotides 1501 may comprise single type of nucleotide. The first plurality of individual nucleotides 1501 may comprise an irreversible terminator and an irreversible detectable electrostatic moiety. The irreversible detectable electrostatic moiety may be the same for each different type of nucleotide. A polymerizing enzyme 502 may facilitate incorporation of the first individual nucleotide 1501 into a second single-stranded nucleic acid molecule. A given sensor may detect the presence or absence of nucleotide incorporation via the presence or absence of the detectable label. The first plurality of individual nucleotides 1501 may then be exchanged for a second plurality of individual nucleotides 701. The second plurality of individual nucleotides 701 may be the same type of nucleotides as the first plurality 1501. The second plurality of individual nucleotides 701 may not have a detectable label and may have a reversible terminator. After incorporation of the second plurality of individual nucleo-tides into the second single-stranded nucleic acid molecule the reversible terminator may be removed or reversed. The terminator may be reversed by a reducing agent. This cycle may be repeated until the sequence of all or a part of the first single-stranded nucleic acid molecule is determined. The method may include performing greater than or equal to 1, 2, 3, 4, 6, 8, 10, 12, 15, 20, 25, 30, 40, 50, 75, 100, 125, 150, 200, 250, 300, 400, 500, 600, 700, 800, 900, 1000, 1500, or more cycles of nucleotide incorporation and detection.

In an example (see FIG. 15), a first single-stranded nucleic acid molecule may be coupled to a bead. The first single-stranded nucleic acid molecule may have a priming site coupled to a primer 502. The priming site may be complementary to a portion of the first single-stranded nucleic acid molecule. The first single-stranded nucleic acid molecule may be contacted with a first plurality of individual nucleotide. The first plurality of individual nucleotides 1501 may comprise multiple different types of nucleotides. The first plurality of individual nucleotides 1501 may comprise an irreversible terminator and an irreversible detectable electrostatic moiety. The irreversible detectable electrostatic moiety may be different for each type of individual nucleotide. A polymerizing enzyme 502 may facilitate incorporation of the first individual nucleotide 1501 into a second single-stranded nucleic acid molecule. A given sensor may detect the type of nucleotide incorporated into the second single-stranded nucleic acid molecule via the type of the detectable label present at the sensor. The first plurality of individual nucleotides 1501 may then be exchanged for a second plurality of individual nucleotides 701. The second plurality of individual nucleotides 701 may include same types of nucleotides as the first plurality. The second plurality of individual nucleotides 701 may not have detectable labels and may have a reversible terminator. After incorporation of the second plurality of individual nucleotides into the second single-stranded nucleic acid molecule the reversible terminator may be removed or reversed. The terminator may be reversed by a reducing agent. This cycle may be repeated until the sequence of all or a part of the first single-stranded nucleic acid molecule is determined.

The PMTE sequencing approach described above may be used in combination with a double-stranded sequencing method. For example, a double-stranded nucleic acid molecule comprising a first and a second single-stranded nucleic acid molecule may be contacted with a polymerizing enzyme. The polymerizing enzyme may incorporate an individual nucleotide comprising an irreversible terminator and a detectable label into a third single-stranded nucleic acid molecule. Incorporation of the individual nucleotide may generate a flap. The flap may be cleaved before or after detection of individual nucleotide incorporation. The double-stranded nucleic acid molecule may be contacted with the different types of individual nucleotides simultaneously or sequentially. The different types of individual nucleotides may comprise the same or different detectable label. After incorporation of the individual nucleotides the incorporation event may be detected by the sensor array. After detection, the individual nucleotide comprising the detectable label and irreversible terminator may be exchanged for an individual nucleotide comprising a reversible terminator. The reversible terminator may then be reversed to allow for incorporation of subsequent individual nucleotides.

The method may further comprise monitoring and/or correcting for phase error. A nucleic acid molecule with phase error may be extended more or less than the consensus state (e.g. reference sequence) of a clonal population for which the nucleic acid molecule is a member of or a template nucleic acid molecule for which the nucleic acid molecule is a copy or representative sequence of. For fragments including a base incorporated incorrectly (e.g., an extra base or incorrect base added to the growing strand), this phase error may be considered to be leading. For other nucleic acid molecules where a base is not incorporated into the growing strand relative to a consensus sequence, the polynucleotide can be considered to be lagging. As polymerases may be imperfect, some phase error can occur within a colony that has a long extension reaction as a part of a colony based sequencing process. Phase error may limit the read lengths of commercial clonal sequencing systems.

Phase errors may lead to leading sequencing incorporation errors. Leading sequencing error may refer to sequences that are longer than the dominant sequence due to incorrect or excess (e.g., homopolymer) additions of nucleotides. The incorrect or excess additions may result from polymerase errors, particularly when high concentrations of dNTPs are used in a noncompetitive reaction. Alternatively or in addition to, the leading sequencing incorporation error may result from inadequate washing or nonspecific binding of dNTPs, which may be subsequently released and incorporated. Leading sequencing incorporation errors may result from the incorporation of nucleotides without effective 3' terminators, thereby causing the incorporation event to proceed one cycle ahead. For example, leading sequencing incorporation errors may be caused by the presence of a trace amount of unprotected or unblocked 3'-OH nucleotides during a nucleic acid incorporation event. The unprotected 3'-OH nucleotides may be generated during the manufacturing processes or possibly during storage and reagent handling processes.

Phase errors may lead to lagging sequencing errors. Lagging sequencing incorporation errors may refer to sequences that are shorter than the dominant sequence through missed additions of the correct nucleotide. Lagging sequencing errors may occur due to non-optimal reaction conditions, steric hindrance, secondary structure, or other sources of polymerase inhibition. Non-limiting examples of processes that may cause lagging sequencing errors include: incomplete removal of the reversible terminators, detectable labels, a flap derived from a second single-stranded nucleic acid molecules, modified nucleotides, and/or linkers. Longer cycle times can allow more opportunities for the polymerase to incorporate the wrong nucleotide. Similarly, less accessible nucleic acid molecules (e.g., DNA) may result in inadequate opportunities to incorporate the correct nucleotide. It is anticipated that temperature, step times, polymerase selection, nucleotide concentration, salt concentration and buffer selection may be optimized to minimize incorporation errors.

For example, a nucleic acid (e.g., DNA) sample may have a sequence of TGTTC in a first region after a region which is complementary to a primer. A fluidic cycle may first introduce deoxycytidine triphosphate (dCTP), secondly followed by deoxythymidine triphosphate (dTTP), thirdly followed by deoxyadenosine triphosphate (dATP), and fourthly followed by deoxyguanosine triphosphate (dGTP), interspersed with wash steps. In the first part of a fluidic cycle, dCTP molecules which flow in as part of the first cycle may not be properly washed out and away from the nucleic acid template. In a second part of a fluidic cycle, dTTP molecules which flow in as part of the second cycle may not be properly washed out a well structure. During the first and second part of the first fluidic cycle, dNTPs may not be incorporated. During a third part of a fluidic cycle, dATPs may be introduced and may be incorporated, as dATP is complementary to T, the first base of the sample. Any nonspecifically bound dCTP molecules which cease to be nonspecifically bound may also be incorporated during this third portion of a fluidic cycle. These unbound dCTP molecules may be incorporated subsequent to incorporation of a dATP molecule. Subsequent to incorporation of a dCTP molecule, two more dATP molecules may be incorporated, which may result in some of the molecules of a monoclonal bead having leading sequencing phase errors. Thus some molecules of a monoclonal bead may become out of phase.

Phase errors may be detected by comparing sequences of a plurality of double- or single-stranded molecules from a clonal population and/or by comparing with a reference sequence. For example, sequences may be analyzed for miscalls, such as substitution-type or indel-type miscalls. Miscalls may be detected by measuring signal intensities during nucleic acid incorporation reaction using single-stranded molecules as templates for generating complementary single-stranded molecules. The double- or single-stranded molecules may comprise a clonal population. In an example, a portion of the clonal population may have substantially low detectable signal intensity, such as less than threshold, compared to the rest of the clonal population. This may indicate that the nucleotides may be incorporated in fewer than all of the available positions and may result in indel-type miscall. Indel-type miscalls may be caused by the incomplete extension of the single-stranded molecules and may lead to lagging sequencing errors. In another example, a portion of the clonal population may have a substituted base when compared to a reference sequence. Substitution-type miscalls may be caused by leading sequencing errors due to incorporation of an additional nucleotide in nucleic acid incorporation reaction. The additional nucleotide may be different than the nucleotide in the reference sequence.

Phase errors may be reduced by carrying out nucleic acid incorporation reaction in competitive conditions. For example, concentration of nucleotides may be reduced in order to mitigate leading sequencing errors. In another example, cycle time and/or number of cycles may be reduced for each read in order to avoid wrong incorporation of nucleotides causing leading sequencing errors. In some cases, phase errors may be reduced by using polymerizing enzymes based on the nucleotides. For example, Type A polymerase, such as Bst polymerase, may be used when incorporating unmodified nucleotides in order to reduce phase errors. Type B polymerase, such as Terminator IX™ (NEB), may be used when incorporating modified nucleotides in order to reduce phase errors.

In an aspect, phase errors may be reduced by incorporating unmodified nucleotides, subsequently or simultaneously, with modified nucleotides in a nucleic acid incorporation reaction.

A method for nucleic acid sequencing may comprise providing a plurality of double- or single-stranded nucleic acid molecules adjacent to a sensor array. A first double- or single-stranded nucleic acid molecule of the plurality of single-stranded nucleic acid molecules may be disposed adjacent to a given sensor of the sensor array.

The first single-stranded nucleic acid molecule may be subjected to a nucleic acid incorporation reaction to generate a second single-stranded nucleic acid molecule as a growing strand complementary to the first single-stranded nucleic acid molecule. The nucleic acid incorporation reaction may comprise alternately and sequentially (i) incorporating individual nucleotides of a first plurality of nucleotides comprising detectable labels, and (ii) incorporating individual nucleotides of a second plurality of nucleotides that do not comprise detectable labels. The given sensor may be used to detect signals from the detectable labels which may be indicative of incorporation of the individual nucleotides of the first plurality of nucleotides into the second single-stranded nucleic acid molecule, thereby determining a sequence of the first single-stranded nucleic acid molecule. The first plurality of nucleotides may be exchanged with the second plurality of nucleotides. The incorporation of the second plurality of nucleotides may correct phase error. The incorporation of the second plurality of nucleotides may correct phase error by incorporating an individual nucleotide from the second plurality of nucleotides at a location along the first single-stranded nucleic acid molecule in which an individual nucleotide from the first plurality of nucleotides has not been incorporated. The nucleic acid incorporation reaction may be continued by using the individual nucleotides from the first plurality of nucleotides. The first single-stranded nucleic acid molecule may have sequence homology to a template single-stranded nucleic acid molecule.

Figure 20:
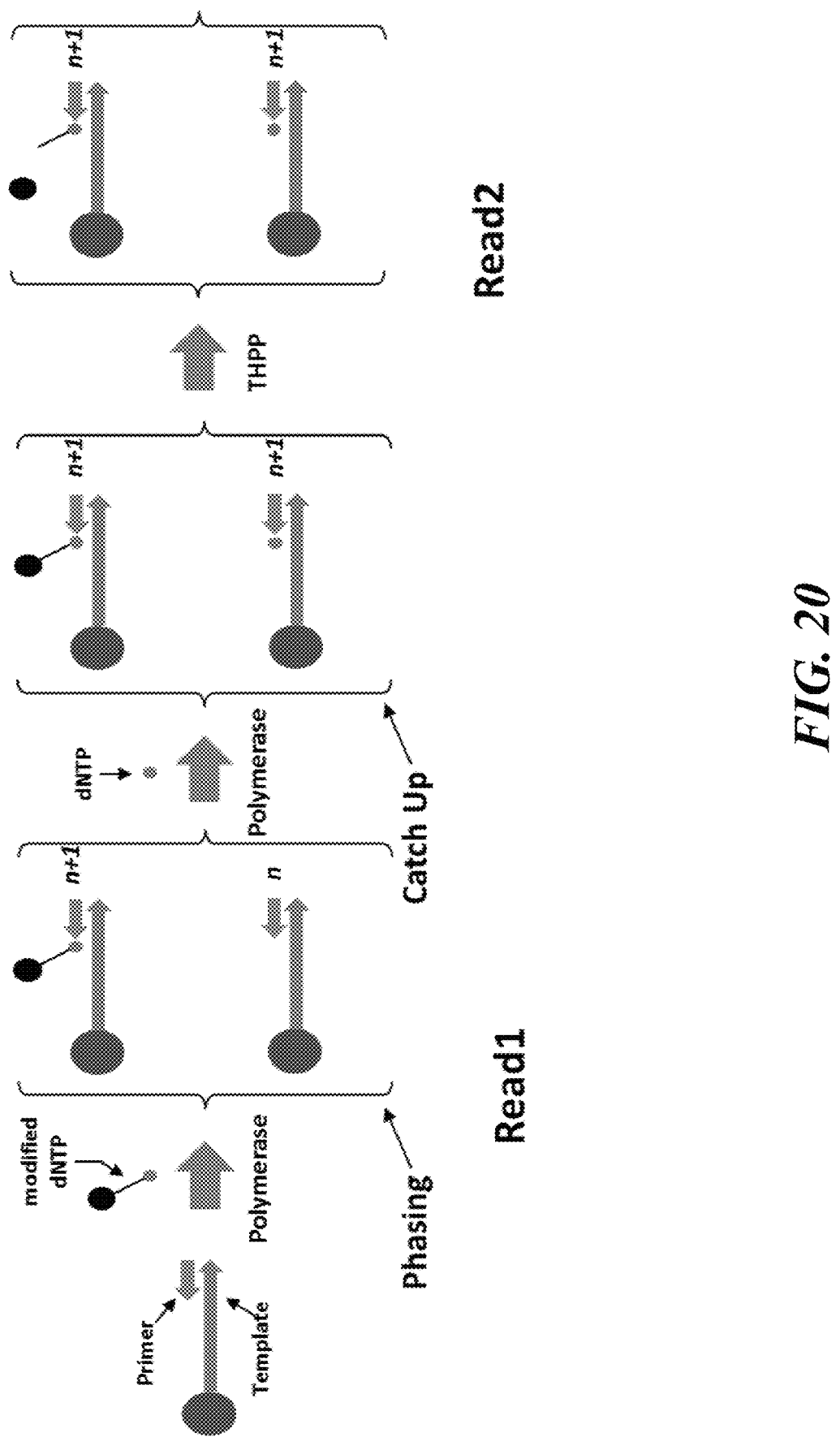
FIG. 20 illustrates a method for correcting phase error during a sequencing reaction.

An example of a method for nucleic acid sequencing in order to correct phase error is illustrated in FIG. 20. A plurality of single-stranded nucleic acid molecules may be coupled to a bead. The plurality of single-stranded nucleic acid molecules may comprise a clonal population of a given single-stranded nucleic acid molecule. A first single-stranded nucleic acid molecule may have priming sites coupled to individual primers. The priming site may be complementary to a portion of the first single-stranded molecule. The first single-stranded molecule may be contacted with a first plurality of individual nucleotides. The first plurality of individual nucleotides may comprise multiple different types of nucleotides. The first plurality of individual nucleotides may comprise single type of nucleotide. The first plurality of individual nucleotides may be modified nucleotides. The first plurality of individual nucleotides may comprise an irreversible terminator and an irreversible detectable electrostatic moiety. The irreversible detectable electrostatic moiety may be different for each type of individual nucleotide. A polymerizing enzyme may facilitate incorporation of the first individual nucleotide into a second single-stranded nucleic acid molecule. A given sensor may detect the type of nucleotide incorporated into the second single-stranded nucleic acid molecule via the type of the detectable label present at the sensor. The first plurality of individual nucleotides may then be exchanged for a second plurality of individual nucleotides. The second plurality of individual nucleotides may include same types of nucleotides as the first plurality. The second plurality of individual nucleotides may not have detectable labels and may have a reversible terminator. The addition of the second plurality of nucleotides may correct phase error by incorporating an individual nucleotide from the second plurality of nucleotides at a location along the first single-stranded nucleic acid molecule in which an individual nucleotide from the first plurality of nucleotides has not been incorporated.

As shown in FIG. 20, the phase error can be a leading sequencing error as indicated by the addition of an extra nucleotide (n+1) in a leading second single-stranded molecule in Read1. An individual nucleotide from the second plurality of nucleotides may be incorporated into a lagging second single-stranded molecule, such that the lagging molecule may be in sync with the leading molecule, as indicated by "n+1" in the next cycle before Read2. After incorporation of the second plurality of individual nucleotides into the second single-stranded nucleic acid molecule the reversible terminator may be removed or reversed. The terminator may be reversed by a reducing agent. Once both the molecules may be synced-in with the same number of incorporated nucleotides that is (n+1), the nucleic acid incorporation reaction may be continued using the individual nucleotides from the first plurality of nucleotides. In the next cycle, Read2, the detectable label in the first plurality of nucleotides may be cleaved for detection by a sensor. The detectable label may be cleaved by using a phosphate reagent, such as tris(hydroxypropyl)phosphine (THPP). The cleavage of the detectable label may leave a scar on the individual nucleotide after cleavage. The scar may comprise portions of the detectable label that are not fully removed during cleavage of the label. The first single-stranded nucleic acid molecule may be alternately provided with the first plurality of individual nucleotides and the second plurality of individual nucleotides to generate the second single-stranded nucleic acid molecule until the sequence of all or a part of the first single-stranded nucleic acid molecule is determined.

Figure 21:
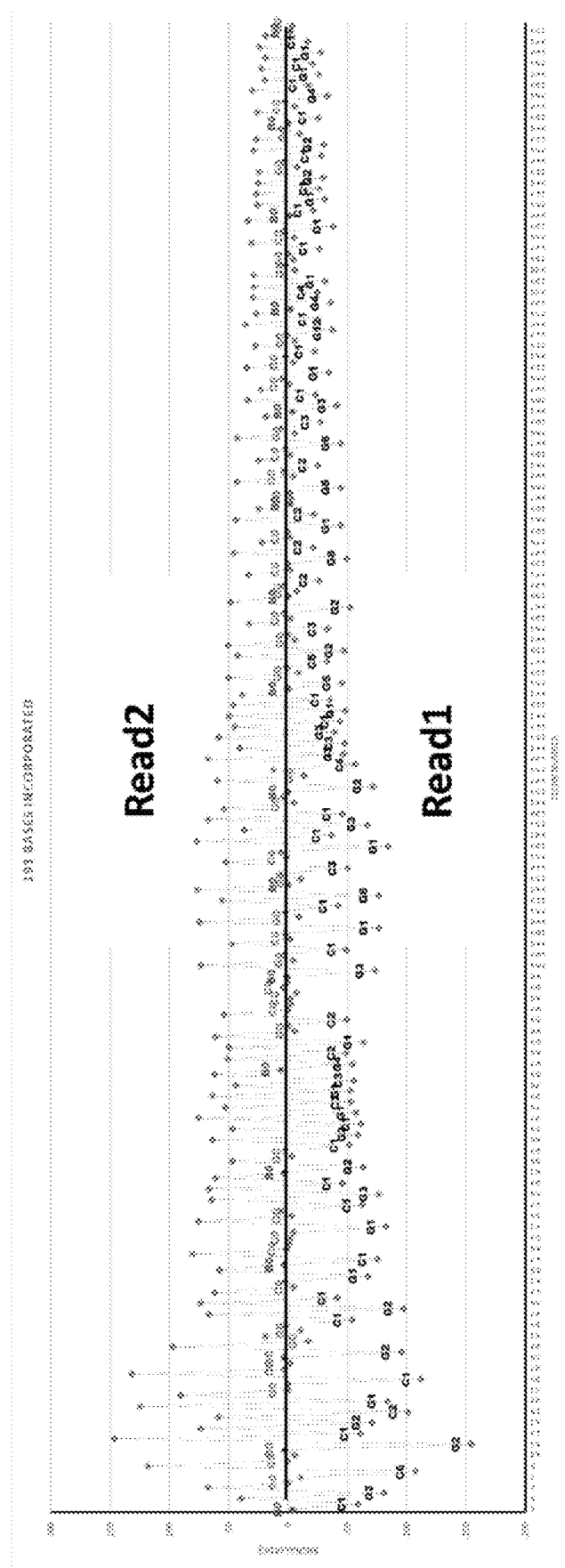
FIG. 21 is an example of a method for correcting phase error.
Figure 22:
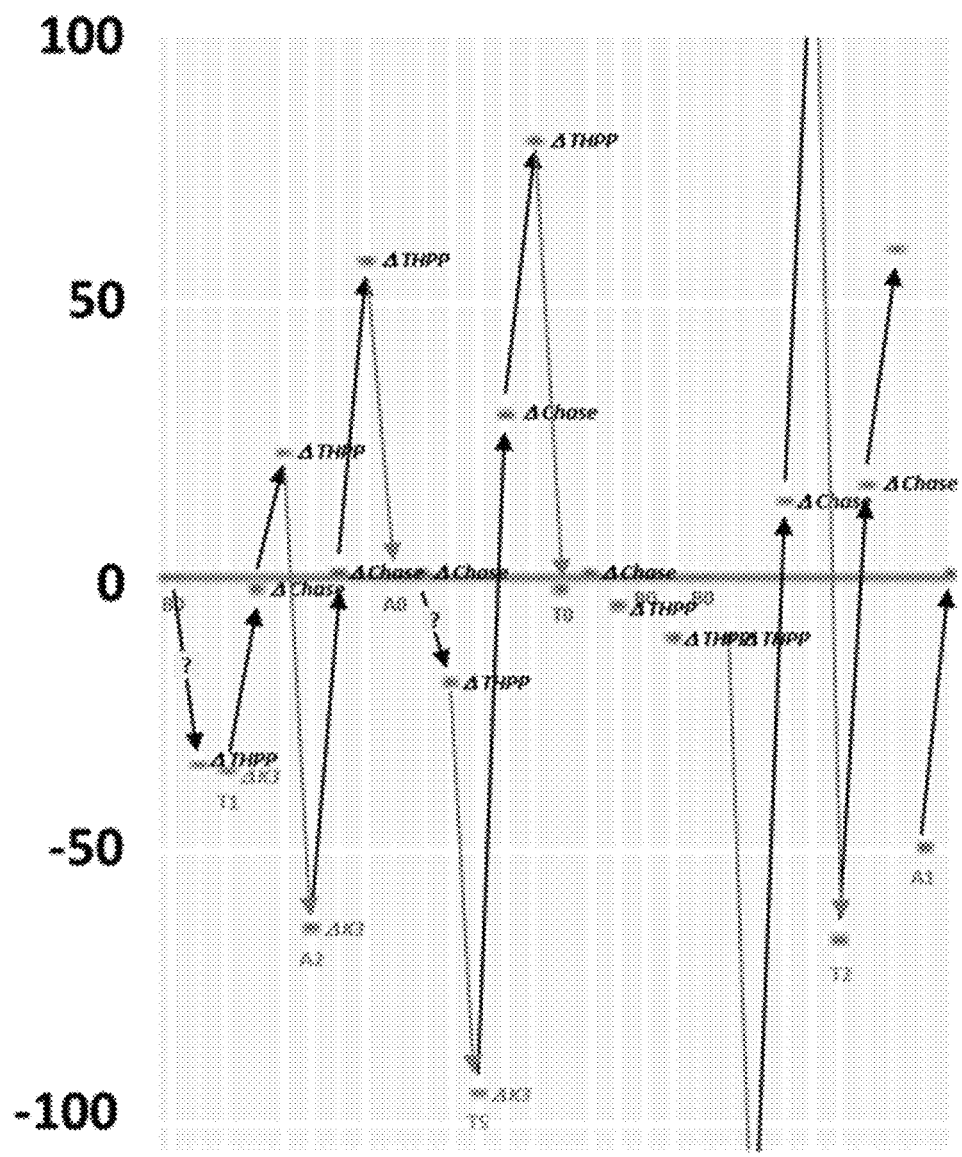
FIG. 22 is another example of a method for correcting phase error.

FIGS. 21 and 22 show example results of using the method for reducing phase error during nucleic acid sequencing. A first single-strand molecule may be contacted with a first plurality of nucleotides with a detectable label, such as three lysine amino acid residues, in order to generate a second single-strand molecule. The first plurality of nucleotides may be exchanged with a second plurality of nucleotides. The incorporation of the first plurality of nucleotides may cause a leading phase error (n+1) in the second single-strand molecule in Read1. The phase error may be corrected by incorporating the second plurality of nucleotides in the lagging molecules such that the lagging molecules may be in-sync with leading molecules. As shown in FIG. 21, X-axis shows flow number corresponding to the number of nucleotides incorporated and Y-axis shows signal derived from cleaving of the detectable label. In Read1, the detectable label may be coupled to the first plurality of nucleotides which may result in a negative signal on the Y-axis. The negative signal may be due to the displacement of cations, such as $Mg^{2+}$, by the lysine residues of the detectable label. In Read2, the detectable label may be cleaved from the first plurality of nucleotides resulting in a positive signal on the Y-axis derived from the scarred nucleotides. The positive signal may be derived from the concentration of cations, such as $Mg^{2+}$, upon removal of the detectable label comprising lysine residues. In both Read1 and Read2, the second plurality of individual nucleotides may not have detectable labels, which may result in a signal close to zero on the Y-axis. The changes in signals during the sequencing process are shown in FIG. 22. The presence of a detectable label, three lysine residues, in the first plurality of nucleotides may result in a net negative signal on the Y-axis, as indicated by delta K3 in Read1. Addition of the unmodified nucleotides may result in a neutral signal, close to zero on the Y-axis as indicated by delta chase in Read2. Cleavage of the detectable label by THPP may result in a surge of a net positive signal as indicated by delta THPP in Read3. Upon cleavage of the detectable label, the neutral signal due to the unmodified nucleotides may shift to a positive signal as indicated by arrows during delta chase. The positive signal may be due to negative phosphate groups in the nucleotides, in turn, may concentrate $Mg2^+$ cations which may produce a net positive signal.

Systems for Nucleic Acid Sequencing

The present disclosure provides a system for nucleic acid sequencing that may include various components. The system may be used in various applications, such as sequencing a nucleic acid sample from a living subject. For example, a sensor array with sites occupied by beads or with sites directly occupied by a plurality of nucleic acid templates comprising clonal populations may be contacted with a fluid comprising a primer(s) that hybridize to clonal nucleic acids. The sensor array may then be washed and contacted with a fluid comprising one or more types of nucleotides, polymerizing enzymes, and/or any co-factors in a suitable buffer. The array may then be washed and the incorporated nucleotides may be detected. The incorporate, wash, detect cycle may be repeated until sample nucleic acids bound to the bead or bound to a surface of the sensor have been sequenced.

The sensor array may be incorporated into an integrated sequencing platform. An integrated sequencing platform may include one or more of a nucleic acid (e.g., DNA) extraction module, a library construction module, an amplification module, an extraction module, and a sequencing module. In some embodiments the systems may be separate and/or in modular format. In some embodiments, the integrated sequencing platform can include one, two, three, four, or all five of these systems. In some cases, the modules can be integrated within a single unit (e.g., a microfluidic device), a single array (e.g., a sensor array that may be re-usable) or even a single device. Examples of integrated sequencing platforms can be found in PCT Patent Application No. PCT/US2011/054769, PCT Patent Application No. PCT/US2012/039880, PCT Patent Application No. PCT/US2012/067645, PCT Patent Application No. PCT/US2014/027544, PCT Patent Application No. PCT/US2014/069624 and PCT Patent Application No. PCT/US2015/020130, each of which is entirely incorporated herein by reference.

In another aspect, the present disclosure provides a system for nucleic acid sequencing. The system may comprise a sensor array comprising a plurality of individual sensors. During use a given double-stranded nucleic acid molecule of a plurality of double-stranded nucleic acid molecules may be disposed adjacent to a given sensor of the sensor array. The given double-stranded nucleic acid molecule may comprise a first single-stranded nucleic acid molecule and a second-single stranded nucleic acid molecule. The given sensor may be electrically coupled to a charge double layer (e.g., within a Debye length of) the given double-stranded nucleic acid molecule. The system may further comprise one or more computer processors that are operatively coupled to the sensor array. The one or more computer processors may be programmed to bring a non-hybridized segment of the first single-stranded nucleic acid molecule in contact with individual nucleotides to subject the non-hybridized segment to a nucleic acid incorporation reaction that generates a third single-stranded nucleic acid molecule for the individual nucleotides. The third single-stranded nucleic acid molecule may have sequence complementarity with the first single-stranded nucleic acid molecule. During or subsequent to the nucleic acid incorporation reaction, the given sensor may detect signals indicative of incorporation of the individual nucleotides not the third single-stranded nucleic acid molecule, thereby determining a sequence of the non-hybridized segment.

The double-stranded nucleic acid molecule may be coupled to a support. The support may be a bead or a surface of the sensor array. A plurality of double-stranded nucleic acid molecules may be coupled to a plurality of beads or a plurality of locations on the surface of the sensor array. Each bead of the plurality of beads may be disposed adjacent to a given sensor. The plurality of beads may be magnetic or non-magnetic beads. The beads may have a surface coating that facilitates coupling of the double-stranded nucleic acid molecule to the bead. The charge double layer (e.g., Debye length) may be adjacent to the surface of the bead. Alternatively, or in addition to, the plurality of double-stranded nucleic acid molecules may be coupled to one or more surfaces of the sensor array. A given double-stranded nucleic acid molecule may be coupled to a surface of a given sensor. The charge double layer (e.g., Debye length) may be adjacent to the surface of the given sensor. The double-stranded nucleic acid molecule coupled to the bead or surface of the sensor array may be clonally amplified prior to sequencing so that each bead is coupled to a clonal population of double-stranded nucleic acid molecules or so that each surface of a given sensor is coupled to a clonal population of double-stranded nucleic acid molecules.

A given sensor may comprise at least one, at least two, at least three, or at least four electrodes. In an example, a given sensor comprises at least two electrodes. The electrodes of a given sensor may detect signals indicative of incorporation of individual nucleotides into the double-stranded nucleic acid molecule. Signals indicative of incorporation events may include changes in impedance, conductance, or charge in the electronic double layer. In an example, signals indicative of incorporation of individual nucleotides are electrical signals garneted by an impedance or impedance change in the charge double layer. The signals indicative of incorporation of individual nucleotides may be steady state signals, transient signals, or a combination of steady state and transient signals. Signals may be detected transiently or during steady state conditions. In a transient signal detection modality, the detection occurs during or closely after nucleotide incorporation. In steady state detection, reading of the sensor may occur after the "completion" of the incorporation event. A steady state change in signal may remain until a change is introduced to the environment around the sensor.

The one or more computer processors may be programmed to direct fluid flow across the sensor array. The double-stranded nucleic acid molecules may be stably coupled to one or more surfaces during fluid flow conditions. The double-stranded nucleic acid molecules may be stably coupled to a plurality of beads. The beads may be stably disposed adjacent to the sensor array. The beads may be held adjacent to the sensor array by a magnetic or electric field. The fluid flow may not disrupt or move the beads. The fluid directed across the sensor array may include nucleic acid molecules, primers, polymerizing enzymes, individual nucleotides, co-factors used for a nucleotide incorporation reaction (e.g., primer extension reaction), and/or buffers. The fluid may be a washing fluid comprising buffers. In an example, a fluid may be directed to the sensor array and incubated with the sensor array. The fluid may be incubated with the sensor array for the duration of a single cycle of the nucleotide incorporation reaction. Between incubation cycles, the sensor array may be washed with a washing fluid.

In another aspect, the present disclosure provides a system for nucleic acid sequencing. The system may comprise a sensor array comprising a plurality of sensors. During use a first single-stranded nucleic acid molecule of a plurality of single-stranded nucleic acid molecules may be disposed adjacent to a given sensor of the sensor array. The given sensor may be electrically coupled to a charge double layer (e.g., within a Debye length of) the first single-stranded nucleic acid molecule. The system may comprise one or more computer processors couple to the sensor array. The one or more computer processors may be programed to bring the first single-stranded nucleic acid molecule into contact with individual nucleotides to subject the first single-stranded nucleic acid molecule to a nucleic acid incorporation reaction which generates a second single-stranded nucleic acid molecule from the individual nucleotides. The second single-stranded nucleic acid molecule may have sequence complementarity with the first single-stranded nucleic acid molecule. At least a subset of the individual nucleotides may comprise detectable labels. A given sensor may detect signals from the detectable labels during or subsequent to the nucleic acid incorporation reaction. The signals may be indicative of incorporation of the individual nucleotides into the second single-stranded nucleic acid molecule. The signals may be used to determine a sequence of the first single-stranded nucleic acid molecule.

The single-stranded nucleic acid molecule may be coupled to a support. The support may be a bead or a surface of the sensor array. A plurality of single-stranded nucleic acid molecules may be coupled to a plurality of beads or a plurality of locations on the surface of the sensor array. Each bead of the plurality of beads may be disposed adjacent to a given sensor. The plurality of beads may be magnetic or non-magnetic beads. The beads may have a surface coating that facilitates coupling of the single-stranded nucleic acid molecule to the bead. The charge double layer (e.g., Debye length) may be adjacent to the surface of the bead. Alternatively, or in addition to, the plurality of double-stranded nucleic acid molecules may be coupled to one or more surfaces of the sensor array. A given single-stranded nucleic acid molecule may be coupled to a surface of a given sensor. The charge double layer (e.g., Debye length) may be adjacent to the surface of the given sensor. The single-stranded nucleic acid molecule coupled to the bead or surface of the sensor array may be clonally amplified prior to sequencing so that each bead is coupled to a clonal population of single-stranded nucleic acid molecules or so that each surface of a given sensor is coupled to a clonal population of single-stranded nucleic acid molecules.

A given sensor may comprise at least one, at least two, at least three, or at least four electrodes. In an example, a given sensor comprises at least two electrodes. In another example, a given sensor comprises two electrodes. The electrodes may be exposed to the solution in which the primer extension reaction takes place. Alternatively, or in addition to, the electrodes may be buried within the sensor array and, therefore, may not be exposed to the solution in which the primer extension reaction takes place. The electrodes of a given sensor may detect signals indicative of incorporation of individual nucleotides into the single-stranded nucleic acid molecule. Signals indicative of incorporation events may include changes in impedance, conductance, or charge in the electronic double layer. In an example, signals indicative of incorporation of individual nucleotides are electrical signals garneted by an impedance or impedance change in the charge double layer. The signals indicative of incorporation of individual nucleotides may be steady state signals, transient signals, or a combination of steady state and transient signals. Signals may be detected transiently or during steady state conditions. In a transient signal detection modality, the detection occurs during or closely after nucleotide incorporation. In steady state detection, reading of the sensor may occur after the completion of the incorporation event. A steady state change in signal may remain until a change is introduced to the environment around the sensor. The sensor may detect incorporation events (e.g., count incorporation events) or may individually resolve incorporated nucleotides (e.g., determine which nucleotide is incorporated).

The one or more computer processors may be programmed to direct fluid flow across the sensor array. The single-stranded nucleic acid molecules may be stably coupled to one or more surfaces during fluid flow conditions. The single-stranded nucleic acid molecules may be stably coupled to a plurality of beads. The beads may be stably disposed adjacent to the sensor array. The beads may be held adjacent to the sensor array by a magnetic or electric field. The fluid flow may not disrupt or move the beads. The fluid directed across the sensor array may include nucleic acid molecules, primers, polymerizing enzymes, individual nucleotides, co-factors used for a nucleotide incorporation reaction (e.g., primer extension reaction), and/or buffers. The fluid may be a washing fluid comprising buffers. In an example, a fluid may be directed to the sensor array and incubated with the sensor array. The fluid may be incubated with the sensor array for the duration of a single cycle of the nucleotide incorporation reaction. Between incubation cycles, the sensor array may be washed with a washing fluid.

In another aspect, the present disclosure provides a system for nucleic acid sequencing. The system may comprise a sensor array comprising a plurality of sensors. During use a first single-stranded nucleic acid molecule of a plurality of single-stranded nucleic acid molecules may be disposed adjacent to a given sensor of the sensor array. The system may comprise one or more computer processors operatively coupled to the sensor array. The one or more computer processors may be programmed to subject the first single-stranded nucleic acid molecule to a nucleic acid incorporation reaction that comprises alternately and sequentially incorporating individual nucleotides of a first plurality of nucleotides comprising detectable labels and exchanging the individual nucleotides of the first plurality of nucleotides with individual nucleotides of a second plurality of nucleotides that do not comprise detectable labels. A given sensor may detect signals from the detectable labels during or subsequent to the nucleic acid incorporation reaction. The signals may be indicative of incorporation of the individual nucleotides into the second single-stranded nucleic acid molecule. The signals may be used to determine a sequence of the first single-stranded nucleic acid molecule.

The plurality of single stranded-nucleic acid molecules may be coupled to a plurality of supports. The plurality of supports may be a plurality of beads or a plurality of surfaces on the sensor array. In an example, the plurality of single-stranded nucleic acid molecules may be coupled to a plurality of beads and a given single-stranded nucleic acid molecule may be coupled to a given bead. A given sensor may be electrically coupled to a charge double layer comprising the first single-stranded nucleic acid molecule. The charge double layer may be adjacent to a surface of the given bead or on the surface of a given sensor. The single-stranded nucleic acid molecule may be amplified on the surface of the support. The amplification products may be coupled to the surface of the support. The amplification products may form a clonal colony of single-stranded nucleic acid molecules on the surface of the support. The clonal colony of single-stranded nucleic acid molecules may be sequenced.

A given sensor of the sensor array may comprise at least one, at least two, at least three, at least four, or more electrodes. In an example, a given sensor comprises at least two electrodes. In another example, a given sensor comprises two electrodes. The electrodes may be exposed to the solution in which the primer extension reaction takes place. Alternatively, or in addition to, the electrodes may be buried within the sensor array and, therefore, may not be exposed to the solution in which the primer extension reaction takes place. The sensor may detect signals indicative of nucleotide incorporation events. The sensor may detect the detectable label coupled to the individual nucleotides. The sensor may detect the detectable label during transient or steady state conditions. Nucleotide incorporation may be detected once, twice, three times, four times, or more than four times per incorporation cycle during steady state conditions. In an example, nucleotide incorporation may be detected at least twice per incorporation cycle during steady state conditions. The sensor array may detect electrical signals during transient or steady state conditions. The electrical signals may include, but are not limited to, changes in charge state of a molecule, changes in the conductivity of a surrounding solution, impedance signals, or changes in impedance signals. The sensor may detect a change in charge and/or conductivity or a change in impedance. The sensor may detect the change in charge and/or conductivity or impedance within a charge double layer (e.g., Debye length) of the sensor, support, or nucleic acid molecule (e.g., the sample). The detectable labels coupled to the individual nucleotides may alter the electrical environment surrounding the single-stranded nucleic acid molecules and a given sensor may detect the electrical change. The sensor may detect incorporation events (e.g., count incorporation events) or may individually resolve incorporated nucleotides (e.g., determine which nucleotide is incorporated).

The one or more computer processors may be programmed to direct fluid flow across the sensor array. The single-stranded nucleic acid molecules may be stably coupled to one or more surfaces during fluid flow conditions. The single-stranded nucleic acid molecules may be stably coupled to a plurality of beads. The beads may be stably disposed adjacent to the sensor array. The beads may be held adjacent to the sensor array by a magnetic or electric field. The fluid flow may not disrupt or move the beads. The fluid directed across the sensor array may include nucleic acid molecules, primers, polymerizing enzymes, individual nucleotides, co-factors used for a nucleotide incorporation reaction (e.g., primer extension reaction), and/or buffers. The fluid may be a washing fluid comprising buffers. In an example, a fluid may be directed to the sensor array and incubated with the sensor array. The fluid may be incubated with the sensor array for the duration of a single cycle of the nucleotide incorporation reaction. Between incubation cycles, the sensor array may be washed with a washing fluid.

Computer Systems

Figure 16:
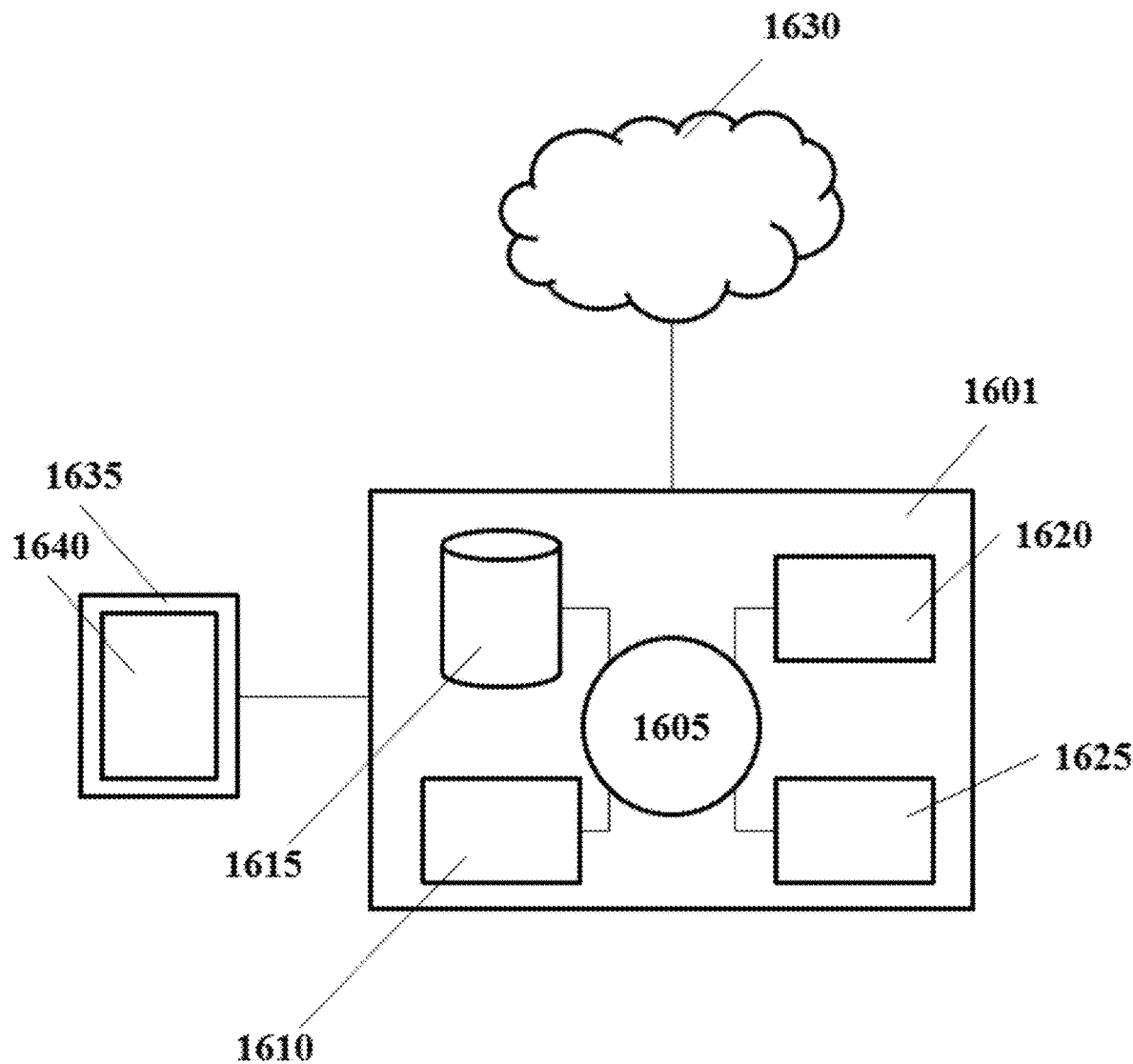
FIG. 16 shows a computer system that is programmed or otherwise configured to implement methods provided herein.

The present disclosure provides computer systems that are programmed to implement methods of the disclosure. FIG. 16 shows a computer system 1601 that is programmed or otherwise configured to sequence nucleic acid molecules. The computer system 1601 can regulate various aspects of the sequencing system of the present disclosure, such as, for example, controlling flow of nucleic acid templates to the sensor array, controlling flow of individual nucleotides to the sensor array, and controlling incorporation reaction conditions. The computer system 1601 can be an electronic device of a user or a computer system that is remotely located with respect to the electronic device. The electronic device can be a mobile electronic device.

The computer system 1601 includes a central processing unit (CPU, also "processor" and "computer processor" herein) 1605, which can be a single core or multi core processor, or a plurality of processors for parallel processing. The computer system 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The computer system 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the computer system 1601, can implement a peer-to-peer network, which may enable devices coupled to the computer system 1601 to behave as a client or a server.

The CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and writeback.

The CPU 1605 can be part of a circuit, such as an integrated circuit. One or more other components of the system 1601 can be included in the circuit. In some cases, the circuit is an application specific integrated circuit (ASIC).

The storage unit 1615 can store files, such as drivers, libraries and saved programs. The storage unit 1615 can store user data, e.g., user preferences and user programs. The computer system 1601 in some cases can include one or more additional data storage units that are external to the computer system 1601, such as located on a remote server that is in communication with the computer system 1601 through an intranet or the Internet.

The computer system 1601 can communicate with one or more remote computer systems through the network 1630. For instance, the computer system 1601 can communicate with a remote computer system of a user (e.g., laptop or cellular phone of a user). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1601 via the network 1630.

Methods as described herein can be implemented by way of machine (e.g., computer processor) executable code stored on an electronic storage location of the computer system 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1601 can include or be in communication with an electronic display 1635 that comprises a user interface (UI) 1640 for providing, for example, current operating conditions of the system or sequencing results. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1605. The algorithm can, for example, convert signals indicative of nucleotide incorporation into a nucleic acid sequence.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing or analyzing a nucleic acid molecule, comprising:
   (a) providing a sensor that is electrically coupled to a charge double layer comprising at least a portion of said nucleic acid molecule;
   (b) bringing said nucleic acid molecule in contact with a nucleotide coupled to an effector in presence of a polymerizing enzyme under conditions sufficient to incorporate said nucleotide into a growing strand complementary to said nucleic acid molecule, wherein said effector is capable of modulating charge distribution at said nucleotide;
   (c) subsequent to (b), detecting one or more signals associated with said charge double layer with said sensor, which one or more signals are indicative of said nucleotide coupled to said effector having been incorporated into said growing strand, wherein said effector modulates charge distribution at said nucleotide during said detecting; and
   (d) reducing effects of said effector on said charge distribution at said nucleotide.

2. The method of claim 1, wherein said nucleic acid molecule is coupled to a bead.

3. The method of claim 1, wherein said nucleic acid molecule is coupled to a surface of said sensor.

4. The method of claim 1, wherein said nucleic acid molecule is among a plurality of nucleic acid molecules having sequence homology with one another, and wherein said charge double layer comprises said plurality of nucleic acid molecules.

5. The method of claim 1, wherein said sensor is part of a sensor array.

6. The method of claim 1, wherein said effector is coupled to a nucleobase of said nucleotide.

7. The method of claim 1, wherein said effector is an electrostatic moiety.

8. The method of claim 1, wherein (d) comprises removing said effector from said nucleotide.

9. The method of claim 1, wherein said nucleotide comprises a reversible terminator that prevents an additional nucleotide from stably hybridizing to said nucleic acid molecule.

10. The method of claim 9, further comprising removing said reversible terminator subsequent to (c) and prior to incorporation of another nucleotide into said growing strand.

11. The method of claim 1, wherein said nucleotide is among a plurality of nucleotides of different types, and wherein (b) comprises bringing said nucleic acid molecule in contact with said plurality of nucleotides.

12. The method of claim 11, wherein said plurality of nucleotides are reversibly coupled to a single type of effector.

13. The method of claim 11, wherein said plurality of nucleotides are reversibly coupled to different types of effectors.

14. The method of claim 1, wherein said one or more signals are steady state signals.

15. The method of claim 1, wherein said one or more signals are electrical signals generated by an impedance or change in impedance in said charge double layer.

16. The method of claim 1, wherein said one or more signals are electrical signals generated by a conductivity or change in conductivity in said charge double layer.

17. The method of claim 1, wherein said one or more signals are electrical signals generated by charge or change in charge in said charge double layer.

18. The method of claim 1, wherein said sensor comprises a plurality of electrodes in contact with said charge double layer.

19. The method of claim 1, wherein (b)-(d) are repeated until a sequence or a length of said nucleic acid molecule is determined.

* * * * *

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5
```

-continued

```
<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tt                                                          12

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ile Glu Thr Asp Ile Glu Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Asp Gly Asp Phe Asp Gly Asp
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Thr Leu Pro Leu Pro Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Lys Lys Lys Lys Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
```

```
<223> OTHER INFORMATION: Gamma-carboxyglutamic acid

<400> SEQUENCE: 7

Glu Glu Glu Glu Glu Glu
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: Gamma-carboxyglutamic acid

<400> SEQUENCE: 8

Glu Glu Glu Glu Glu Glu Glu Glu Glu Glu Glu Glu
1               5                   10
```